United States Patent
Bovin et al.

(10) Patent No.: US 9,353,349 B2
(45) Date of Patent: *May 31, 2016

(54) SYNTHETIC MEMBRANE ANCHORS

(71) Applicant: KODE BIOTECH LIMITED, Auckland (NZ)

(72) Inventors: Nicolai Bovin, Moscow (RU); Lissa Gilliver, Auckland (NZ); Stephen Henry, Auckland (NZ); Elena Korchagina, Moscow (RU)

(73) Assignee: KODE BIOTECH LIMITED, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 14/108,749

(22) Filed: Dec. 17, 2013

(65) Prior Publication Data

US 2014/0186950 A1    Jul. 3, 2014

Related U.S. Application Data

(60) Continuation of application No. 13/067,021, filed on May 3, 2011, now Pat. No. 8,637,473, which is a division of application No. 10/593,829, filed as application No. PCT/NZ2005/000052 on Mar. 22, 2005, now Pat. No. 8,013,131.

(30) Foreign Application Priority Data

Mar. 22, 2004   (NZ) ........................................ 531866
Jan. 28, 2005   (NZ) ........................................ 537941

(51) Int. Cl.
| | |
|---|---|
| C12N 5/078 | (2010.01) |
| C07F 9/10 | (2006.01) |
| C07H 15/04 | (2006.01) |
| C12N 5/00 | (2006.01) |
| C12N 5/073 | (2010.01) |
| A61K 35/12 | (2015.01) |

(52) U.S. Cl.
CPC ............... *C12N 5/0641* (2013.01); *C07F 9/10* (2013.01); *C07H 15/04* (2013.01); *C12N 5/0006* (2013.01); *C12N 5/0604* (2013.01); *A61K 2035/124* (2013.01)

(58) Field of Classification Search
None
See application file for complete search history.

(56) References Cited

U.S. PATENT DOCUMENTS

| | | | |
|---|---|---|---|
| 4,783,400 A | 11/1988 | Canova-Davis et al. | |
| 4,873,322 A | 10/1989 | Fechtig et al. | 536/4.1 |
| 5,334,583 A | 8/1994 | Lukas et al. | |
| 5,854,218 A | 12/1998 | DeFrees | |
| 6,063,752 A | 5/2000 | Ehrhardt et al. | |
| 6,949,663 B2 | 9/2005 | Tsuchida et al. | |

FOREIGN PATENT DOCUMENTS

| | | |
|---|---|---|
| EP | 0 381 070 A1 | 8/1990 |
| JP | 6-40953 | 2/1994 |
| WO | WO 01/40796 A2 | 6/2001 |
| WO | WO 01/91805 A2 | 12/2001 |
| WO | WO 03/034074 A1 | 4/2003 |
| WO | WO 03087346 A1 | 10/2003 |

OTHER PUBLICATIONS

Moutard, et al, *Journal of Inclusion Phenomena and Macrocyclic Chemistry*, vol. 44; pp. 317-322 (2002).

Park, et al; *Biochemica et Biophysica Acta.*, vol. 1166, pp. 105-114 (1993).

Definition of "glycoside," downloaded from the internet Apr. 17, 2013.

Blixt, O., et al; "Printed covalent glycan array for ligand profiling of diverse glycan binding proteins"; *PNAS*, vol. 101, No. 49, pp. 117033-17038 (2004).

Kovalenko, E.I., et al; "The Modification of Cell Surface with Lipophilic Glycoconjugates and the Interaction of Modified Cells with Natural Killer Cells"; *Russian Journal of Bioorganic Chemistry*, vol. 30, No. 3, pp. 250-260 (2004).

Ångström, Jonas, et al; "Default biosynthesis pathway for blood group-related glycolipids in human small intestine as defined by structural identification of linear and branched glycosylceramides in a group O Le(a-b-) nonsecretor"; *Glycobiology*, vol. 14, No. 1, pp. 1-12 (2004).

Duk, Maria, et al; "Specificity of human anti-NOR antibodies, a distinct species of "natural" anti-α-galactosyl antibodies"; *Glycobiology*, vol. 13, No. 4, pp. 279-284 (2003).

Paulson, James C., et al; "Sialyltransferases as targets for development of immuno-suppressants"; Abstracts of Papers, 223rd ACS National Meeting, Orlando, FL, United States, Apr. 7-11, 2002, CaRB-095 Publisher: *American Chemical Society*, Washington, DC.

Krasilshchikova, M.S., et al; "Macrophage-Tumor Cell Interaction in Byrb Mouse Leukosis Model"; *Baltic J. Lab. Animal. Sci.*; vol. 12; pp. 68-73 (2002).

Kovalenko, E.I., et al; "The Incorporation of Neoglycolipids into K562 Cells: A Model for the Study of Carbohydrate-Dependent Cytolysis of Target Cells by Natural Killer Cells"; *Bioorgancheskaya Khimiya*; vol. 24, No. 3, pp. 224-228 (1998).

Henry, Stephen, et al; "Structural and immunochemical identification of Le[a], Le[b], H type 1, and related glycolipids in small intestinal mucosa of a group O Le(a b ) nonsecretor"; *Glycoconjugate Journal*, vol. 14; pp. 209-223 (1997).

(Continued)

*Primary Examiner* — Layla Bland

(74) *Attorney, Agent, or Firm* — Nixon & Vanderhye P.C.

(57) ABSTRACT

Cells incorporating a synthetic molecule construct of the structure F—$S_1$-$S_2$-L where: F—$S_1$ is an aminoalkylglycoside where F is a mono-, di-, tri- or oligo-saccharide and $S_1$ is 2-aminoethyl, 3-aminopropyl, 4-aminobutyl, or 5-aminopentyl; $S_2$ is —CO(CH$_2$)$_2$CO—, —CO(CH$_2$)$_3$CO—, —CO(CH$_2$)$_4$CO— or —CO(CH$_2$)$_5$CO—; and L is phosphatidylethanolamine.

15 Claims, 10 Drawing Sheets

(56) References Cited

OTHER PUBLICATIONS

Henry, Stephen., et al; "Lewis Histo-Blood Group System and Associated Secretory Phenotypes"; *Vox Sanguinis*, vol. 69, No. 3, pp. 166-182 (1995).

Henry, Stephen M., et al; "Structural and immunochemical identification of Le$^b$ glycol-lipids in the plasma of a group O Le(a−b−) secretor"; *Glycoconjugate Journal*, vol. 12, pp. 309-317 (1995).

Henry, Stephen M., et al; "Immunochemical and immunohistological expression of Lewis histo-blood group antigens in small intestine including individuals of the Le(a+b+) and Le(a−b−) nonsecretor phenotypes"; *Glycoconjugate Journal*, vol. 11; pp. 600-607 (1994).

Henry, Stephen M., et al; "Expression of Lewis histo-blood group glycolipids in the plasma of individuals of Le(a+b+) and partial secretor phenotypes"; *Glycoconjugate Journal*, vol. 11; pp. 593-599 (1994).

Bovin, Nicolai V., et al; "Synthesis of polymeric neoglycoconjugates based on N-substituted polyacrylamides"; *Glycoconjugate Journal*,; vol. 10, pp. 142-151 (1993).

Vodovozova, E.L., et al; "Antitumour activity of cytotoxic liposomes equipped with selectin ligand SiaLe$^x$, in a mouse mammary adenocarcinoma model"; *European Journal of Cancer*; vol. 36, pp. 942-949 (2000).

Derwent Abstract Accession No. 2004-449665142 A25 B04 (A96) WO 2004/045583 A1 (Nipro Corporation) Jun. 3, 2004.

Massaguer, A., et al; "Synthesis of RGD containing peptides. Comparative study of their incorporation to the surface of 5-fluorouridine loaded liposomes"; *Journal of Liposome Research* (2001), 11(1), 103-113.

Ishida, O., et al; "Liposomes bearing polyethyleneglycol-coupled transferring with intracellular targeting property to the solid tumors in vivo"; *Pharmaceutical Research* (2001), 18(7), 1042-1048.

Haselgrubler, Thomas, et al; "Synthesis and Applications of a New Poly(ethylene glycol) Derivative for the Crosslinking of Amines with Thiols"; *Bioconjugate Chemistry* (1995), 6(3), 242-8.

Blume, G., et al; "Specific targeting with polyethylene glycol-modified liposomes: coupling of homing devices to the ends of the polymeric chains combines effective target binding with long circulation times"; *Biochimica et Biophysica Acta* (1993), 1149(1), 180-4.

Becker, B., et al; "A simple synthesis of 8-(methoxycarbonyl)octly 3,6-di-O-(α-D-mannopyranoside and derivatives and their use in the preparation of neoglycoconjugates"; *Carbohydrate Research*; vol. 315, pp. 148-158 (1999).

Furneaux, R.H., et al; "New mannotriosides and trimannosides as potential ligands for mannose-specific binding proteins"; *Can J. Chem.*; vol. 80, pp. 964-972 (2002).

Gallot, B., et al; "Study by X-Ray Diffraction of the Geometrical Shape of Glycoprotein Sugar Chains in Two Model Glycoconjugates, A Liposaccharide and a Phospholiposaccharide, Having the Same Sugar Chain"; *Carbohydrate Research*; vol. 149; pp. 309-318 (1986).

Ghosh, P., et al; "Synthetic Glycolipids: Interaction with Galactose-Binding Lectin and Hepatic Cells"; *Archives of Biochemistry and Biophysics*; vol. 206, No. 2; pp. 454-457 (1981).

Moutard, S., et al; "Novel Glycolipids Based on Cyclodextrins"; *Journal of Inclusion Phenomena and Macrocyclic Chemistry*; vol. 44, pp. 317-322 (2002).

Oohira, A., et al; "Effects of Lipid-Derivatized Glycosaminoglycans (GAGs), a Novel Probe for Functional Analyses of GAGs, on Cell-to-Substratum Adhesion and Neurite Elongation in Primary Cultures of Fetal Rat Hippocampal Neurons"; *Archives of Biochemistry and Biophysics*; vol. 378, No. 1, pp. 78-83 (2000).

Pacuszka, T., et al; "Generation of Cell Surface Neoganglioproteins"; *The Journal of Biological Chemistry*; vol. 265, No. 13, pp. 7673-7678 (1990).

Pacuszka, T., et al; "Neoglycolipid Analogues of Ganglioside $G_{M1}$ as Functional Receptors of Cholera Toxin"; *Biochemistry*, vol. 30, No. 10, pp. 2563-2570 (1991).

Park, Y.S., et al; "Effect of chemically modified $G_{M1}$ and neoglycolipid analogs of $G_{M1}$ on liposome circulation time: evidence supporting the dysopsonin hypothesis"; *Biochimica et Biophysica Acta*; vol. 1166, pp. 105-114 (1993).

Van Boeckel, C.A.A., et al; "Synthesis of Glucosylphosphatidylglycerol Via a Phosphotriester Intermediate"; *Tetrahedron Letters*; No. 37, pp. 3561-3564 (1979).

Day 8

SYNTHETIC MEMBRANE ANCHORS

This application is a continuation of application Ser. No. 13/067,021, filed May 3, 2011, U.S. Pat. No. 8,637,473, which is a divisional of application Ser. No. 10/593,829, filed Jan. 12, 2007, U.S. Pat. No. 8,013,131, which is a 371 of International Application No. PCT/NZ2005/000052, filed Mar. 22, 2005 which claims priority to New Zealand Patent Application No. 531866, filed Mar. 22, 2004, and 537941, filed Jan. 28, 2005, the entire contents of each of which are hereby incorporated by reference.

FIELD OF INVENTION

The invention relates to synthetic molecules that spontaneously and stably incorporate into lipid bi-layers, including cell membranes. Particularly, although not exclusively, the invention relates to the use of these molecules as synthetic membrane anchors or synthetic molecule constructs to effect qualitative and quantitative changes in the expression of cell surface antigens.

BACKGROUND

Cell surface antigens mediate a range of interactions between cells and their environment. These interactions include cell-cell interactions, cell-surface interactions and cell-solute interactions. Cell surface antigens also mediate intra-cellular signalling.

Cells are characterised by qualitative and quantitative differences in the cell surface antigens expressed. Qualitative and quantitative changes in the cell surface antigens expressed alter both cell function (mode of action) and cell functionality (action served).

Being able to effect qualitative and/or quantitative changes in the surface antigens expressed by a cell has diagnostic and therapeutic value. Transgenic and non-transgenic methods of effecting qualitative and/or quantitative changes in the surface antigens expressed by a cell are known.

Protein painting is a non-transgenic method for effecting qualitative and/or quantitative changes in the surface antigens expressed by a cell. The method exploits the ability of GPI linked proteins to spontaneously anchor to the cell membrane via their lipid tails. The method described in the specification accompanying international application no. PCT/US98/15124 (WO 99/05255) includes the step of inserting a GPI linked protein isolated from a biological source into a membrane. Isolated GPI-anchored proteins are stated as having an unusual capacity to reintegrate with a cell-surface membrane.

Cells exist in an aqueous environment. The cell membrane is a lipid bilayer that serves as a semi-permeable barrier between the cytoplasm of the cell and this aqueous environment. Localising antigens to the cell surface may also be achieved by the use of glycolipids as membrane anchors.

The method described in the specification accompanying international application no. PCT/NZ02/00214 (WO 03/034074) includes the step of inserting a controlled amount of glycolipid into a membrane. The amount of glycolipid inserted is controlled to provide cells with a desired level of antigen expression.

The method described in the specification accompanying international application no. PCT/NZ03/00059 (WO 03/087346) includes the step of inserting a modified glycolipid into a membrane as a "membrane anchor". The modified glycolipid provides for the localisation of antigens to the surface of the cell or multicellular structure. New characteristics may thereby be imparted on the cell or multicellular structure.

These methods typically include the isolation of a glycolipid or glycolipid-linked antigen from a biological source. The isolation of glycolipids or glycolipid-linked antigens from biological sources is costly, variable and isolatable amounts are often limited. Obtaining reagents from zoological sources for therapeutic use is particularly problematic, especially where the reagent or its derivative products are to be administered to a human subject.

Synthetic molecules for which the risk of contamination with zoo-pathogenic agents can be excluded are preferred. Synthetic counterparts for naturally occurring glycolipids and synthetic neo-glycolipids have been reported. However, for a synthetic glycolipid to be of use as a membrane anchor it must be able to spontaneously and stably incorporate into a lipid bi-layer from an aqueous environment. The utility of synthetic glycolipids in diagnostic or therapeutic applications is further limited to those synthetic glycolipids that will form a solution in saline.

Organic solvents and/or detergents used to facilitate the solubilization of glycolipids in saline must be biocompatible. Solvents and detergents must often be excluded or quickly removed as they can be damaging to some cell membranes. The removal of solvents or detergents from such preparations can be problematic.

Damage to cell membranes is to be avoided especially where the supply of cells or multicellular structures is limited, e.g. embryos, or the cells are particularly sensitive to perturbation, e.g. hepatocytes.

There exists a need for water soluble synthetic molecules that are functionally equivalent to naturally occurring glycolipids and glycolipid-linked antigens in respect of their ability to spontaneously and stably incorporate into lipid bi-layers, including cell membranes.

Providing such synthetic molecules would obviate the limitations of glycolipids and glycolipid-linked antigens isolated from biological sources and facilitate being able to effect qualitative and/or quantitative changes in the surface antigens expressed by a cell.

It is an object of this invention to provide such synthetic molecules and a method for their preparation. It is a further object of this invention to provide synthetic molecules for use in diagnostic and therapeutic applications. The preceding objects are to be read disjunctively with the object to at least provide the public with a useful choice.

STATEMENTS OF INVENTION

In a first aspect the invention consists in a synthetic membrane anchor or synthetic molecule construct of the structure F—$S_1$-$S_2$-L where:
  F is selected from the group consisting of carbohydrates;
  $S_1$-$S_2$ is a spacer linking F to L; and
  L is a lipid selected from the group consisting of diacyl- and dialkyl-glycerolipids, including glycerophospholipids, and sphingosine derived diacyl- and dialkyl-lipids, including ceramide.

Preferably L is a lipid selected from the group consisting of diacyl- and dialkyl-glycerolipids, including glycerophospholipids. More preferably L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docosenoic acid. More preferably the lipid is derived from one or more cis-desaturated fatty acids. Most preferably L is selected from the group consisting of: 1,2-O-dioleoyl-sn-glycero-3-phosphatidylethanolamine (DOPE), 1,2-O-distearyl-sn-glycero-3-phosphatidylethanolamine (DSPE) and rac-1,2-dioleoylglycerol (DOG).

Preferably L is a glycerophospholipid and the molecule includes the substructure:

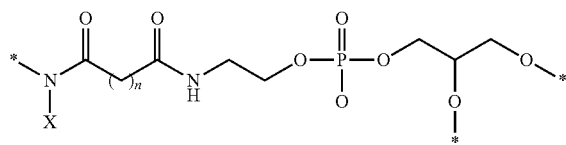

where n=3 to 5, X is H or C, and * is other than H. Preferably n is 3.

Preferably the molecule is water soluble.

Preferably the molecule spontaneously incorporates into a lipid bi-layer when a solution of the molecule is contacted with the lipid bi-layer. More preferably the molecule stably incorporates into the lipid bilayer.

Preferably F, $S_1$, $S_2$ and L are covalently linked.

Preferably F is selected from the group consisting of naturally occurring or synthetic glycotopes.

$S_1$-$S_2$ is selected to provide a water soluble synthetic membrane anchor or synthetic molecule construct.

In a first embodiment F is a naturally occurring or synthetic glycotope. Preferably F is a naturally occurring or synthetic glycotope consisting of three (trisaccharide) or more sugar units. More preferably F is a glycotope selected from the group consisting of lacto-neo-tetraosyl, lactotetraosyl, lacto-nor-hexaosyl, lacto-iso-octaosyl, globoteraosyl, globo-neo-tetraosyl, globopentaosyl, gangliotetraosyl, gangliotriaosyl, gangliopentaosyl, isoglobotriaosyl, isoglobotetraosyl, mucotriaosyl and mucotetraosyl series of oligosaccharides.

Most preferably F is selected from the group of glycotopes comprising the terminal sugars GalNAcα1-3(Fucα1-2)Galβ; Galα1-3Galβ; Galβ; Galα1-3(Fucα1-2)Galβ; NeuAcα2-3Galβ; NeuAcα2-6Galβ; Fucα1-2Galβ; Galβ1-4GlcNAcβ1-6(Galβ1-4GlcNAcβ1-3)Galβ; Fucα1-2Galβ1-4GlcNAcβ1-6(Fucα1-2Galβ1-4GlcNAcβ1-3)Galβ; Fucα1-2Galβ1-4GlcNAcβ1-6(NeuAcα2-3Galβ1-4GlcNAcβ1-3) Galβ; NeuAcα2-3Galβ1-4GlcNAcβ1-6(NeuAcα2-3Galβ1-4GlcNAcβ1-3)Galβ; Galα1-4Galβ1- 4Glc; GalNAcβ1-3Galα1-4Galβ1-4Glc; GalNAcα1-3GalNAcβ1-3Galα1-4Galβ1-4Glc; or GalNAcβ1-3GalNAcβ1-3Galα1-4Galβ1-4Glc.

When F is a glycotope, L is a glycerophospholipid and $S_2$ is selected from the group including: —CO(CH$_2$)$_3$CO—, —CO(CH$_2$)$_4$CO— (adipate), —CO(CH$_2$)$_5$CO— and —CO(CH$_2$)$_5$NHCO(CH$_2$)$_5$CO—, preferably $S_1$ is a $C_{3-5}$-aminoalkyl selected from the group consisting of: 3-aminopropyl, 4-aminobutyl, or 5-aminopentyl. More preferably $S_1$ is 3-aminopropyl.

In a second embodiment F is a molecule that mediates a cell-cell or cell-surface interaction. Preferably F is a carbohydrate with an affinity for a component expressed on a targeted cell or surface. More preferably F has an affinity for a component expressed on epithelial cells or extra-cellular matrices. Yet more preferably F has an affinity for a component expressed on the epithelial cells or the extra-cellular matrix of the endometrium. Most preferably the component expressed on the epithelial cells or the extra-cellular matrix of the endometrium can be a naturally expressed component or an exogenously incorporated component.

In a third embodiment F is a molecule that mediates a cell-solute interaction. Preferably F is a ligand for a binding molecule where the presence of the binding molecule is diagnostic for a pathological condition. More preferably F is a ligand for an antibody (immunoglobulin).

In specific embodiments the water soluble synthetic membrane anchor or synthetic molecule construct has the structure:

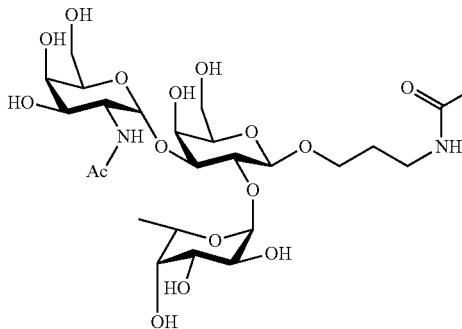 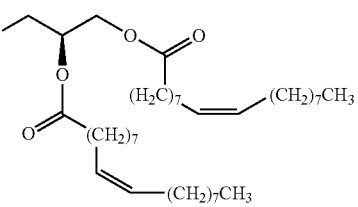

designated $A_{tri}$-sp-Ad-DOPE (I); the structure:

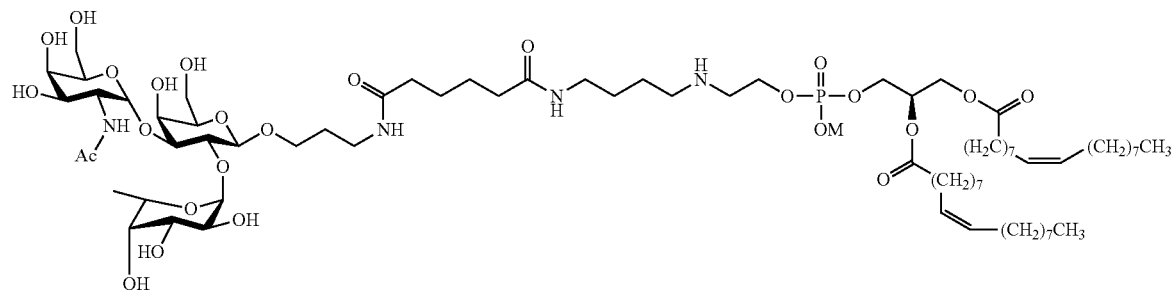

designated A*tri*-spsp₁-Ad-DOPE (II); the structure:
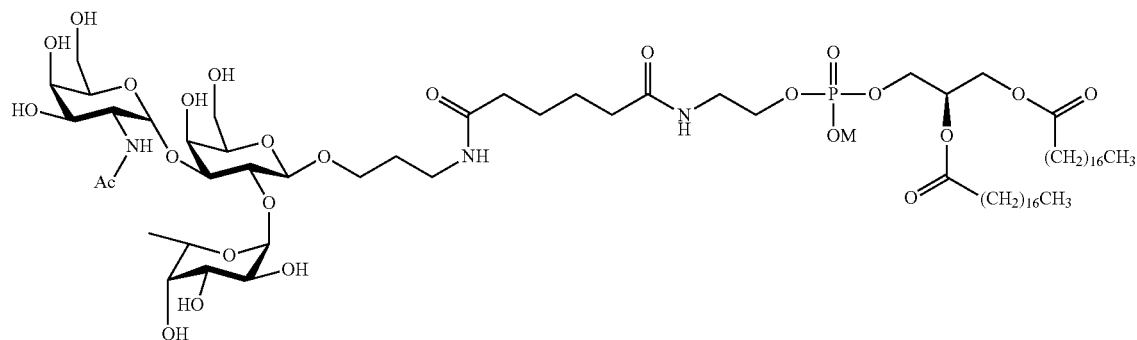
designated A*tri*-sp-Ad-DSPE (III); the structure
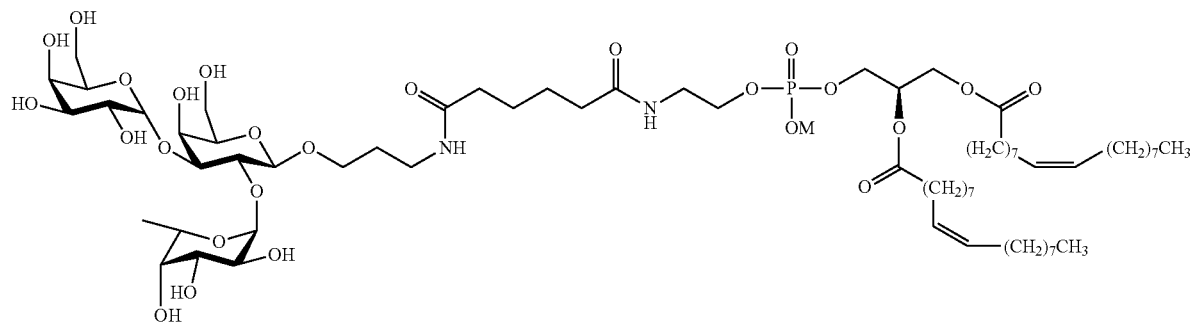
designated B*tri*-sp-Ad-DOPE (VI); the structure:
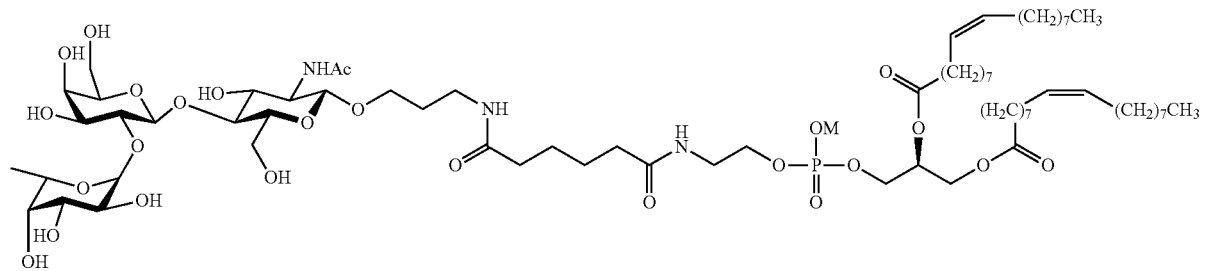
designated H*tri*-sp-Ad-DOPE (VII); the structure:
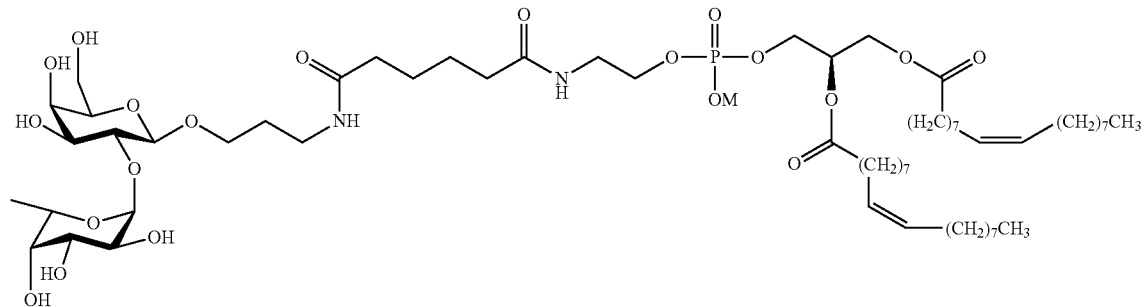

designated H$_{di}$-sp-Ad-DOPE (VIII); the structure:

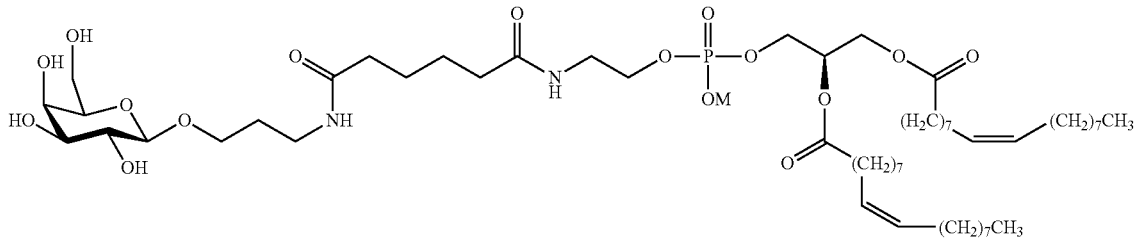

designated Galβ$_i$-sp-Ad-DOPE (IX); the structure:

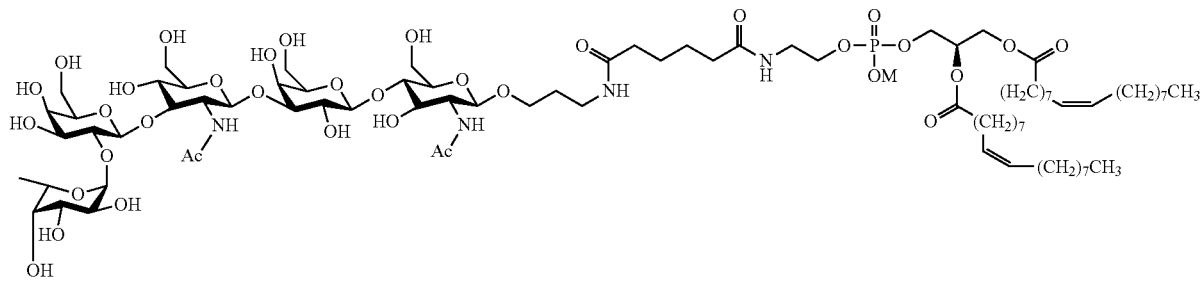

designated Fucα1-2Galβ1-3GlcNAcβ1-3Galβ1-4GlcNAc-sp-Ad-DOPE (XII); or the structure:

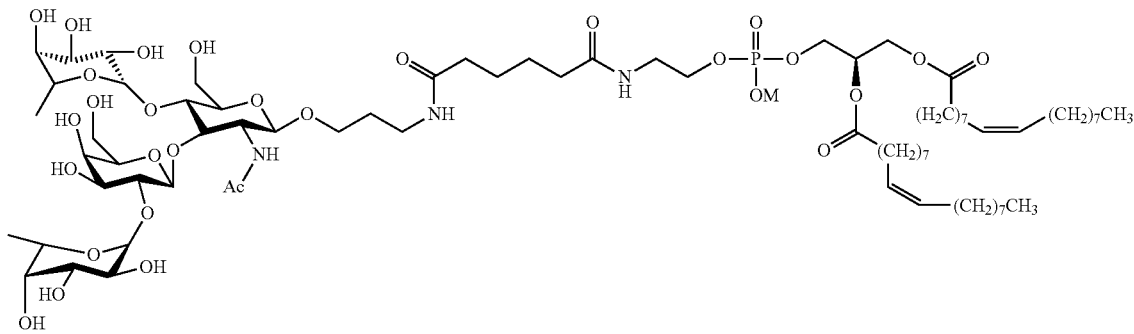

designated Fucα1-2Galβ1-3(Fucα1-4)GlcNAc-sp-Ad-DOPE (XIII).

M is typically H, but may be replaced by another monovalent cation such as Na$^+$, K$^+$ or NH$_4^+$.

In a second aspect the invention consists in a method of preparing a synthetic membrane anchor or synthetic molecule construct of the structure F—S$_1$-S$_2$-L including the steps:

1. Reacting an activator (A) with a lipid (L) to provide an activated lipid (A-L);
2. Derivatising an antigen (F) to provide a derivatised antigen (F—S$_1$); and
3. Condensing A-L with F—S$_1$ to provide the molecule;

where:

A is an activator selected from the group including: bis(N-hydroxysuccinimidyl), bis(4-nitrophenyl), bis(pentafluorophenyl), bis(pentachlorophenyl) esters of carbodioic acids (C$_3$ to C$_7$);

L is a lipid selected from the group consisting of diacyl- and dialkyl-glycerolipids, including glycerophospholipids, and sphingosine derived diacyl- and dialkyl-lipids, including ceramide.

F is selected from the group consisting of carbohydrates; and

S$_1$-S$_2$ is a spacer linking F to L where S$_1$ is selected from the group including: primary aminoalkyl, secondary aliphatic aminoalkyl or primary aromatic amine; and S$_2$ is absent or selected from the group including: —CO(CH$_2$)$_3$CO—, —CO(CH$_2$)$_4$CO— (adipate), and —CO(CH$_2$)$_5$CO—.

Preferably the molecule is water soluble.

Preferably the molecule spontaneously incorporates into a lipid bi-layer when a solution of the molecule is contacted with the lipid bi-layer. More preferably the molecule stably incorporates into the lipid bilayer.

Preferably F, S$_1$, S$_2$ and L are covalently linked.

Preferably F is selected from the group consisting of naturally occurring or synthetic glycotopes.

Preferably L is a lipid selected from the group consisting of diacyl- and dialkyl-glycerolipids, including glycerophospholipids. More preferably L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docosenoic acid. More preferably the lipid is derived from one or more cis-desaturated fatty acids. Most preferably L is selected from the group consisting of: 1,2-O-dioleoyl-sn-glycero-3-phosphatidylethanolamine (DOPE), 1,2-O-distearyl-sn-glycero-3-phosphatidylethanolamine (DSPE) and rac-1,2-dioleoylglycerol (DOG).

Preferably L is a glycerophospholipid and the molecule includes the substructure:

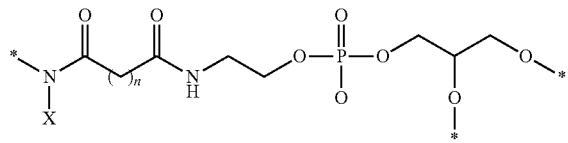

where n=3 to 5, X is H or C, and * is other than H. Preferably n is 3.

Preferably A (R—$S_2$) and $S_1$ are selected to provide a water soluble synthetic molecule construct.

In a first embodiment F is a naturally occurring or synthetic glycotope. Preferably F is a naturally occurring or synthetic glycotope consisting of three (trisaccharide) or more sugar units. More preferably F is a glycotope selected from the group consisting of lacto-neo-tetraosyl, lactotetraosyl, lacto-nor-hexaosyl, lacto-iso-octaosyl, globoteraosyl, globo-neo-tetraosyl, globopentaosyl, gangliotetraosyl, gangliotriaosyl, gangliopentaosyl, isoglobotriaosyl, isoglobotetraosyl, mucotriaosyl and mucotetraosyl series of oligosaccharides.

Most preferably F is selected from the group of glycotopes comprising the terminal sugars GalNAcα1-3(Fucα1-2)Galβ; Galα1-3Galβ; Galβ; Galα1-3(Fucα1-2)Galβ; NeuAcα2-3Galβ; NeuAcα2-6Galβ; Fucα1-2Galβ; Galβ1-4GlcNAcβ1-6(Galβ1-4GlcNAcβ1-3)Galβ; Fucα1-2Galβ1-4GlcNAcβ1-6(Fucα1-2Galβ1-4GlcNAcβ1-3)Galβ; Fucα1-2Galβ1-4GlcNAcβ1-6(NeuAcα2-3Galβ1-4GlcNAcβ1-3)Galβ; NeuAcα2-3Galβ1-4GlcNAcβ1-6(NeuAcα2-3Galβ1-4GlcNAcβ1-3)Galβ; Galα1-4Galβ1-4Glc; GalNAcβ1-3Galα1-4Galβ1-4Glc; GalNAcα1-3GalNAcβ1-3Galα1-4Galβ1-4Glc; or GalNAcβ1-3GalNAcβ1-3Galα1-4Galβ1-4Glc.

When F is a glycotope, L is a glycerophospholipid and $S_2$ is selected from the group including: —CO(CH$_2$)$_3$CO—, —CO(CH$_2$)$_4$CO— (adipate), —CO(CH$_2$)$_5$CO— and —CO(CH$_2$)$_5$NHCO(CH$_2$)$_5$CO—, preferably $S_1$ is a $C_{3-5}$-aminoalkyl selected from the group consisting of: 3-aminopropyl, 4-aminobutyl, or 5-aminopentyl. More preferably $S_1$ is 3-aminopropyl.

In a second embodiment F is a molecule that mediates a cell-cell or cell-surface interaction. Preferably F is carbohydrate with an affinity for a component expressed on a targeted cell or surface. More preferably F has an affinity for a component expressed on epithelial cells or extra-cellular matrices. Yet more preferably F has an affinity for a component expressed on the epithelial cells or the extra-cellular matrix of the endometrium. Most preferably the component expressed on the epithelial cells or the extra-cellular matrix of the endometrium can be a naturally expressed component or an exogenously incorporated component.

In a third embodiment F is a molecule that mediates a cell-solute interaction. Preferably F is a ligand for a binding molecule where the presence of the binding molecule is diagnostic for a pathological condition. More preferably F is a ligand for an antibody (immunoglobulin).

In specific embodiments the water soluble synthetic molecule construct has the structure:

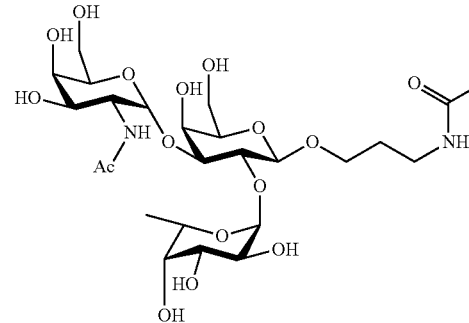
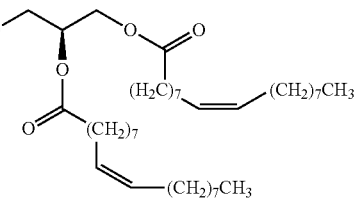

designated A$_{tri}$-sp-Ad-DOPE (I); the structure:

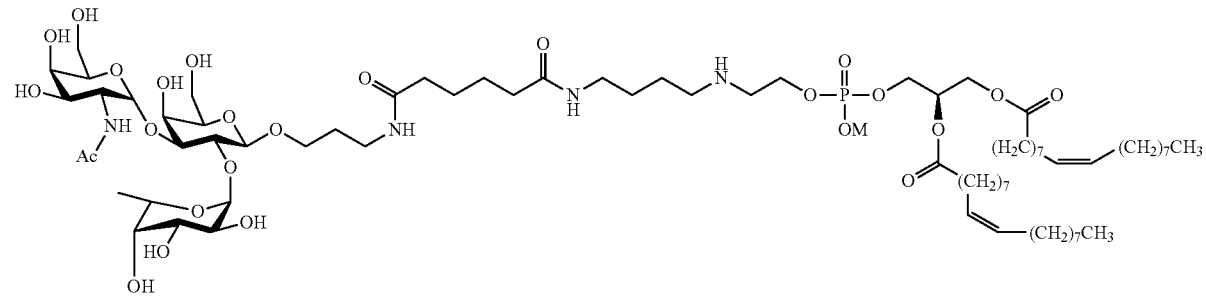

designated A*tri*-spsp$_1$-Ad-DOPE (II); the structure:
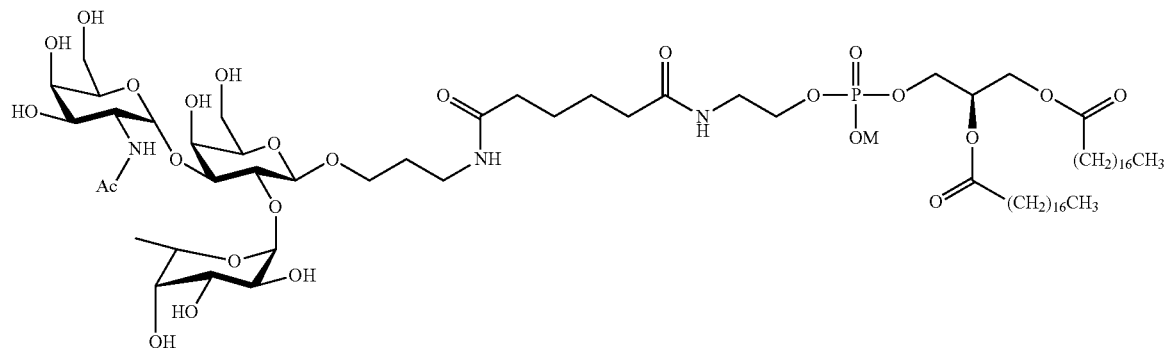
designated A*tri*-sp-Ad-DSPE (III); the structure
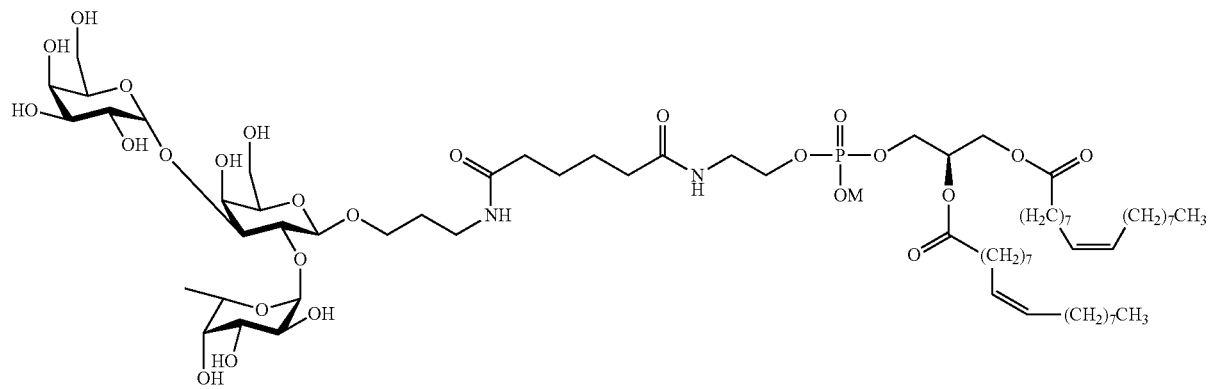
designated B*tri*-sp-Ad-DOPE (VI); the structure:
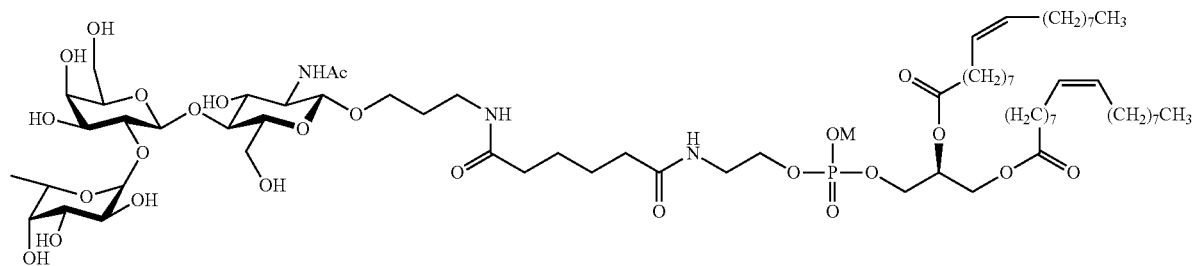
designated H*tri*-sp-Ad-DOPE (VII); the structure:
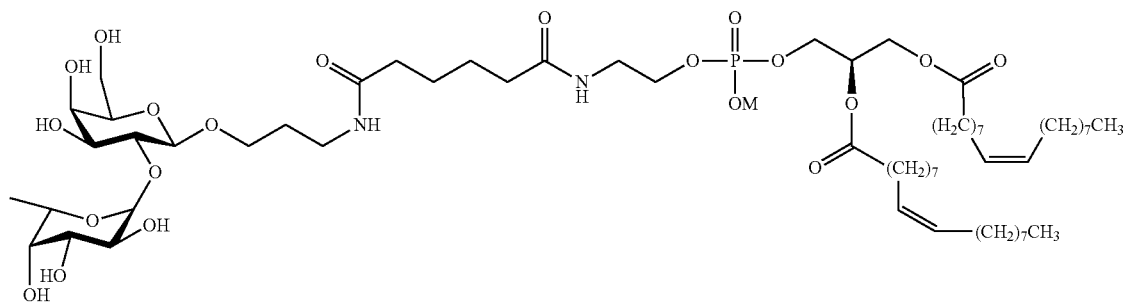

designated H$_{di}$-sp-Ad-DOPE (VIII); the structure:

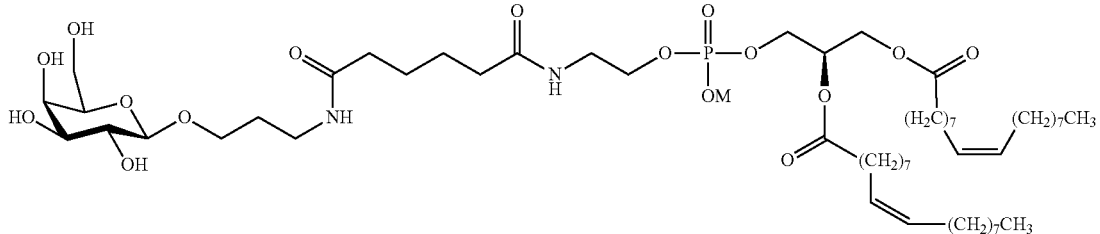

designated Galβ$_t$-sp-Ad-DOPE (IX); the structure:

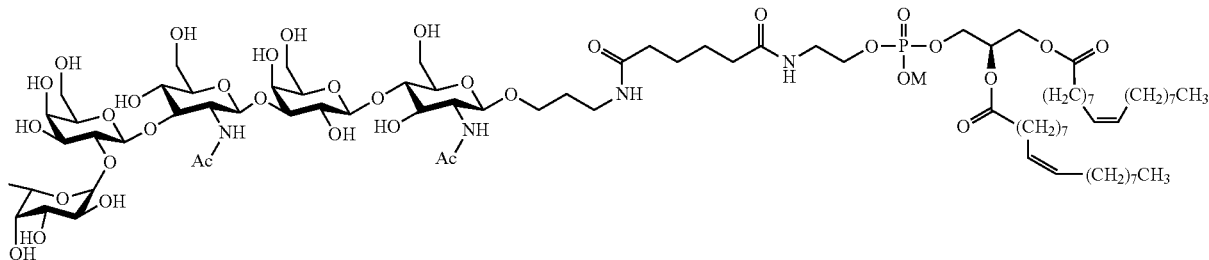

designated Fucα1-2Galβ1-3GlcNAcβ1-3Galβ1-4GlcNAc-sp-Ad-DOPE (XII); or the structure:

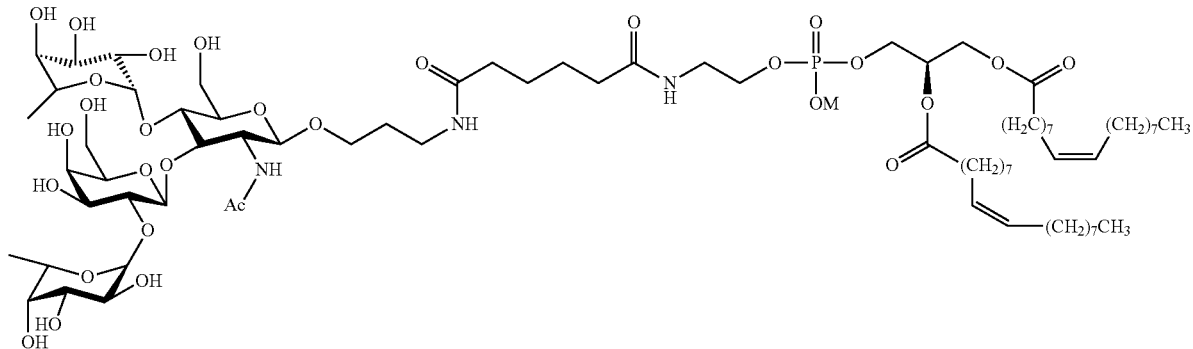

designated Fucα1-2Galβ1-3(Fucα1-4)GlcNAc-sp-Ad-DOPE (XIII).

M is typically H, but may be replaced by another monovalent cation such as Na$^+$, K$^+$ or NH$_4^+$.

In a third aspect the invention consists in a water soluble synthetic membrane anchor or synthetic molecule construct prepared by a method according to the second aspect of the invention.

In a fourth aspect the invention consists in a method of effecting qualitative and/or quantitative changes in the surface antigens expressed by a cell or multi-cellular structure including the step:

1. Contacting a suspension of the cell or multi-cellular structure with a synthetic membrane anchor or synthetic molecule construct according to the first aspect or third aspect of the invention for a time and at a temperature sufficient to effect the qualitative and/or quantitative change in the surface antigens expressed by the cell or multi-cellular structure.

Preferably the cell or multi-cellular structure is of human or murine origin.

Preferably the concentration of the water soluble synthetic membrane anchor or synthetic molecule construct in the suspension is in the range 0.1 to 10 mg/mL.

Preferably the temperature is in the range 2 to 37° C. More preferably the temperature is in the range 2 to 25° C. Most preferably the temperature is in the range 2 to 4° C.

In a first embodiment the cell is a red blood cell.

In this embodiment preferably F is selected from the group of glycotopes comprising the terminal sugars GalNAcα1-3 (Fucα1-2)Galβ; Galα1-3Galβ; Galβ; Galα1-3(Fucα1-2)Galβ; NeuAcα2-3Galβ; NeuAcα2-6Galβ; Fucα1-2Galβ; Galβ1-4GlcNAcβ1-6(Galβ1-4GlcNAcβ1-3)Galβ; Fucα1-2Galβ1-4GlcNAcβ1-6(Fucα1-2Galβ1-4GlcNAcβ1-3)Galβ; Fucα1-2Galβ1-4GlcNAcβ1-6(NeuAcα2-3Galβ1-4GlcNAcβ1-3)Galβ; NeuAcα2-3Galβ1-4GlcNAcβ1-6(NeuAcα2-3Galβ1-4GlcNAcβ1-3)Galβ; Galα1-4Galβ1-4Glc; GalNAcβ1-3Galα1-4Galβ1-4Glc; GalNAcα1-

3GalNAcβ1-3Galα1-4Galβ1-4Glc; or GalNAcβ1-3GalNAcβ1-3Galα1-4Galβ1-4Glc. More preferably F is selected from the group of glycotopes consisting of the oligosaccharides GalNAcα1-3(Fucα1-2)Galβ and Galα1-3(Fucα1-2)Galβ.

Preferably the synthetic molecule construct is selected from the group including: $A_{tri}$-sp-Ad-DOPE (I); $A_{tri}$-spsp$_1$-Ad-DOPE (II); $A_{tri}$-sp-Ad-DSPE (III); $B_{tri}$-sp-Ad-DOPE (VI); $H_{tri}$-sp-Ad-DOPE (VII); $H_{di}$-sp-Ad-DOPE (VIII); Galβ$_i$-sp-Ad-DOPE (IX); Fucα1-2Galβ1-3GlcNAcβ1-3Galβ1-4GlcNAc-sp-Ad-DOPE (XII); and Fucα1-2Galβ1-3(Fucα1-4)GlcNAc-sp-Ad-DOPE (XIII).

In a second embodiment the multi-cellular structure is an embryo.

In this embodiment preferably F is an attachment molecule where the attachment molecule has an affinity for a component expressed on the epithelial cells or the extra-cellular matrix of the endometrium.

The component expressed on the epithelial cells or the extra-cellular matrix of the endometrium can be a naturally expressed component or an exogenously incorporated component.

Preferably the synthetic membrane anchor or synthetic molecule construct is selected from the group including: $A_{tri}$-sp-Ad-DOPE (I); $A_{tri}$-spsp$_1$-Ad-DOPE (II); $A_{tri}$-sp-Ad-DSPE (III); $B_{tri}$-sp-Ad-DOPE (VI); $H_{tri}$-sp-Ad-DOPE (VII); $H_{di}$-sp-Ad-DOPE (VIII); Galβ$_i$-sp-Ad-DOPE (IX); Fucα1-2Galβ1-3GlcNAcβ1-3Galβ1-4GlcNAc-sp-Ad-DOPE (XII); and Fucα1-2Galβ1-3(Fucα1-4)GlcNAc-sp-Ad-DOPE (XIII).

In a third embodiment the cell is red blood cell.

In this embodiment preferably F is a ligand for a binding molecule where the presence of the binding molecule is diagnostic for a pathological condition. More preferably F is a ligand for an antibody (immunoglobulin).

In a fifth aspect the invention consists in a cell or multi-cellular structure incorporating a water soluble synthetic membrane anchor or synthetic molecule construct according to the first or third aspect of the invention.

Preferably the cell or multi-cellular structure is of human or murine origin.

In a first embodiment the cell is a red blood cell incorporating a water soluble synthetic membrane anchor or synthetic molecule construct selected from the group including: $A_{tri}$-sp-Ad-DOPE (I); $A_{tri}$-spsp$_1$-Ad-DOPE (II); $A_{tri}$-sp-Ad-DSPE (III); $B_{tri}$-sp-Ad-DOPE (VI); $H_{tri}$-sp-Ad-DOPE (VII); $H_{di}$-sp-Ad-DOPE (VIII); Galβ$_i$-sp-Ad-DOPE (IX); Fucα1-2Galβ1-3GlcNAcβ1-3Galβ1-4GlcNAc-sp-Ad-DOPE (XII); and Fucα1-2Galβ1-3(Fucα1-4)GlcNAc-sp-Ad-DOPE (XIII).

In a second embodiment the multi-cellular structure is an embryo incorporating a water soluble synthetic membrane anchor or synthetic molecule construct selected from the group consisting of: $A_{tri}$-sp-Ad-DOPE (I); $A_{tri}$-spsp$_1$-Ad-DOPE (II); $A_{tri}$-sp-Ad-DSPE (III); $B_{tri}$-sp-Ad-DOPE (VI); $H_{tri}$-sp-Ad-DOPE (VII); $H_{di}$-sp-Ad-DOPE (VIII); Galβ$_i$-sp-Ad-DOPE (IX); Fucα1-2Galβ1-3GlcNAcβ1-3Galβ1-4GlcNAc-sp-Ad-DOPE (XII); and Fucα1-2Galβ1-3(Fucα1-4)GlcNAc-sp-Ad-DOPE (XIII).

In a sixth aspect the invention consists in a kit comprising a dried preparation or solution of a water soluble synthetic membrane anchor or synthetic molecule construct according to the first or third aspect of the invention.

Preferably the synthetic membrane anchor or water soluble synthetic molecule construct according to the first or third aspect of the invention is selected from the group consisting of: $A_{tri}$-sp-Ad-DOPE (I); $A_{tri}$-spsp$_1$-Ad-DOPE (II); $A_{tri}$-sp-Ad-DSPE (III); $B_{tri}$-sp-Ad-DOPE (VI); $H_{tri}$-sp-Ad-DOPE (VII); $H_{di}$-sp-Ad-DOPE (VIII); Galβ$_i$-sp-Ad-DOPE (IX); Fucα1-2Galβ1-3GlcNAcβ1-3Galβ1-4GlcNAc-sp-Ad-DOPE (XII); and Fucα1-2Galβ1-3(Fucα1-4)GlcNAc-sp-Ad-DOPE (XIII).

In an seventh aspect the invention consists in a kit comprising a suspension in a suspending solution of cells or multi-cellular structures according to the fifth aspect of the invention.

Preferably the suspending solution is substantially free of lipid.

Preferably the cell or multi-cellular structure is of human or murine origin.

Preferably the cells are red blood cells that do not naturally express A- or B-antigen and incorporate a water soluble synthetic membrane anchor or synthetic molecule construct selected from the group consisting of: $A_{tri}$-sp-Ad-DOPE (I); $A_{tri}$-spsp$_1$-Ad-DOPE (II); $A_{tri}$-sp-Ad-DSPE (III); $B_{tri}$-sp-Ad-DOPE (VI); $H_{tri}$-sp-Ad-DOPE (VII); $H_{di}$-sp-Ad-DOPE (VIII); Galβ$_i$-sp-Ad-DOPE (IX); Fucα1-2Galβ1-3GlcNAcβ1-3Galβ1-4GlcNAc-sp-Ad-DOPE (XII); and Fucα1-2Galβ1-3(Fucα1-4)GlcNAc-sp-Ad-DOPE (XIII). More preferably the cells are sensitivity controls.

In a eighth aspect the invention consists in a pharmaceutical preparation comprising a dried preparation or solution of a water soluble synthetic membrane anchor or synthetic molecule construct according to the first or fourth aspect of the invention.

Preferably the pharmaceutical preparation is in a form for administration by inhalation.

Preferably the pharmaceutical preparation is in a form for administration by injection.

In an ninth aspect the invention consists in a pharmaceutical preparation comprising cells or multi-cellular structures according to the fifth aspect of the invention.

Preferably the cells or multi-cellular structures are of human or murine origin.

Preferably the pharmaceutical preparation is in a form for administration by inhalation.

Preferably the pharmaceutical preparation is in a form for administration by injection.

DETAILED DESCRIPTION

The synthetic molecule constructs of the invention spontaneously and stably incorporate into a lipid bi-layer, such as a membrane, when a solution of the molecule is contacted with the lipid bi-layer. Whilst not wishing to be bound by theory it is believed that the insertion into the membrane of the lipid tails of the lipid (L) is thermodynamically favoured. Subsequent disassociation of the synthetic molecule construct from the lipid membrane is believed to be thermodynamically unfavoured. Surprisingly, the synthetic molecule constructs identified herein have also been found to be water soluble.

The synthetic molecule constructs of the invention are used to transform cells resulting in qualitative and/or quantitative changes in the surface antigens expressed. It will be recognised that the transformation of cells in accordance with the invention is distinguished from transformation of cells by genetic engineering. The invention provides for phenotypic transformation of cells without genetic transformation.

In the context of this description the term "transformation" in reference to cells is used to refer to the insertion or incorporation into the cell membrane of exogenously prepared synthetic molecule constructs thereby effecting qualitative and quantitative changes in the cell surface antigens expressed by the cell.

The synthetic molecule constructs of the invention comprise an antigen (F) linked to a lipid portion (or moiety) (L) via a spacer ($S_1$-$S_2$). The synthetic molecule constructs can be prepared by the condensation of a primary aminoalkyl, secondary aliphatic aminoalkyl or primary aromatic amine derivative of the antigen with an activated lipid. Methods of preparing neoglycoconjugates have been reviewed (Bovin, N. Biochem. Soc. Symp., 69, 143-160).

A desired phenotypic transformation may be achieved using the synthetic molecule constructs of the invention in a one step method or a two step method. In the one step method the water soluble synthetic molecule construct (F—$S_1$-$S_2$-L) comprises the surface antigen as F.

In the two step method the synthetic molecule construct (F—$S_1$-$S_2$-L) comprises an antigen (F) that serves as a functional group to which a surface antigen can be linked following insertion of the synthetic molecule construct into the membrane. The functional group can be a group such as a lectin, avidin or biotin. When used in the two step method the synthetic molecule construct is acting as a synthetic membrane anchor.

In accordance with the invention the primary aminoalkyl, secondary aliphatic aminoalkyl or primary aromatic amine and the activator of the lipid are selected to provide a synthetic molecule construct that is water soluble and will spontaneously and stably incorporate into a lipid bi-layer when a solution of the synthetic molecule construct is contacted with the lipid bi-layer.

In the context of this description the phrase "water soluble" means a stable, single phase system is formed when the synthetic molecule construct is contacted with water or saline (such as PBS) in the absence of organic solvents or detergents, and the term "solution" has a corresponding meaning.

In the context of this description the phrase "stably incorporate" means that the synthetic molecule constructs incorporate into the lipid bi-layer or membrane with minimal subsequent exchange between the lipid bi-layer or membrane and the external aqueous environment of the lipid bi-layer or membrane.

The selection of the primary aminoalkyl, secondary aliphatic aminoalkyl or primary aromatic amine and the activator depends on the physico-chemical properties of the antigen (F) to be linked to the lipid (L).

It will be understood by those skilled in the art that for a non-specific interaction, such as the interaction between a diacyl- or dialkyl-glycerolipid and a membrane, structural and stereo-isomers of naturally occurring lipids can be functionally equivalent. For example, it is contemplated by the inventors that diacylglycerol 2-phosphate could be substituted for phosphatidate (diacylglycerol 3-phosphate). Furthermore it is contemplated by the inventors that the absolute configuration of phosphatidate can be either R or S.

The inventors have determined that to prepare synthetic molecule constructs of the invention where the antigen (F) is an oligosaccharide selected from the group of glycotopes for A-, B- and H-antigens of the ABO blood groups, the primary aminoalkyl, secondary aliphatic aminoalkyl or primary aromatic amine, and the activator should be selected to provide a spacer ($S_1$-$S_2$) with a structure according to one of those presented here:

Alternative structures of $S_1$-$S_2$ for a water soluble synthetic molecule construct (F-$S_1$-$S_2$-L) where F is a carbohydrate (or other antigen) with similar physico-chemical properties to the carbohydrate portion of the A-, B- or H-antigens of the ABO blood groups and L is a glycerophospholipid (n, m independently = 2 to 5)

| $S_1$ is selected from: | $S_2$ is selected from: |
|---|---|
| —O($CH_2$)nNH— | —CO($CH_2$)$_n$CO— |
| | or |
| | —CO($CH_2$)$_m$NHCO($CH_2$)$_n$CO— |

It will be understood by one skilled in the art that once the structure of the spacer ($S_1$-$S_2$) has been determined for a given class of antigens, the same structure of the spacer can be adopted to prepare synthetic molecule constructs of other classes of antigen with similar physico-chemical properties.

For example, the structure of the spacer for synthetic molecule constructs (F—$S_1$-$S_2$-L) where F is a glycotope of the A-, B- and H-antigens of the ABO blood groups, may be the structure of the spacer selected to prepare synthetic molecule constructs of other antigens with physico-chemical properties similar to the glycotopes of the A-, B- and H-antigens of the ABO blood groups.

In principle the glycotope of a broad range of blood group related glycolipids or glycoproteins could be the antigen (F) of the synthetic molecule construct F—$S_1$-$S_2$-L where $S_1$-$S_2$-L is identical or equivalent to the corresponding portion of the synthetic molecule constructs designated $A_{tri}$-sp-Ad-DOPE (I), $A_{tri}$-sps$p_1$-Ad-DOPE (II), $A_{tri}$-sp-Ad-DSPE (III), $B_{tri}$-sp-Ad-DOPE (VI), $H_{tri}$-sp-Ad-DOPE (VII), $H_{di}$-sp-Ad-DOPE (VIII), Galβ-sp-Ad-DOPE (IX), Fucα1-2Galβ1-3GlcNAcβ1-3Galβ1-4GlcNAc-sp-Ad-DOPE (XII), and Fucα1-2Galβ1-3(Fucα1-4)GlcNAc-sp-Ad-DOPE (XIII).

The structures of known blood group-related glycolipids and glycoproteins (see references) are provided in the following list:

Glycolipids*

(*In general, for almost all examples of A-antigens the terminal A sugar GalNAc can be replaced with the B sugar Gal. Additionally, the lack of either the A or B determinant creates the equivalent H determinant.)

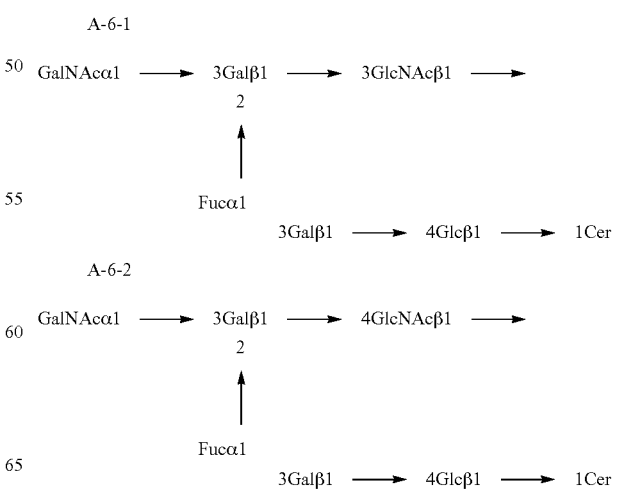

A-7-2 (ALe^y)
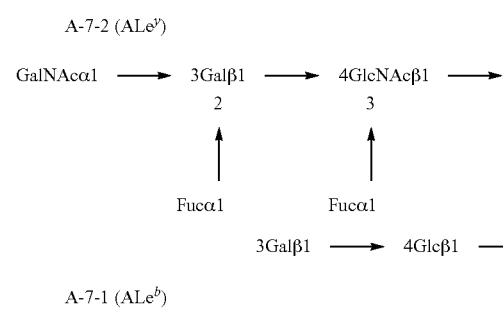
A-7-1 (ALe^b)
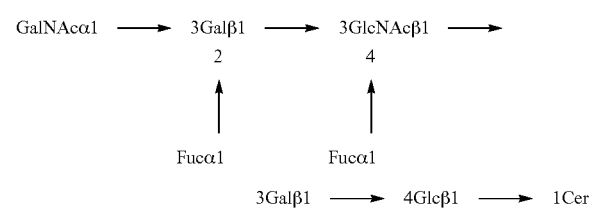
A-7-4
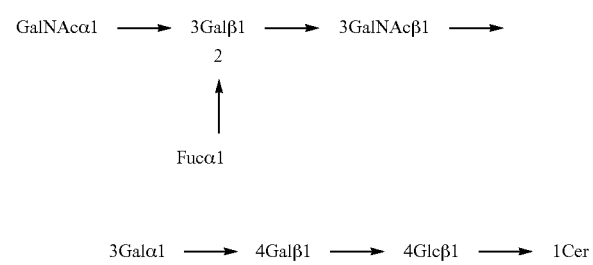
A-8-2
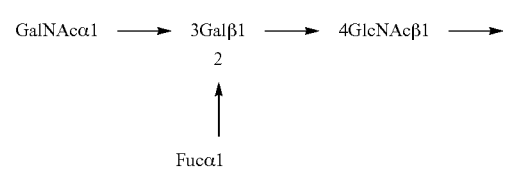
A-9-3
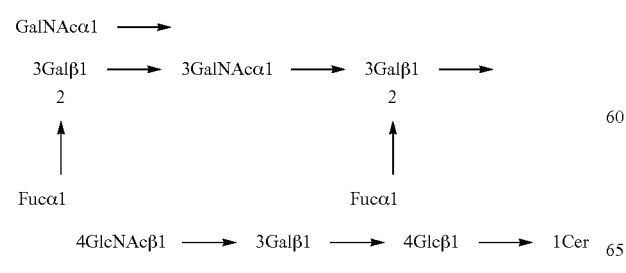
A-12-2
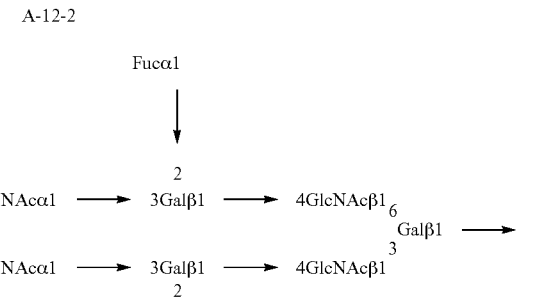
A-14-2
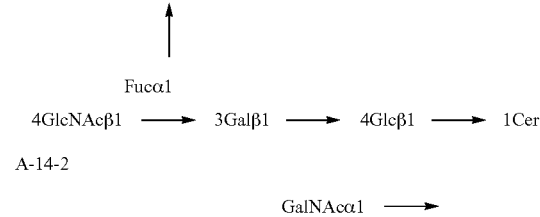
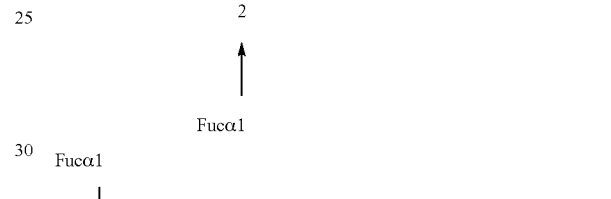
A-16-2
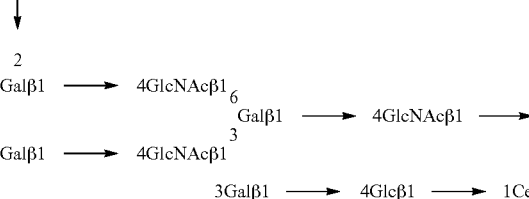
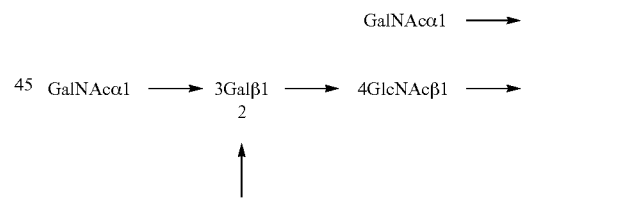
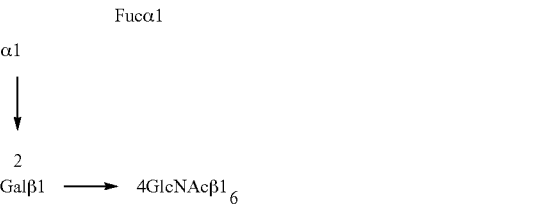
Lactosylceramide
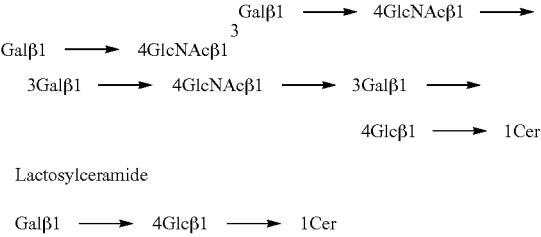

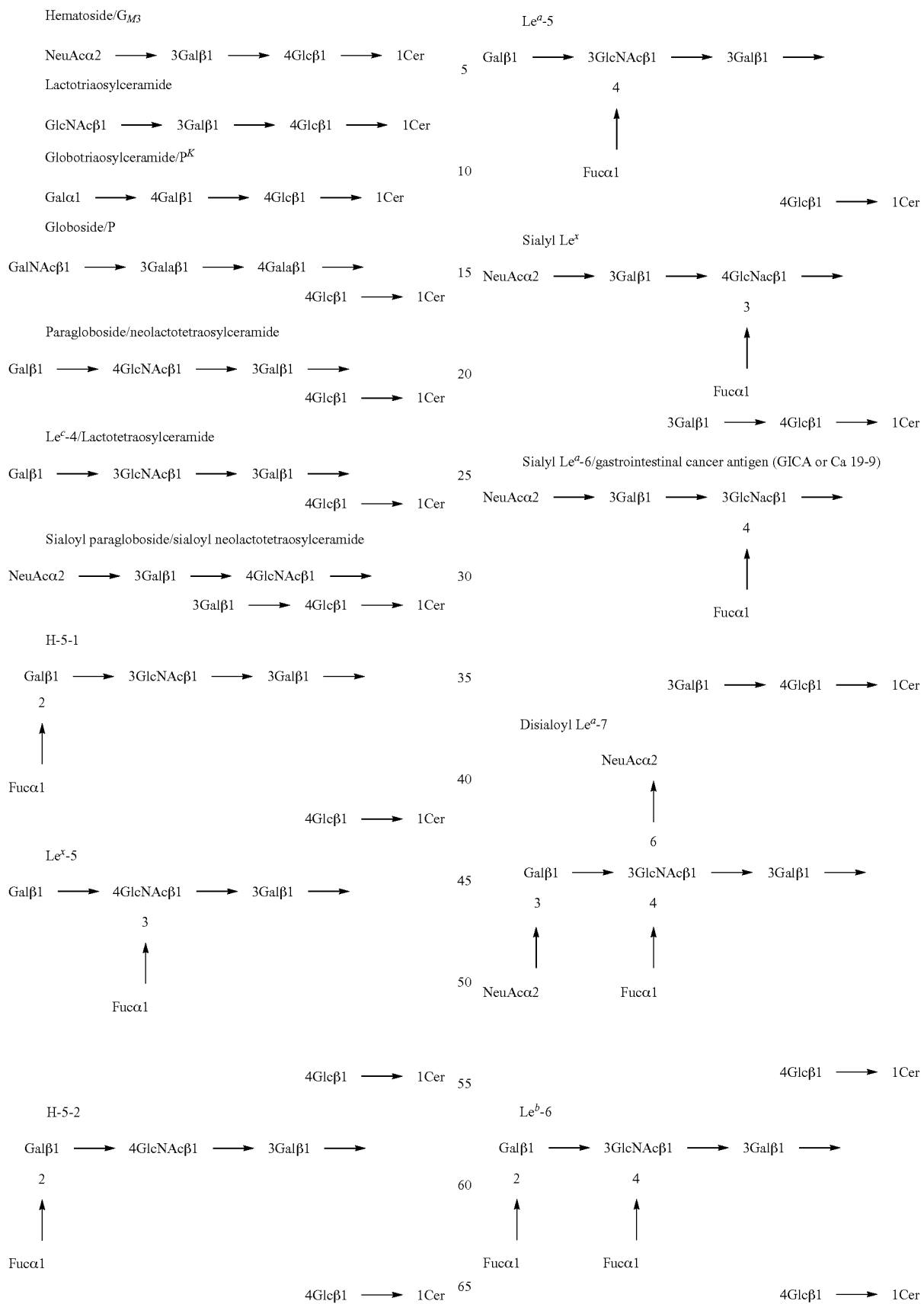

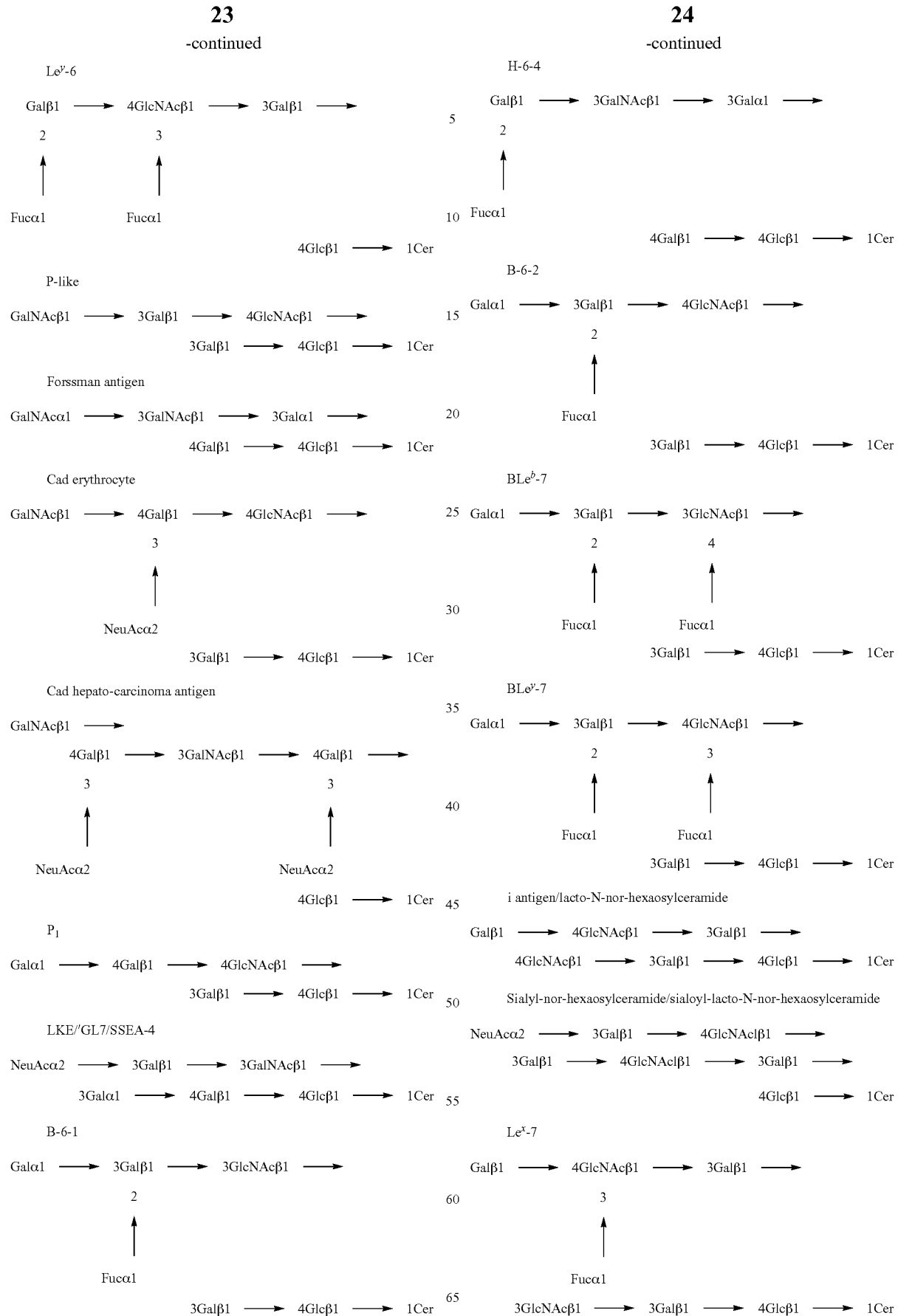

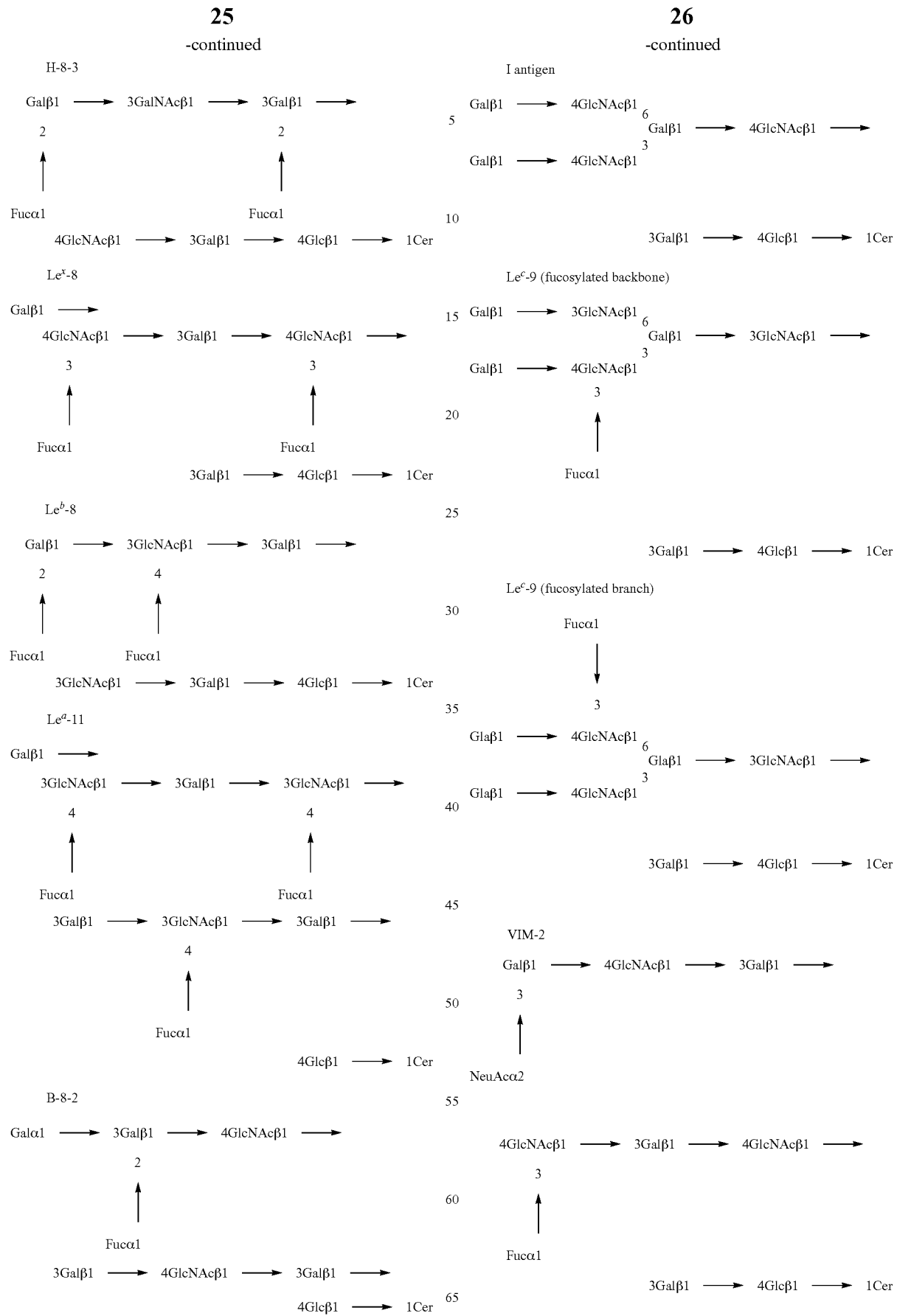

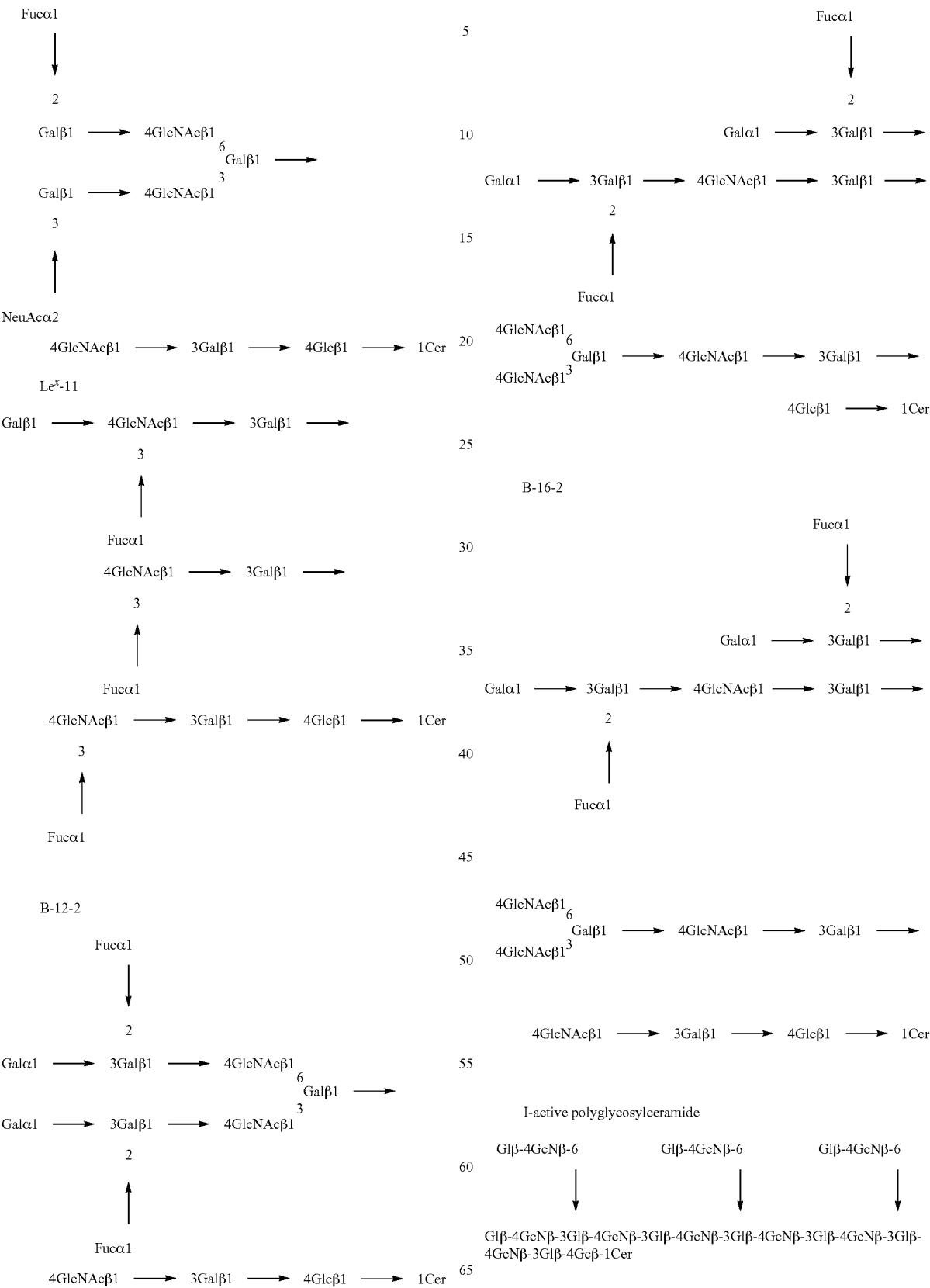

O-Linked Glycoproteins
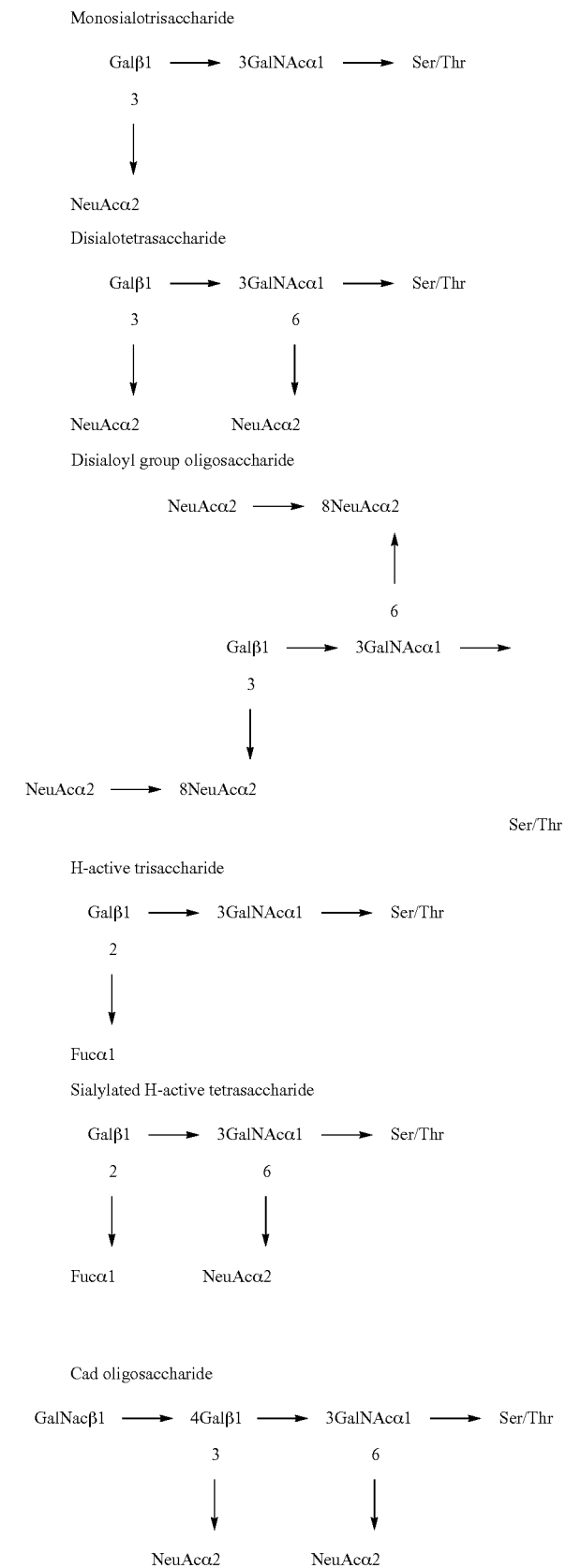

-continued
GlcNAc oligosaccharide
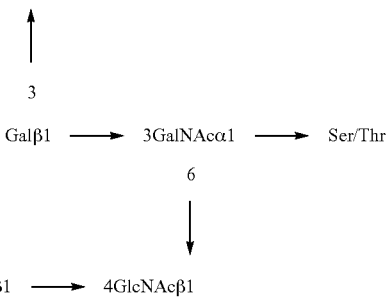
Mucin oligosaccharide/A-active glycoprotein
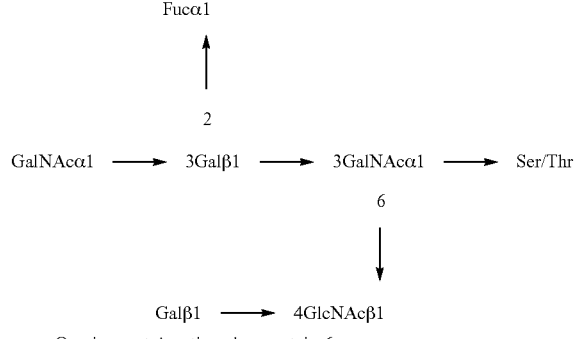
Ovarian cyst A-active glycoprotein-6a
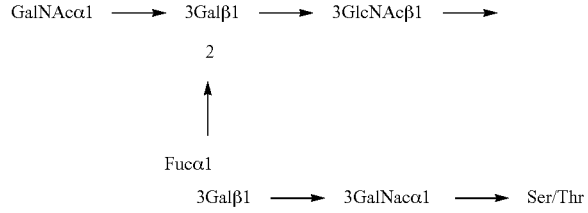
Ovarian cyst A-active glycoprotein-6b
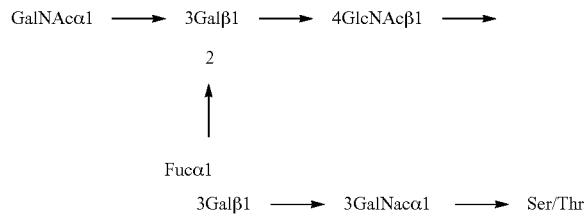
Ovarian cyst Le$^a$-active glycoprotein-7
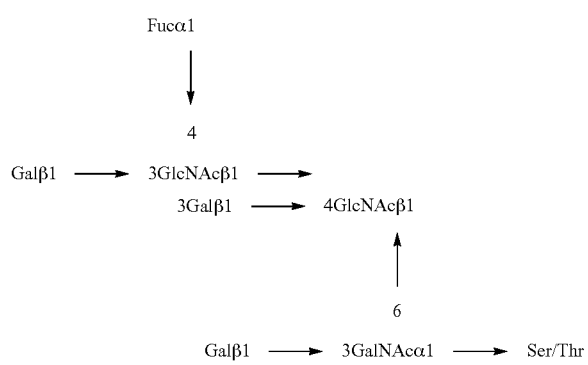

-continued
Ovarian cyst Le^a-active glycoprotein-10
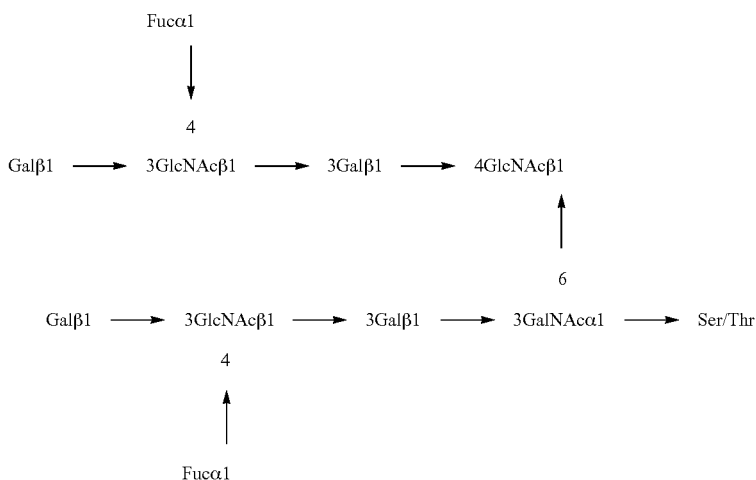
Ovarian cyst A-active glycoprotein-18
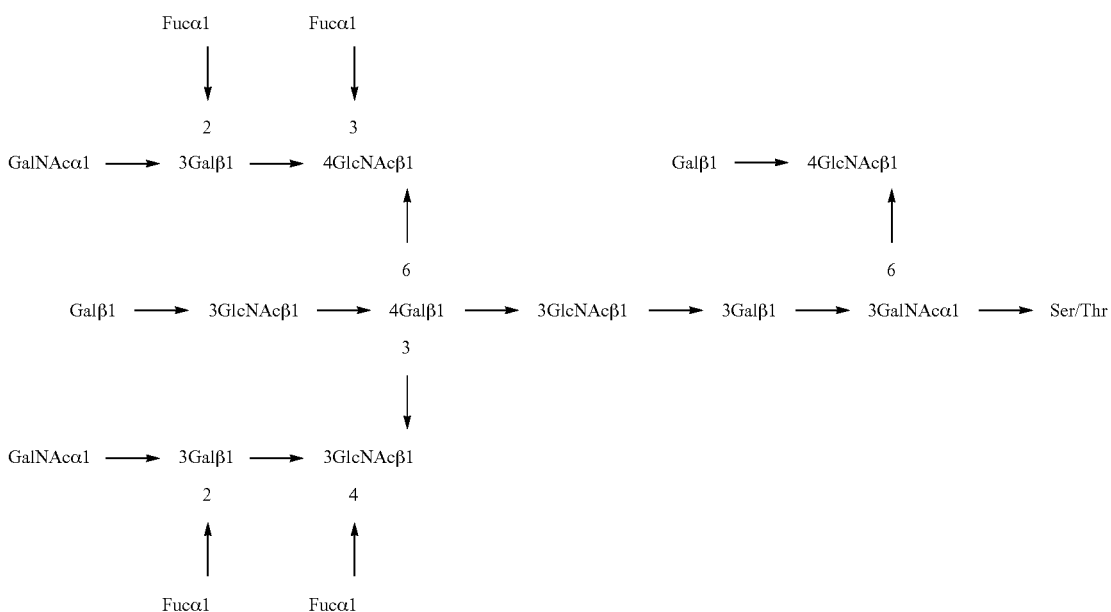
N-Linked Glycoproteins
Complex type/Alkali-stable chain
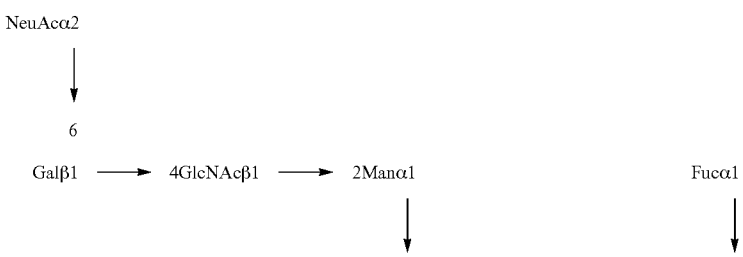

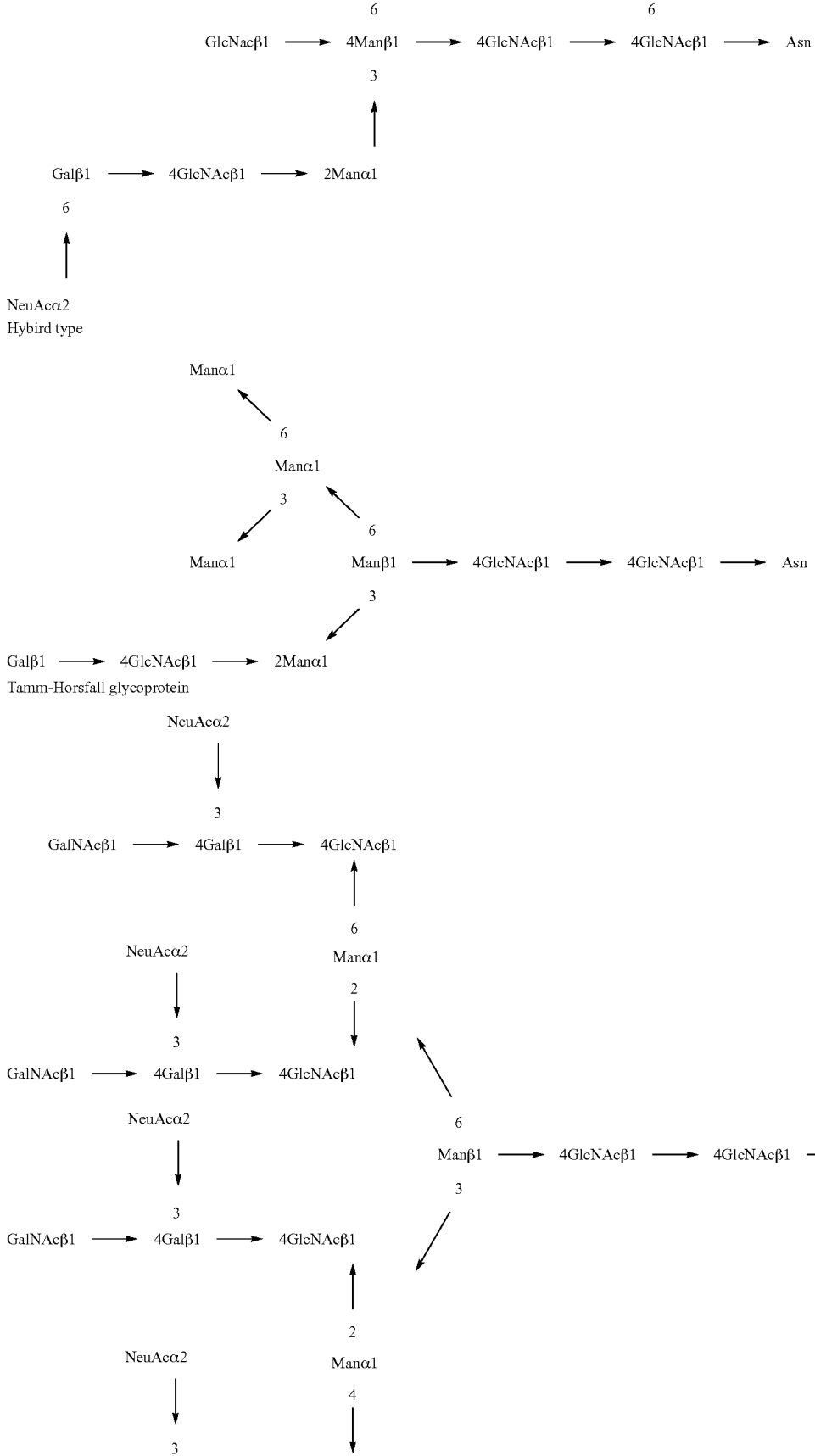

GalNAcβ1 ⟶ 4Galβ1 ⟶ 4GlcNAcβ1
High-mannose type
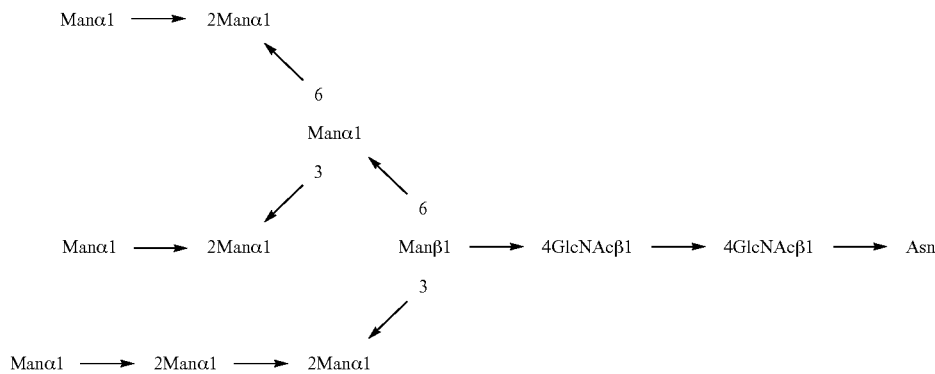
Disialyl foetal erythrocyte antigen
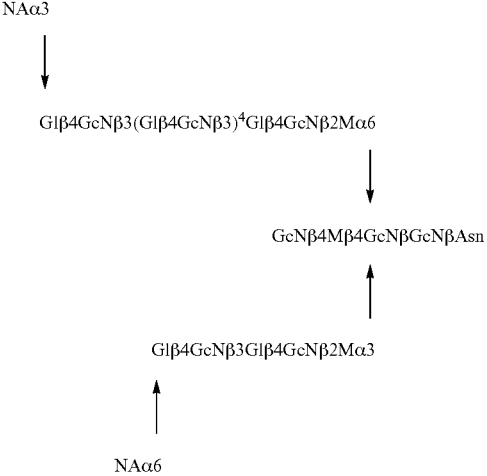
Trisialoyl foetal erythrocyte antigen (disialoyl group on branch)
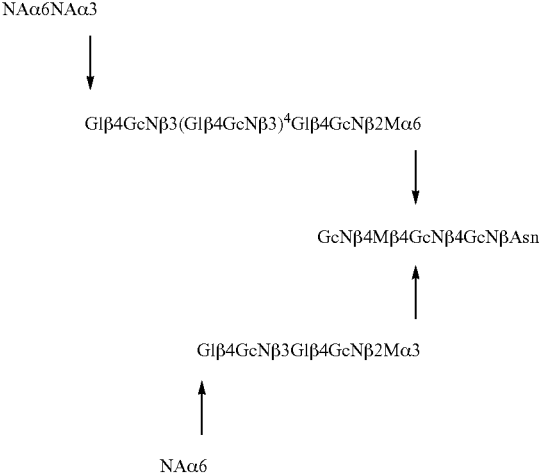

-continued

Monofucosyl-monosialyl foetal erythrocyte antigen (fucosylated backbone)

NAα3
Glβ4GcNβ3(Glβ4GcNβ3)⁴Glβ4GcNβ2Mα6
GcNβ4Mβ4GcNβ4GcNβAsn
Glβ4GcNβ3Glβ4GcNβ2Mα3
Fα2

Monofucosyl-monosialyl foetal erythrocyte antigen (fucosylated branch)

Fα2
Glβ4GcNβ3(Glβ4GcNβ3)⁴Glβ4GcNβ2Mα6
GcNβ4Mβ4GcNβ4GcNβAsn
Glβ4GcNβ3Glβ4GcNβ2Mα3
NAα6

Monofucosyl-disialyl foetal erythrocyte antigen (disialyl group on branch)

NAα6NAα3
Glβ4GcNβ3(Glβ4GcNβ3)⁴Glβ4GcNβ2Mα6
GcNβ4Mβ4GcNβ4GcNβAsn
Glβ4GcNβ3Glβ4GcNβ2Mα3
Fα2

Difucosyl foetal erythrocyte antigen

Fα2
↓
Glβ4GcNβ3(Glβ4GcNβ3)⁴Glβ4GcNβ2Mα6
↓
GcNβ4Mβ4GcNβ4GcNβAsn
↑
Glβ4GcNβ3Glβ4GcNβ2Mα3
↑
Fα2

Foetal lactosaminoglycan (GlcNAcβ1 ⟶ 3Galβ1 ⟶ 4)⁶GlcNAcβ1 ⟶ 2Manα1
↓
6
Galβ1 ⟶ 4GlcNAcβ1 ⟶ 4Manβ1 ⟶
3
↓
Galβ1 ⟶ 4GlcNAcβ1 ⟶ 3Galβ1 ⟶ 4GlcNAcβ1 ⟶ 2Manα1

4GlcNAcβ1 ⟶ 4GlcNAcβ1 ⟶ Asn

Adult lactosaminoglycan

Glβ4GcNβ6    Glβ4GcNβ6    Glβ4GcNβ6
↓            ↓            ↓
(Glβ4GcNβ3)²Glβ4(GcNβ3Glβ4)²GcNβ3Glβ4GcNβ3Glβ4GcNβ3Glβ4GcNβ3Glβ4GcNβ2Mα6
↓
Glβ4GcNβ4Mβ4GcNβ4GcNβAsn
↑
Glβ4GcNβ3Glβ4GcNβ3Glβ4GcNβ3Glβ4GcNβ2Mα3
↑           ↑
GcNβ6    GcNβ6
↑           ↑
Glβ4      Glβ4

Monofucosyl-monosialoyl adult erythrocyte antigen
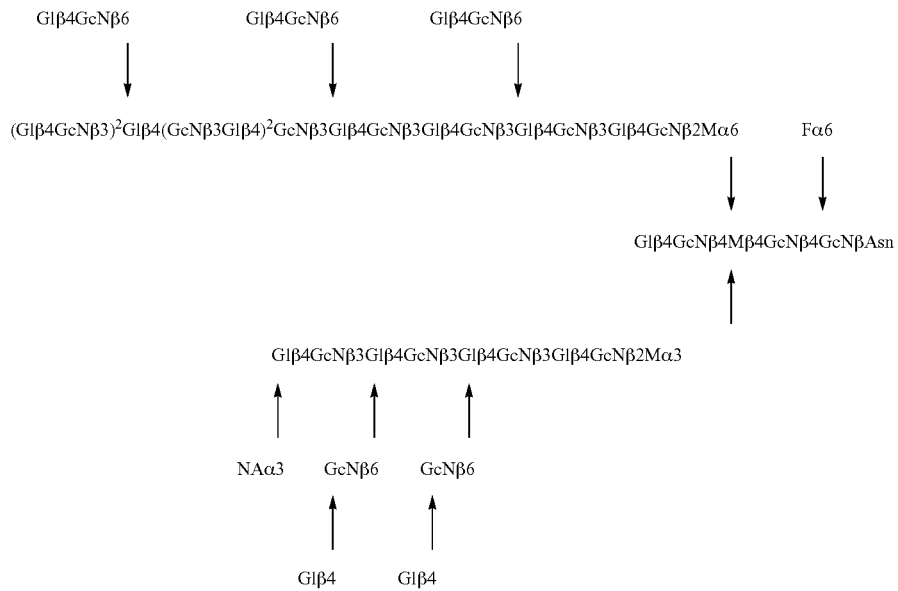
Monofucosyl-monosialoyl adult erythrocyte antigen
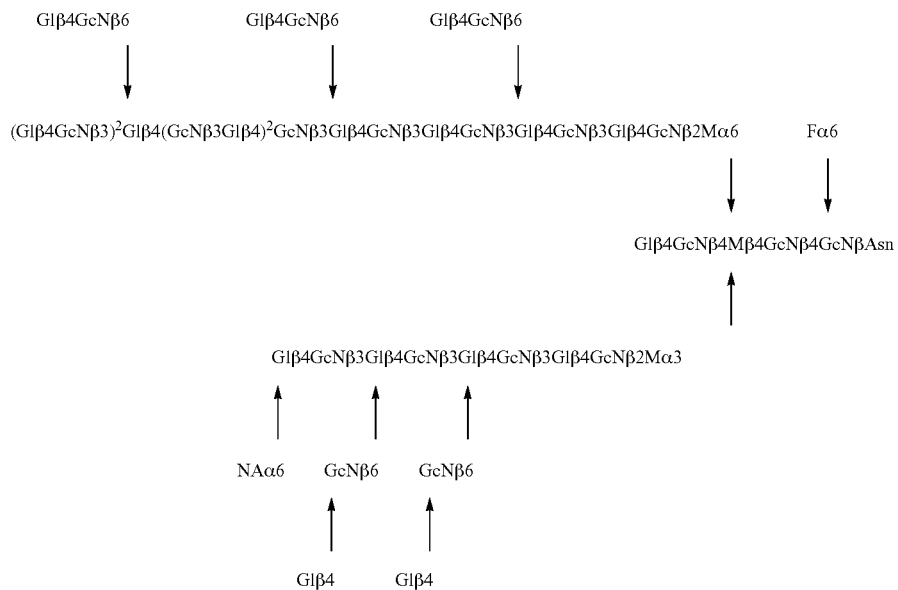

Difucosyl adult erythrocyte antigen

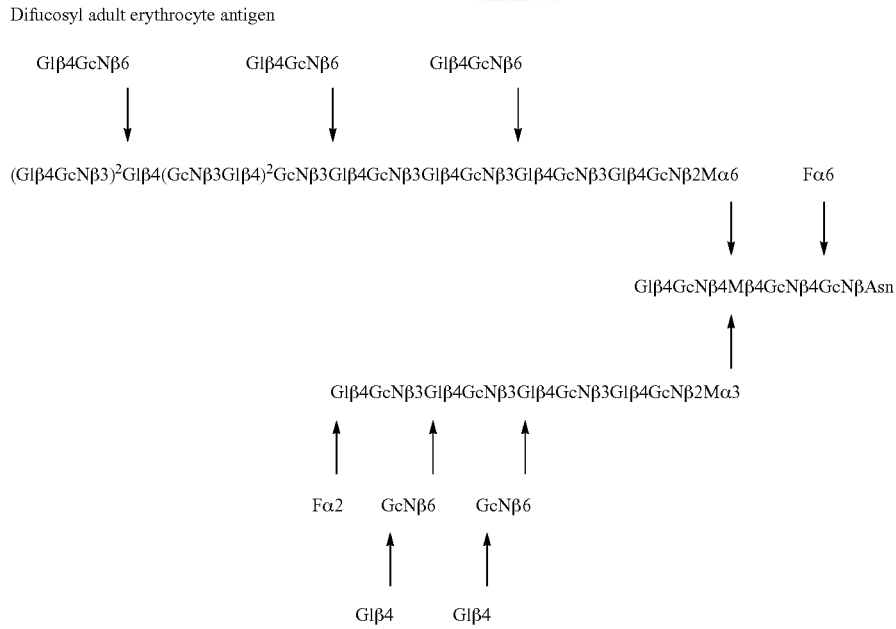

Key: Gl = D-Gal, Gc = D-Glc, GcN = D-GlcNac, M = D-Man, F = L-Fuc, NA = NeuAc.

It will be understood by those skilled in the art that the synthetic molecule constructs ($F$—$S_1$-$S_2$-L) of the invention where F is an oligosaccharide may be used as "synthetic glycolipids" and substituted for glycolipids obtained from biological (botanical or zoological) sources.

In the context of this description of the invention the term "glycolipid" means a lipid containing carbohydrate of amphipathic character including: glycosylated glycerolipids, such as glycosylated phosphoglycerides and glycosylglycerides; glycosylated sphingolipids (neutral glycolipids) such as glycosylceramides or cerebrosides; and gangliosides (acidic glycolipids).

In the context of this description of the invention the phrase "glycolipid-linked antigen" means a lipid containing carbohydrate in which an antigen (e.g. a protein) is linked to the glycolipid via the carbohydrate portion of the molecule. Examples of glycolipid-linked antigens include GPI-linked proteins.

It will be understood by those skilled in the art that a glycolipid is itself an antigen. The term and phrase "glycolipid" and "glycolipid-linked antigen" are used to distinguish between naturally occurring molecules where the antigen is the glycolipid and naturally occurring molecules where the antigen is linked to the glycolipid via the carbohydrate portion of the glycolipid. By analogy the synthetic molecule constructs of the invention could be described as both "synthetic glycolipids" and synthetic membrane anchors to the extent that the antigen may be the synthetic glycolipid per se or attached to the synthetic glycolipid.

It will be understood by those skilled in the art that the carbohydrate portion of a glycolipid may be modified and linked to other antigens by the methods described in the specification accompanying the international application no. PCT/NZ2003/00059 (published as WO03087346).

In the context of this description of the invention the term "glycotope" is used to refer to the antigenic determinant located on the carbohydrate portion of a glycolipid. The classification of glycolipid antigens in blood group serology is based on the structure of the carbohydrate portion of the glycolipid.

In blood group serology it is known that the terminal sugars of the glycotopes of A-antigens are GalNAcα1-3(Fucα1-2)Galβ, and the terminal sugars of the glycotopes of the B-antigens are Galα1-3(Fucα1-2)Galβ. Incorporation into the membrane of RBCs of water soluble synthetic molecule constructs of the invention where F is GalNAcα1-3(Fucα1-2)Galβ or Galα1-3(Fucα1-2)Galβ provides RBCs that are serologically equivalent to A-antigen or B-antigen expressing RBCs, respectively.

The terminal three sugars of the carbohydrate portion of the naturally occurring A- or B-antigen are the determinant of the A and B blood groupings. The terminal four or five sugars of the carbohydrate portion of the naturally occurring A-antigen are the determinant of the A blood sub-groupings A type 1, A type 2, etc. Accordingly the RBCs incorporating the synthetic molecule constructs of the invention can be used to characterise and discriminate between blood typing reagents (antibodies) of differing specificity.

Water soluble synthetic molecule constructs of the invention that exclude a carbohydrate portion are contemplated by the inventors. Antigens other than carbohydrates or oligosaccharides, but with similar physico-chemical properties, may be substituted for F in the "synthetic glycolipids" described.

Synthetic molecule constructs of the invention that comprise an antigen (F) with differing physico-chemical properties to those of carbohydrates or oligosaccharides are also contemplated by the inventors. Water soluble synthetic molecule constructs comprising these antigens may be prepared by selecting different spacers.

The advantages provided by the synthetic molecule constructs of this invention will accrue when used in the practice of the inventions described in the specifications for the international application nos. PCT/N02/00212 (published as WO03/034074) and PCT/NZ03/00059 (published as WO03087346). The specifications accompanying these applications are incorporated herein by reference.

The synthetic molecule constructs overcome many of the limitations of using natural glycolipids in the practice of these inventions. A particular advantage of the synthetic molecule constructs is their superior performance and ability to be used in the transformation of cells at reduced temperatures, e.g. 4° C.

As described herein not all structures of the spacer ($S_1$-$S_2$) will provide a synthetic molecule construct (F—$S_1$-$S_2$-L) that is water soluble and spontaneously and stably incorporate in to a lipid bilayer such as a cell membrane. The synthetic molecule constructs designated $A_{tri}$-sp-lipid (IV) and Atri-PAA-DOPE (V) were determined not to be water soluble and/or unable to spontaneously and stably incorporate in to a lipid bilayer such as a cell membrane.

tom). (*—transformation solution (containing glycolipids) was not washed out after the incubation, it was left in over night and washed out the next day (day 2).)

(IV)

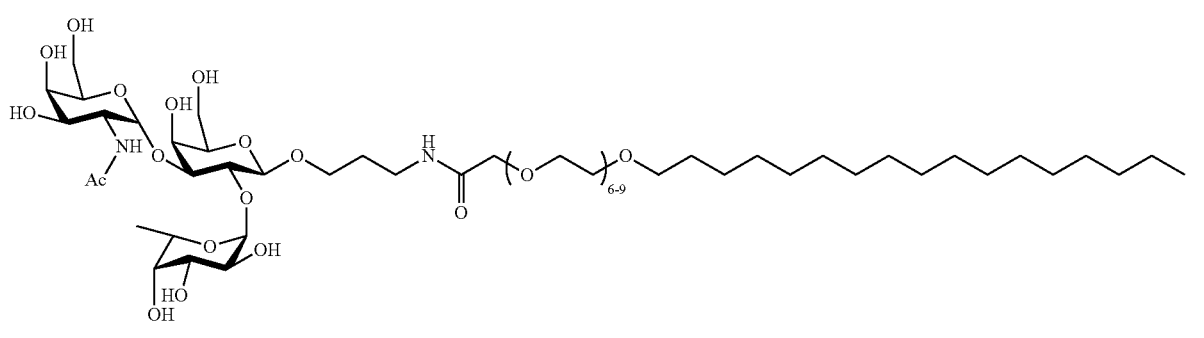

designated $A_{tri}$-sp-lipid (V)

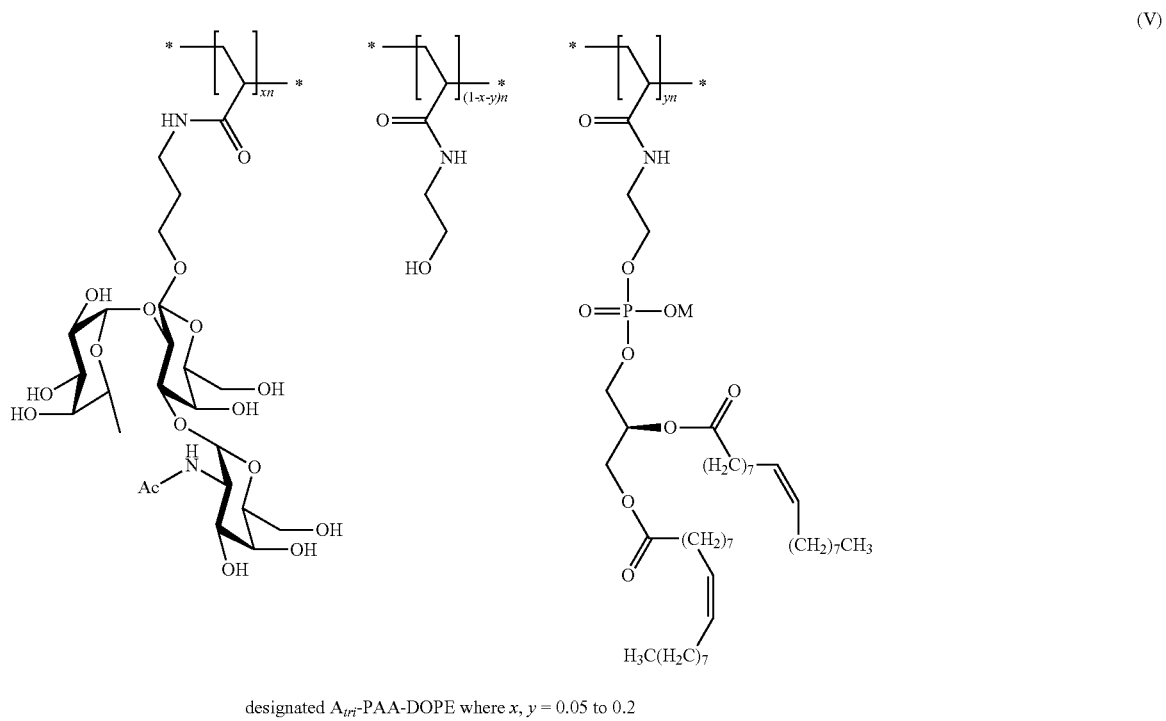

designated $A_{tri}$-PAA-DOPE where $x, y = 0.05$ to $0.2$

Figure 1:
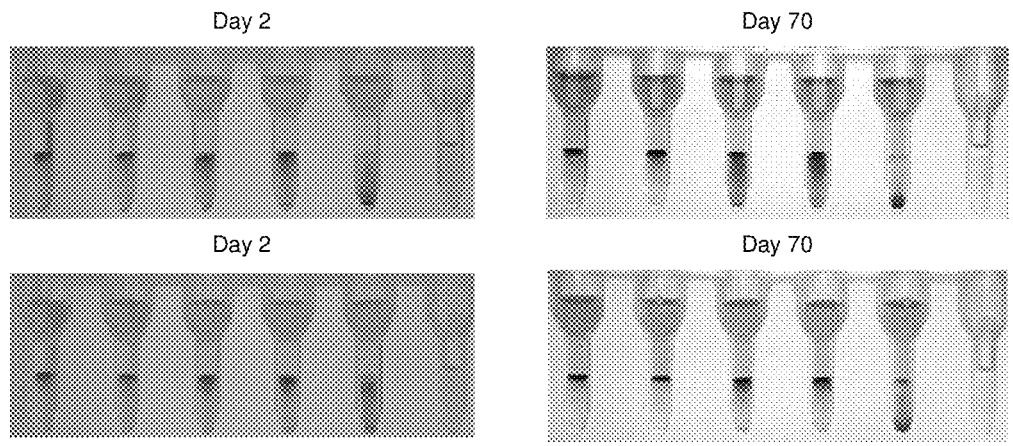
Figure 4:
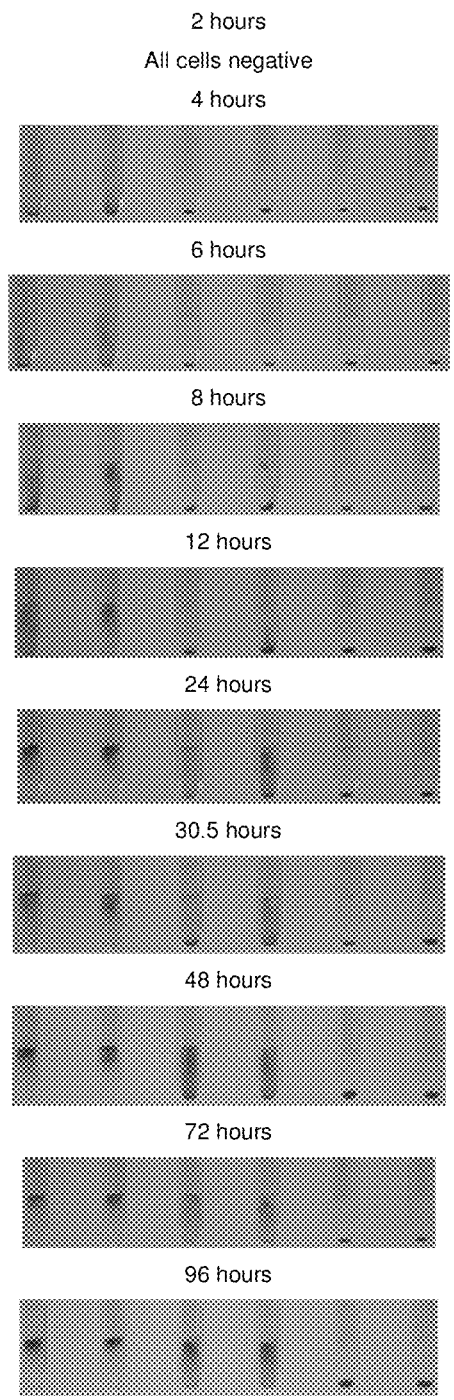

The invention will now be illustrated by reference to the following non-limiting Examples and Figures of the accompanying drawings in which:

FIG. 1 shows Diamed results of Cellstab™ stored cells transformed by natural A glycolipid transformation solution at (L to R) 10 mg/mL, 5 mg/mL, 2 mg/mL, 2 mg/mL* and 1 mg/mL. Antisera used are Albaclone (top) and Bioclone (bot- FIG. 4 shows Diamed results of cells transformed at 4° C. by $A_{tri}$-sp-Ad-DOPE (I) transformation solution at (L to R): washed 0.08 mg/mL; unwashed 0.08 mg/mL; washed 0.05 mg/mL; unwashed 0.05 mg/mL; washed 0.03 mg/mL; and unwashed 0.03 mg/mL. The antisera used was Bioclone anti-A.

Figure 5:
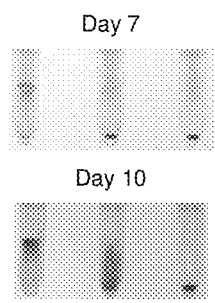

FIG. 5 shows cells that were no longer washed prior to testing. Diamed results of cells transformed at 4° C. by $A_{tri}$-sp-Ad-DOPE (I) transformation solution at (L to R): 0.08 mg/mL, 0.05 mg/mL and 0.03 mg/mL. The antisera used was Bioclone anti-A.

Figure 6:
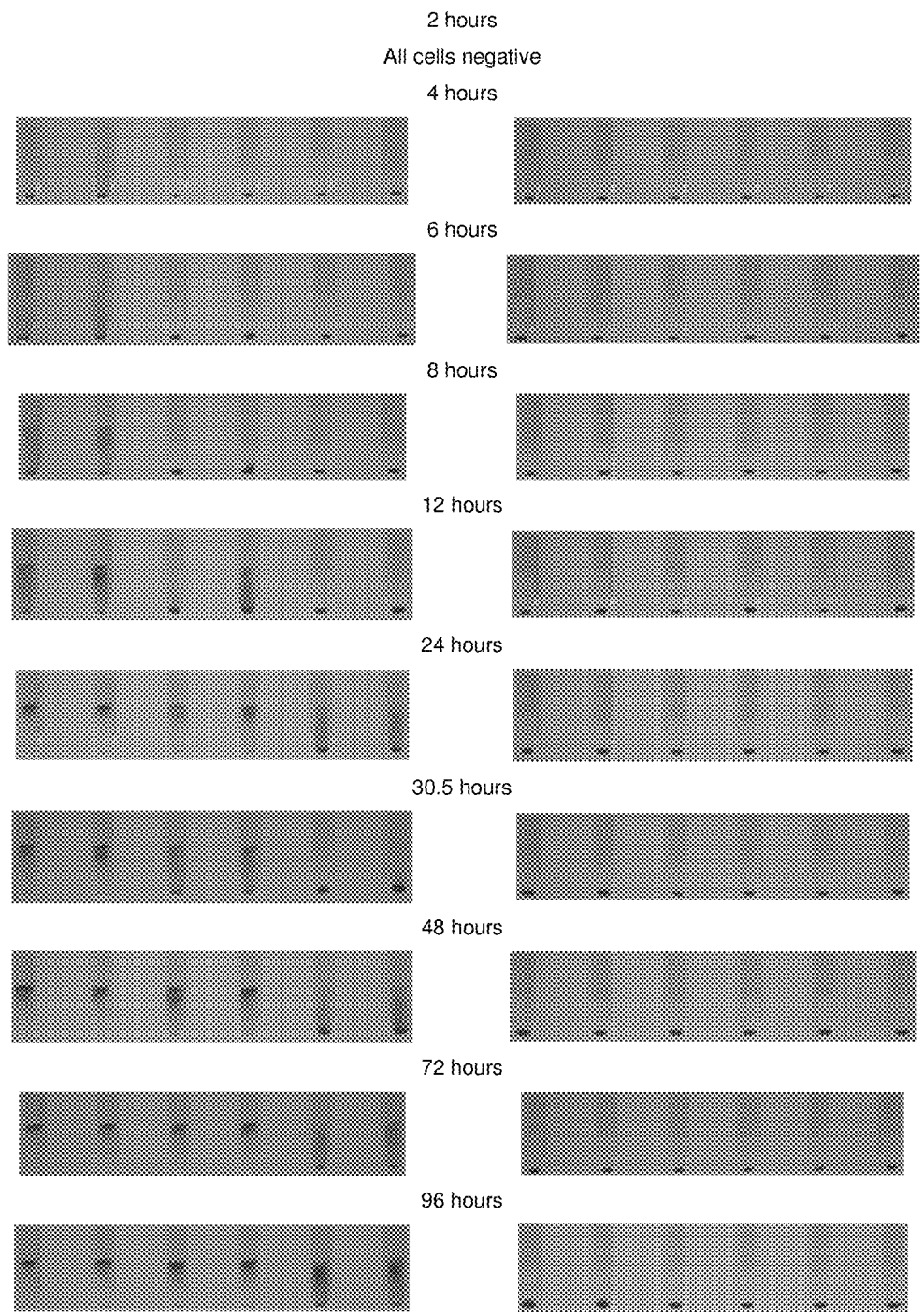

FIG. 6 shows in the left column Diamed results of cells transformed at 4° C. by $B_{tri}$-sp-Ad-DOPE (VI) transformation solution at (L to R): washed 0.6 mg/mL; unwashed 0.6 mg/mL; washed 0.3 mg/mL; unwashed 0.3 mg/mL; washed 0.15 mg/mL; and unwashed 0.15 mg/mL; and in the right column Diamed results of cells transformed at 4° C. by $B_{tri}$-sp-Ad-DOPE (VI) transformation solution at (L to R): washed 0.08 mg/mL; unwashed 0.08 mg/mL; washed 0.05 mg/mL; unwashed 0.05 mg/mL; washed 0.03 mg/mL; and unwashed 0.03 mg/mL. The antisera used was Bioclone anti-B.

Figure 7:
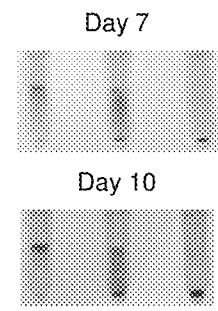

FIG. 7 shows cells that were no longer washed prior to testing. Diamed results of cells transformed at 4° C. by $B_{tri}$-sp-Ad-DOPE (VI) transformation solution at (L to R): 0.6 mg/mL, 0.3 mg/mL and 0.15 mg/mL.

Figure 8:
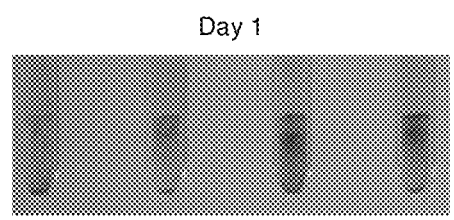
Figure 8:
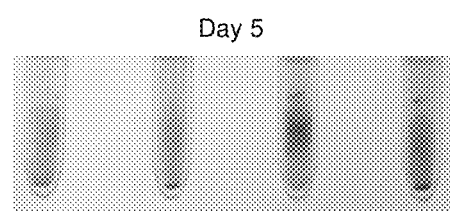

FIG. 8 shows Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain washed A 0.07+B 0.3 mg/mL against anti-A and anti-B. Wells 3 and 4 contain unwashed A 0.07+B 0.3 mg/mL against anti-A and anti-B.

Figure 9:
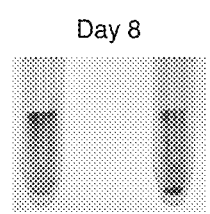

FIG. 9 shows cells that were no longer washed prior to testing. Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain unwashed A 0.07+B 0.3 mg/mL against anti-A and anti-B.

Figure 10:
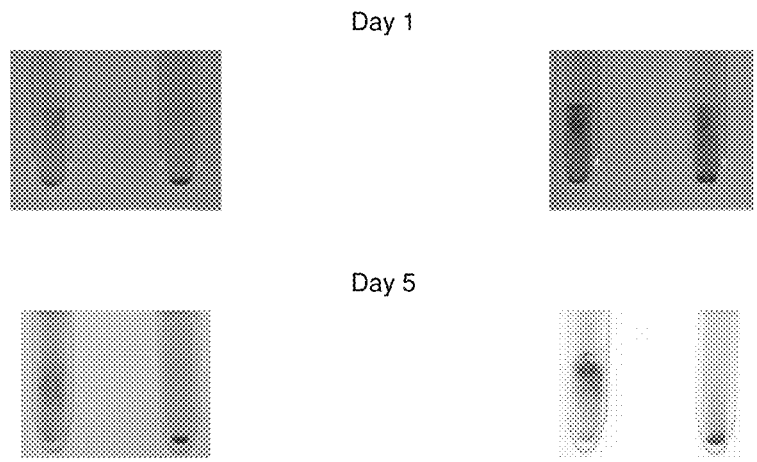

FIG. 10 shows Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain washed A 0.07+B 0.2 mg/mL against anti-A and anti-B. Wells 3 and 4 contain unwashed A 0.07+B 0.2 mg/mL against anti-A and anti-B.

Figure 11:
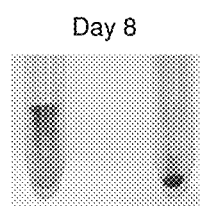

FIG. 11 shows cells that were no longer washed prior to testing. Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain unwashed A 0.07+B 0.2 mg/mL against anti-A and anti-B.

Figure 12:
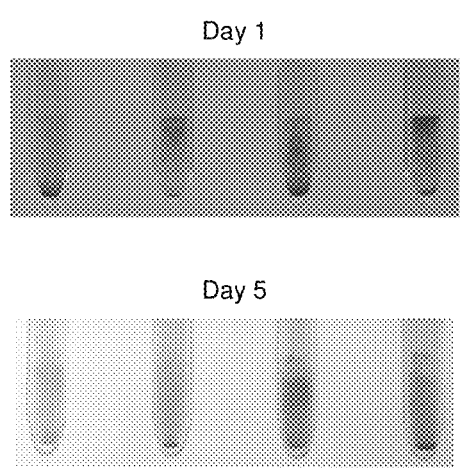

FIG. 12 shows Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain washed A 0.06+B 0.3 mg/mL against anti-A and anti-B. Wells 3 and 4 contain unwashed A 0.06+B 0.3 mg/mL against anti-A and anti-B.

Figure 13:
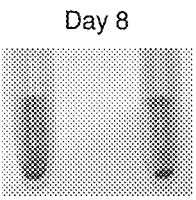

FIG. 13 shows cells that were no longer washed prior to testing. Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain unwashed A 0.06+B 0.3 mg/mL against anti-A and anti-B.

Figure 14:
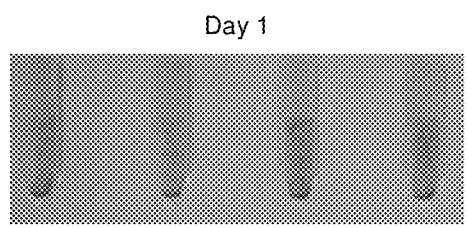
Figure 14:
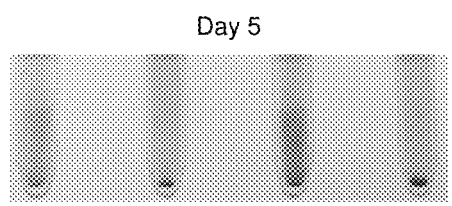

FIG. 14 shows Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain washed A 0.06+B 0.2 mg/mL against anti-A and anti-B. Wells 3 and 4 contain unwashed A 0.06+B 0.2 mg/mL against anti-A and anti-B.

Figure 15:
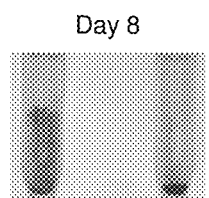

FIG. 15 shows cells that were no longer washed prior to testing. Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain unwashed A 0.06+B 0.2 mg/mL against anti-A and anti-B.

Figure 16:
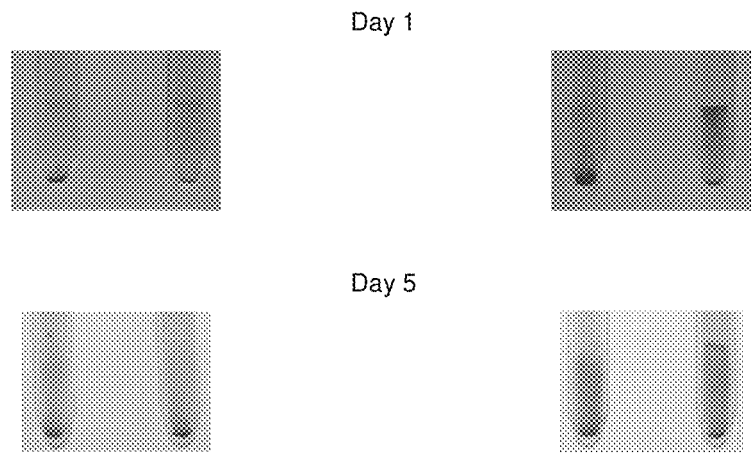

FIG. 16 shows Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain washed A 0.05+B 0.3 mg/mL against anti-A and anti-B. Wells 3 and 4 contain unwashed A 0.05+B 0.3 mg/mL against anti-A and anti-B.

Figure 17:
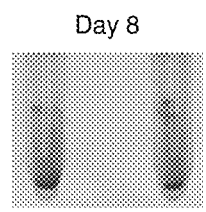

FIG. 17 shows cells that were no longer washed prior to testing. Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain unwashed A 0.05+B 0.3 mg/mL against anti-A and anti-B.

Figure 18:
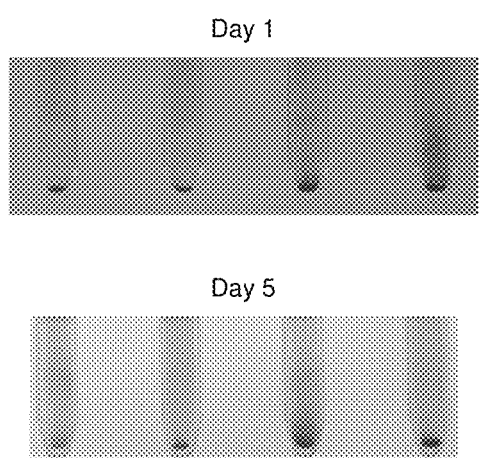

FIG. 18 shows Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain washed A 0.05+B 0.2 mg/mL against anti-A and anti-B. Wells 3 and 4 contain unwashed A 0.05+B 0.2 mg/mL against anti-A and anti-B.

Figure 19:
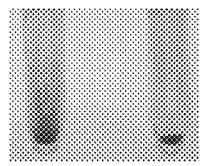

FIG. 19 shows cells that were no longer washed prior to testing. Diamed results of cells transformed at 4° C. by parallel transformation with $A_{tri}$-sp-Ad-DOPE (I) and $B_{tri}$-sp-Ad-DOPE (VI). Wells 1 and 2 (L to R) contain unwashed A 0.05+B 0.2 mg/mL against anti-A and anti-B.

COMPARATIVE EXAMPLES

The Comparative Examples do not form part of the invention claimed. The Comparative Examples describe red blood cell transformation with natural glycolipids.

Comparative Example 1

Preparation of Natural Glycolipids

Purification by HPLC

In the first stage, columns were packed with dry silica (15-25 µm) before each run. Relatively dirty samples could be used in HPLC because the silica could be discarded along with the theoretically high level of irreversibly bound contaminants.

Glycolipids were separated on silica gel with a mobile phase of increasing polarity. The program was a linear gradient beginning with 100% chloroform-methanol-water 80:20:1 (v/v) and ending with 100% chloroform-methanol-water 40:40:12 (v/v).

The HPLC equipment used was a Shimadzu system capable of pumping and mixing four separate solvents at programmed ratios. As chloroform, methanol and water evaporate at different rates, a program was developed whereby the solvent components were not mixed prior to entering the HPLC.

The Shimadzu HPLC mixes four different liquids by taking a "shot" from each of four bottles in turn. "Shots" of chloroform and water directly next to each other in the lines may cause miscibility problems. Methanol was sandwiched in between these two immiscible components. Additionally, the water was pre-mixed with methanol in a 1:1 ratio to further prevent problems with miscibility.

Comparative Example 2

Transformation of Red Blood Cell Transformation with Natural Glycolipids

Agglutination

Transformation of red blood cells was assessed by agglutination using the Diamed-ID Micro Typing System in addition to using conventional tube serology. Diamed ABO typing cards were not used. The cards used were NaCl, Enzyme test and cold agglutinin cards, which were not pre-loaded with any antisera or other reagents. This allowed the use of specific antisera with both methodologies.

TABLE 1

Gel-cards.

| Manufacturer | Catalogue ref |
|---|---|
| Diamed | NaCl, Enzyme test and cold agglutinin cards |

A comparative trial was carried out between tube serology and the Diamed system to establish the performance of the two systems. Cells were transformed at 25° C. for 4 hours. Seraclone and Alba-clone anti-A sera were used to gauge equivalency. The results are shown in Table 3 below.

TABLE 2

Antisera used in comparison of tube serology with the Diamed system.

| Manufacturer | Catalogue ref | Lot | Expiry |
|---|---|---|---|
| Albaclone, SNBTS | Anti-A. | Z0010770 | 12 Dec. 2004 |
| Seraclone, Biotest | 801320100 | 1310401 | 12 Apr. 2003 |

TABLE 3

Agglutination results comparing tube serology with the Diamed system.

| | | A glycolipid (mg/mL) | | | | |
|---|---|---|---|---|---|---|
| | | 10 | 5 | 2 | 1 | 0 |
| Tube | Albaclone | 3+ | 2+ | 0 | 0 | 0 |
| | Seraclone | 3+ | 2+ | 0 | 0 | 0 |
| Diamed | Albaclone | 2+ | 2+ | 0 | 0 | 0 |
| | Seraclone | 3+ | 2+ | 1+ | w+ | 0 |

In this experiment, the Diamed system proved to be more sensitive to the weaker reactions than tube serology with the Seraclone anti-A, but not with Albaclone. These reagents are formulated differently, and are thus not expected to perform identically. However, the fact that the Seraclone anti-A tube serology combination did not detect positivity is probably due to operator interpretation. The weaker reactions are notoriously difficult to accurately score, and the difference between 1+ and 0 can be difficult to discern in tubes.

Optimisation

The variables of glycolipid concentration, incubation temperature, incubation duration, diluent and storage solution were examined for their effect on cell health. Efficiency and stability of transformation was assessed by agglutination with the relevant antibody.

TABLE 4

Tube serology agglutination of natural glycolipid A transformed cells over different times and temperatures.

| | A | | | | | | | | |
|---|---|---|---|---|---|---|---|---|---|
| | 10 | 5 | 2 | 1 | 0.1 | 0.01 | 0.001 | 0.0001 | 0 |
| Seraclone (37° C. for 1.5 hours) | 3+ | 2+ | 0 | 0 | | | | | 0 |

TABLE 4-continued

Tube serology agglutination of natural glycolipid A transformed cells over different times and temperatures.

| | A | | | | | | | | |
|---|---|---|---|---|---|---|---|---|---|
| | 10 | 5 | 2 | 1 | 0.1 | 0.01 | 0.001 | 0.0001 | 0 |
| Seraclone (25° C. for 4 hours) | 4+ | 3+ | 2+ | 1+ | w+ | 0 | 0 | 0 | 0 |

Glycolipid Concentration

Initial transformation experiments were carried out with a highly purified (HPLC) $Le^b$ glycolipid sample and a less pure blood group A glycolipid sample. Transformation was performed at 37° C. for 1.5 hours The A glycolipid sample contained other lipid impurities and thus comparatively less blood group A molecules by weight than the $Le^b$ glycolipid sample of equivalent concentration (w/v). This seems to be borne out by the fact that higher concentrations of the A glycolipid than the $Le^b$ glycolipid were required to produce equivalent agglutination scores (see Table 6).

The level of impurity in the A glycolipid sample may also have contributed to the lower stability over the 62 day period—the A-transformed cells 'died' at the highest concentration (having received the largest dose of impurity).

TABLE 5

Anti-A and anti-$Le^b$ used in initial testing of natural glycolipid transformation.

| Manufacturer | Catalogue ref | Batch number | Expiry |
|---|---|---|---|
| Anti-A | | | |
| Seraclone, Biotest | 801320100 | 1310401 | 12 Apr. 2003 |
| Anti-$Le^b$ | | | |
| CSL | | 12801 | |

TABLE 6

Stability of RBCs transformed with natural A and $Le^b$ glycolipid as assessed by tube serology agglutination over the period of 62 days.

| Glycolipid | $Le^b$ | | | A | | |
|---|---|---|---|---|---|---|
| (mg/mL) | Day 1 | Day 25 | Day 62 | Day 1 | Day 25 | Day 62 |
| 10 | 4+ | | 2-3+ | 3+ | 2+ | ? |
| 5 | 4+ | | 2-3+ | 2+ | 2+ | w+ |
| 2 | 3+ | | 1-2+ | 0 | 1+ | 0 |
| 1 | 4+ | | 2+ | 0 | 1+ | 0 |
| 0.1 | 3+ | 2+ | | 0 | 0 | |
| 0.01 | 2+ | 2+ | | 0 | 0 | |
| 0.001 | 2+ | 2+ | | 0 | 0 | |
| 0.0001 | 2+ | 0 | | 0 | 0 | |
| 0 | 0 | 0 | 0 | 0 | 0 | 0 |

The above cells were also rated for haemolysis and these results are shown in Table 7 below.

TABLE 7

Haemolysis as assessed visually.

| Glycolipid concentration | Haemolysis | | | | | |
|---|---|---|---|---|---|---|
| | Le$^b$ | | | A | | |
| (mg/mL) | Day 1 | Day 25 | Day 62 | Day 1 | Day 25 | Day 62 |
| 10 | h | 0 | h | h | h | dead |
| 5 | hh | 0 | hhh | w | 0 | hh |
| 2 | w | 0 | hhh | w | 0 | hhhhh |
| 1 | w | 0 | hhh | h | 0 | hhhh |
| 0.1 | | | h | | | hhh |
| 0.01 | | | hh | | | |
| 0.001 | | | h | | | |
| 0.0001 | | | h | | | |
| Control | h | 0 | h | h | h | |

Day 1—in the supernatant of the first wash after transformation; Days 25 and 62—in the cell preservative solution before the cells are resuspended after storage. Scoring scale is analogous to the 4+ to 0 agglutination scale: hhhh—severely haemolysed, hhh—very haemolysed, hh—moderately haemolysed, h—mildly haemolysed, w—faintly haemolysed and 0—no haemolysis seen.

These results show that cell haemolysis can be shown to be associated with transformation with high concentrations of glycolipid. It is unclear whether the mechanism underlying this is disruption of the plasma membrane by large amounts of glycolipid being inserted, the rate of that insertion, or is possibly due to the quantity of associated impurity. However, the results for Le$^b$ at day 62 seem to support the first explanation.

The Le$^b$ sample was highly purified—before being dissolved, it was a powder of pure white colour, and thus it is unlikely that the haemolysis was due to the deleterious effect of impurities. It is clear to see that at 62 days, the amount of haemolysis occurring diminishes in line with the decrease in the glycolipid concentration.

Incubation Temperature

Experiments were carried out to investigate other possible mechanisms for the reduction of haemolysis of RBCs during the insertion step. Previous experiments had shown that haemolysis was worse at higher glycolipid concentrations than at lower concentrations, and it is thought that haemolysis may also be related to the rate of glycolipid insertion. Since temperature is believed to affect the rate of insertion, experiments were conducted comparing transformation at 37° C. with transformation at room temperature (RT; 25° C.).

Since the rate was expected to slow down as temperature decreased, the incubation period for the RT experiment was 4 hrs. Haemolysis was assessed visually and scored following insertion. Serology tests were also performed on the cells. The results are shown in Table 8.

TABLE 8

The effect of incubation temperature on haemolysis and agglutination during insertion of glycolipids into RBC membranes. Haemolysis was scored visually at each of the three washes.

| | Haemolysis | | | | | | Serology | |
|---|---|---|---|---|---|---|---|---|
| | RT | | | 37° C. | | | | |
| Glycolipid | wash | wash | wash | wash | wash | wash | | |
| (mg/mL) | 1 | 2 | 3 | 1 | 2 | 3 | RT | 37° C. |
| 10 | w | 0 | 0 | hh | w | 0 | 2+ | 2+ |
| 1 | w | 0 | 0 | hh | h | vw | 1+ | w+ |

Incubation Duration

Incubation at 37° C. was carried out for 1 and 2 hours and its effect on cell health and transformation assessed by agglutination with the relevant antibody.

TABLE 9

Antisera used in the duration of incubation trial.

| Manufacturer | Catalogue ref | Batch number | Expiry date |
|---|---|---|---|
| Albaclone, SNBTS | Anti-A. | Z0010770 | 12 Dec. 2004 |
| Bioclone, OCD | Anti-A, experimental reagent | DEV01102 | — |
| Albaclone, SNBTS | Anti-B | Z0110670 | 01 Jul. 2005 |
| Bioclone, OCD | Anti-B, experimental reagent | DEV01103 | — |

TABLE 10

Effect of incubation time on agglutination of cells transformed with natural glycolipids.

| | Concentration | Albaclone | | BioClone | |
|---|---|---|---|---|---|
| Glycolipid | (mg/mL) | 1 hour | 2 hours | 1 hour | 2 hours |
| A | 10 | 4+ | 4+ | 4+ | 4+ |
| | 5 | 4+ | 4+ | 4+ | 2+ |
| | 2 | 4+ | 3+ | 3+ | 2+ |
| | 1 | 3+ | 2+ | 2+ | 2+ |
| | 0.5 | 2+ | 2+ | 1+ | w+ |
| B | 10 | 3+ | 2+ | 4+ | 1+ |
| | 5 | 3+ | 2+ | 3+ | 2+ |
| | 2 | 2+ | 2+ | 2+ | 1+ |
| | 1 | 1+ | w+ | 1+ | w+ |
| | 0.5 | 1+ | w+ | w+ | w+ |

These results indicate that increasing the duration of incubation during natural glycolipid insertion does not enhance agglutination. In fact, the agglutination scores are reduced after the two hour incubation. This may be due to the destabilisation of the membrane or exchange of the glycolipids back into solution.

Diluent

Experiments were also carried out to determine if changing the glycolipid diluent solution could reduce haemolysis. Working strength PBS was compared with 2×PBS and 2% Bovine Serum Albumin (BSA) in working strength PBS. Cells were incubated at 37° C. for 1.5 hours. The results are shown in Table 11.

TABLE 11

Study on the effect on haemolysis of changing the glycolipid diluent solutions during insertion of glycolipids into RBC membranes.

| Glycolipid concentration | Glycolipid Diluent Solution | | |
|---|---|---|---|
| (mg/mL) | PBS | 2 × PBS | 2% BSA in PBS |
| 40 | Hhh | hhh | hhh |
| 30 | Hhh | hhh | hhh |
| 20 | Hhh | hhh | hhh |
| 10 | Hhh | hhh | hhh |
| 0 | 0 | 0 | 0 |

Stability

Once A and B blood group glycolipids had been HPLC purified to an acceptable level, an experiment to find the appropriate concentrations for stability trials was carried out.

TABLE 12

Early stability trial of cells transformed with natural A glycolipid.

| | | A | | | | | | | | |
|---|---|---|---|---|---|---|---|---|---|---|
| Expt | Day | 10 | 5 | 2 | 1 | 0.1 | 0.01 | 0.001 | 0.0001 | 0 |
| 1 | 7 | 4+ | 3-4+ | 1+ | 0 | 0 | 0 | 0 | 0 | 0 |
| 2 | 43 | 3+ | w+ | 0 | 0 | 0 | 0 | 0 | 0 | 0 |
| 3 | 50 | 1+ | 0 | 0 | 0 | | | | | |
| 4 | 60 | 3+ | 1+ | 0 | | | | | | |
| 5 | 67 | w+ | vw | vw | | | | | | |
| 6 | 74 | 2+ | 0 | 0 | | | | | | |
| 7 | 81 | 2+ | 1+ | 0 | | | | | | |

TABLE 13

Antisera used in stability trials (Table 14 and Table 15).

| Manufacturer | Catalogue ref | Batch number | Expiry date |
|---|---|---|---|
| Albaclone, SNBTS | Anti-A. | Z0010770 | 12 Dec. 2004 |
| Bioclone, OCD | Anti-A, experimental reagent | DEV01102 | — |
| Albaclone, SNBTS | Anti-B | Z0110670 | 01 Jul. 2005 |
| Bioclone, OCD | Anti-B, experimental reagent | DEV01103 | — |

TABLE 14

Tube serology of O RBCs transformed with A glycolipid in order to establish appropriate concentrations for stability trials.

| | | A glycolipid (mg/mL) | | | | | | | | |
|---|---|---|---|---|---|---|---|---|---|---|
| Anti-A | Expt | 10 | 5 | 2 | 1 | 0.5 | 0.1 | 0.01 | 0.001 | 0 |
| Alba | 1 | 3+ | 2+ | 1+ | 0 | | 0 | 0 | 0 | 0 |
| | 2 | 4+ | 4+ | 3+ | 2+ | w+ | | | | |
| Bio | 1 | 3+ | 2+ | 1+ | 0 | | 0 | 0 | 0 | 0 |
| | 2 | 4+ | 4+ | 3+ | 2+ | w+ | | | | |

1 & 2 Transformation at 25° C. for 4 hours

TABLE 15

Tube serology of O RBCS transformed with B glycolipid in order to establish appropriate concentrations for stability trials.

| | | B glycolipid (mg/mL) | | | | | | | | |
|---|---|---|---|---|---|---|---|---|---|---|
| Anti-B | Expt | 10 | 5 | 2 | 1 | 0.5 | 0.1 | 0.01 | 0.001 | 0 |
| Alba | 1 | 2+ | 1+ | w+ | 0 | | 0 | 0 | 0 | 0 |
| | 2 | 1+ | 1+ | w+ | 0 | w+ | | | | |
| Bio | 1 | 3+ | 2+ | w+ | 0 | | 0 | 0 | 0 | 0 |
| | 2 | 1+ | 1+ | w+ | 0 | w+ | | | | |

1 & 2 Transformation at 25° C. for 4 hours

Two sets of cells were transformed with different concentrations of natural A glycolipid. Transformation was performed at 25° C. One set of cells was tested long term, and one set of cells was tested weekly for agglutination. The agglutination results from tube serology and Diamed are shown in Table 16 below. All cells were stored in Cellstab™ in bottles with flat bases. The cells showed minimal to no haemolysis at any time.

TABLE 16

Agglutination results for cells transformed with different concentrations of natural A glycolipid. Results were obtained using Albaclone anti-A.

| | | A glycolipid (mg/mL) | | | | |
|---|---|---|---|---|---|---|
| | | 10 | 5 | 2 | 1 | 0.1 | control |
| Long term testing | | | | | | | |
| Day 1 | Tube | 4+ | 3+ | 2+ | 1+ | +w | 0 |
| | Diamed | 3+ | 3+ | +w | 0 | 0 | 0 |
| Day 17 | Tube | 3+ | 2+ | 0 | 0 | | 0 |
| | Diamed | 3+ | 2+ | 1+ | 0 | | 0 |
| Weekly testing | | | | | | | |
| Day 1 | Tube | 3+ | 2+ | 0 | 0 | | |
| | Diamed | 3+ | 0 | 0 | 0 | | |
| Day 8 | Tube | 1+ | 0 | 0 | 0 | | |
| | Diamed | 3+ | 0 | 0 | 0 | | |
| Day 15 | Tube | 1+ | 0 | 0 | 0 | | |
| | Diamed | 3+ | 2+ | 0 | 0 | | |
| Day 22 | Tube | 3+ | 0 | 0 | 0 | | |
| | Diamed | 3+ | 0 | 0 | 0 | | |
| Day 29 | Tube | *+w | *0 | *0 | *0 | | |
| | Diamed | *3+ | *0 | *0 | *0 | | |
| Day 36 | Tube | * | * | * | *0 | | |
| | Diamed | *3+ | *0 | *0 | *0 | | |
| Day 43 | Tube | * | * | * | *0 | | |
| | Diamed | * | * | * | *0 | | |

*Albaclone, while all others used Seraclone anti-A.

Storage Solution

Comparison of the two cell storage solutions, Celpresol™ (CSL) and Cellstab™ (Diamed) was carried out to test their relative abilities to support modified RBCs.

The stability of RBCs transformed with blood group A and B antigen solutions of varying concentrations when stored in two different cell preservative solutions—Cellstab™ and Alsevers™—was trialed.

A and B antisera from two different sources were used in serology testing.

All cells were tested using the standard tube serology platform up to 42 days, at which time the cell agglutination reactions had become too difficult to score manually (see Table 17 for A results and Table 18 for B results).

Diamed gel-card testing was carried out to day 56 for the Alsevers stored cells, and discontinued at day 63 due to fungal contamination (although still returning positive scores).

Figure 2:
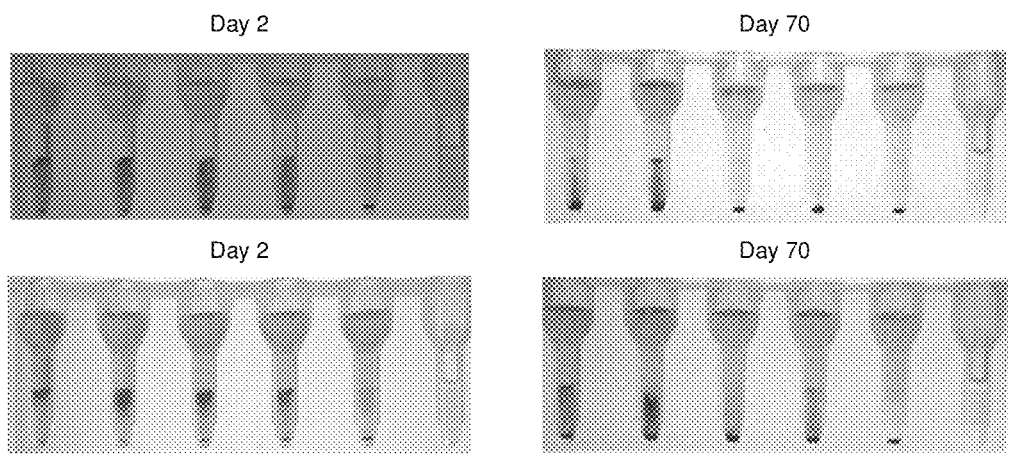
FIG. 2 shows Diamed results of Cellstab™ stored cells transformed by natural B glycolipid transformation solution at (L to R) 10 mg/mL, 5 mg/mL, 2 mg/mL, 2 mg/mL* and 1 mg/mL. Antisera used are Albaclone (top) and Bioclone (bottom). (*—transformation solution (containing glycolipids) was not washed out after the incubation, it was left in over night and washed out the next day (day 2)).

The Cellstab™ stored cells continued to be tested up to day 70, and were still viable at this point (see FIG. 1 for A results and FIG. 2 for B results).

The reagents used in the stability trial are shown in Table 13.

TABLE 17

Tube serology results of stability trial of cells transformed with varying concentrations of A glycolipid and stored in either Cellstab ™ or Alsevers ™

| Day | Cell storage solution | Albaclone Anti-A (SNBTS) Transformation Solution (mg/mL) | | | | | Bioclone Anti-A (OCD - Developmental reagent) | | | | |
|---|---|---|---|---|---|---|---|---|---|---|---|
| | | 10 | 5 | 2 | 2* | 1 | 10 | 5 | 2 | 2* | 1 |
| 2 | Alsevers | 4+ | 3+ | 2+ | 1+ | w+ | 3+ | 3+ | 1+ | 1+ | 0 |
| | Cellstab ™ | 4+ | 4+ | 3+ | 1+ | 1+ | 3+ | 3+ | 2+ | 1+ | 0 |
| 8 | Alsevers | 4+ | 4+ | 2+ | 1+ | 1+ | 2+ | 2+ | 1+ | 1+ | 0 |
| | Cellstab ™ | 4+ | 4+ | 3+ | 2+ | 1+ | 3+ | 3+ | 2+ | w+ | 0 |
| 14 | Alsevers | 4+ | 3+ | 2+ | 2+ | w+ | 2+ | 1+ | w+ | vw | 0 |
| | Cellstab ™ | 4+ | 3+ | 3+ | 2+ | w+ | 3+ | 2+ | w+ | vw | 0 |
| 21 | Alsevers | 3+ | 2+ | 2+ | 2+ | 1+ | 2+ | 2+ | 2+ | 1+ | 0 |
| | Cellstab ™ | 3+ | 3+ | 2+ | + | ‡ | 2+ | ‡ | ‡ | ‡ | 0 |
| 28 | Alsevers | 2+ | 2+ | 1+ | 1+ | 0 | 2+ | 2+ | 1+ | 1+ | 0 |
| | Cellstab ™ | 2+‡ | 2+‡ | ‡ | ‡ | 0 | 1+ | w+ | 0 | 0 | 0 |
| 36 | Alsevers | 3+ | 2+ | 2+ | 2+ | 1+ | 3+ | 3+ | 2+ | 1+ | 1+ |
| | Cellstab ™ | 3+‡ | 2+‡ | ‡ | ‡ | ‡ | 3+‡ | ‡ | ‡ | ‡ | ‡ |
| 42 | Alsevers | 3+ | 3+ | 1+ | w+ | 0 | 2+ | 2+ | 2+ | 1+ | 1+ |
| | Cellstab ™ | 4+‡ | 4+‡ | ‡ | ‡ | ‡ | ‡ | ‡ | ‡ | ‡ | 0 |

*transformation solution (containing glycolipids) was not washed out after the incubation, it was left in over night and washed out the next day.
‡positive cell button, but cells fall off as negative (score assignment impossible).

TABLE 18

Tube serology results of stability trial of cells transformed with varying concentrations of B glycolipid and stored in either Cellstab ™ or Alsevers ™.

| Day | Cell storage solution | Albaclone Anti-B (SNBTS) Transformation Solution (mg/mL) | | | | | Bioclone Anti-B (OCD - Developmental reagent) | | | | |
|---|---|---|---|---|---|---|---|---|---|---|---|
| | | 10 | 5 | 2 | 2* | 1 | 10 | 5 | 2 | 2* | 1 |
| 2 | Alsevers | 3+ | 3+ | 1+ | 1+ | 1+ | 2+ | 1+ | 1+ | 1+ | 0 |
| | Cellstab ™ | 3+ | 3+ | 2+ | 2+ | 1+ | 2+ | 2+ | 2+ | 1+ | w+ |
| 8 | Alsevers | 1+ | 1+ | w+ | 0 | 0 | 0 | 0 | 0 | 0 | 0 |
| | Cellstab ™ | 2+ | 1+ | w+ | 0 | 0 | 1+ | 1+ | w+ | 0 | 0 |
| 14 | Alsevers | 2+ | 2+ | 0 | w+ | 0 | 0 | 1+ | 1+ | 2+ | 0 |
| | Cellstab ™ | 1+ | w+ | 0 | 0 | 0 | 2+ | 2+ | w+ | 1+ | 1+ |
| 21 | Alsevers | ‡ | ‡ | ‡ | ‡ | ‡ | 1 | 1 | ‡ | ‡ | ‡ |
| | Cellstab ™ | ‡ | ‡ | ‡ | ‡ | ‡ | + | + | + | ‡ | ‡ |
| 28 | Alsevers | 2+ | 1+ | w+ | 0 | 0 | 2+ | 1+ | 2+ | 0 | 0 |
| | Cellstab ™ | ‡ | ‡ | ‡ | 0 | 0 | ‡ | 0 | ‡ | ‡ | 0 |
| 36 | Alsevers | 2+ | 2+ | 2+ | 1+ | 1+ | 2+ | 2+ | 2+ | 1+ | 1+ |
| | Cellstab ™ | ‡ | ‡ | ‡ | ‡ | ‡ | ‡ | ‡ | ‡ | ‡ | ‡ |
| 42 | Alsevers | 2+ | 2+ | 2+ | 2+ | w+ | 2+ | 2+ | 1+ | w+ | w+ |
| | Cellstab ™ | ‡ | ‡ | ‡ | ‡ | ‡ | ‡ | ‡ | ‡ | ‡ | ‡ |

*transformation solution (containing glycolipids) was not washed out after the incubation, it was left in over night and washed out the next day.
‡ positive cell button, but cells fall off as negative (score assignment impossible).

FACS Analysis of Glycolipid Insertion

Figure 3:
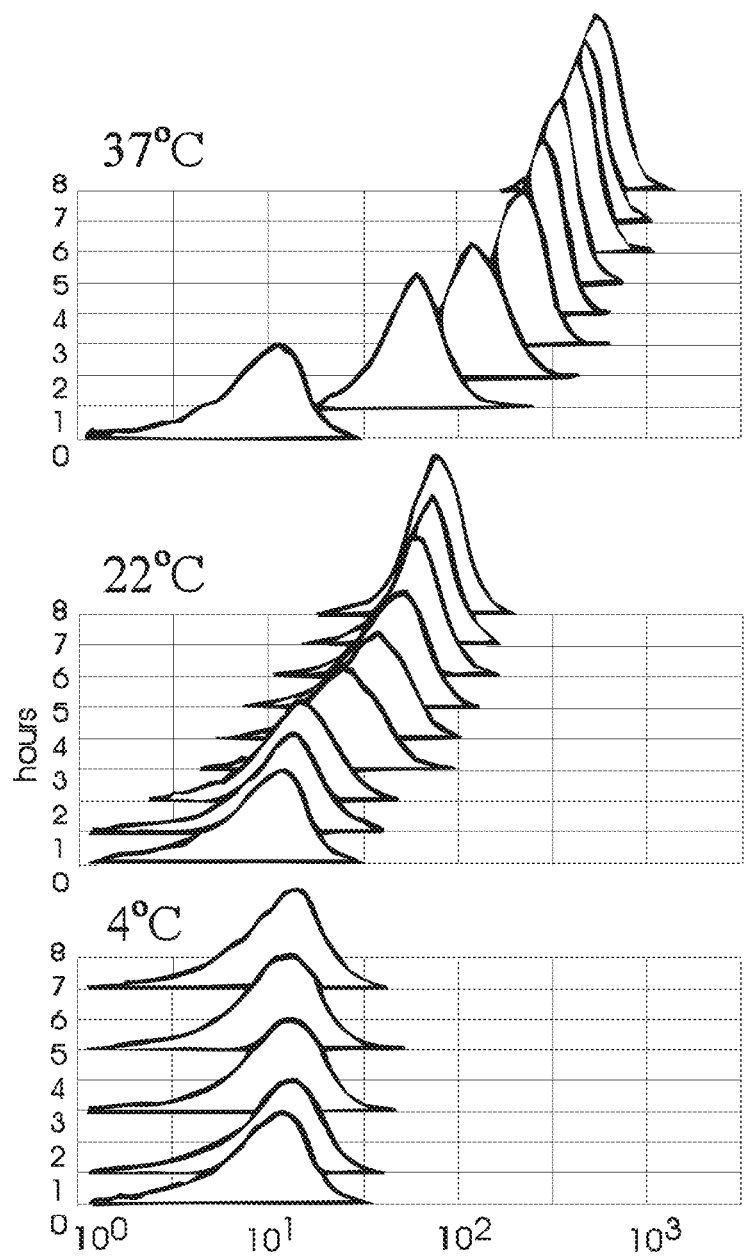
FIG. 3 shows FACS analysis following in vitro transformation of human Le(a-b-) red cells with natural $Le^b$-6 glycolipid over time at three transformation temperatures, 37° C. (top), 22° C. (middle) and 4° C. (bottom).

Transformation of human Le(a-b-) red cells with natural Le$^b$-6 glycolipid over time at three transformation temperatures (37° C., 22° C. and 4° C.) was performed (FIG. 3). Natural Le$^b$-6 glycolipid was dissolved in plasma and used to transform RBCs at a final concentration of 2 mg/mL and a final suspension of 10%.

Reactivity was determined by FACS analysis using a Gamma anti-Leb. (The serological detection level is around 10$^2$ molecules. The insertion of natural glycolipids at 4° C. for 8 hours was not detectable by agglutination with antibodies.) Projection of the rate of insertion curve from FACS analysis did not indicate that the rate of insertion at 4° C. would have reached agglutination detection levels within 24 hours.

Low Incubation Temperature

Transformation of RBCs with natural A or B glycolipid was performed at 37° C. for 1 hour and 2° C. for varying intervals. Cells were agglutinated with Bioclone anti-A or Bioclone anti-B. The results are provided in Tables 19 and 20.

TABLE 19

Diamed results of comparison of natural A glycolipid transformation at 37° C. for 1 hour and 2° C. for varying intervals.

| Temp | Time (hours) | Nat A (mg/mL) | | | | |
|---|---|---|---|---|---|---|
| | | 10 | 5 | 2 | 1 | 0 |
| 37° C. | 1 | 3+ | 3+ | 2-3+ | 2+ | 0 |
| 2° C. | 1 | 0 | 0 | 0 | 0 | 0 |
| | 4 | 0 | 0 | 0 | 0 | 0 |
| | 8 | 1-2+ | 0 | 0 | 0 | 0 |
| | 24 | 2-3+ | 2+ | 1-2+ | 0 | 0 |
| | 48 | 3+ | 2-3+ | 2-3+ | 0 | 0 |
| | 72 | 3-4+ | 3+ | 2+ | 0 | 0 |

TABLE 20

Diamed results of comparison of natural B glycolipid transformation at 37° C. for 1 hour and 2° C. for varying intervals.

| Temp | Time (hours) | Nat B (mg/mL) | | | | |
|---|---|---|---|---|---|---|
| | | 10 | 5 | 2 | 1 | 0 |
| 37° C. | 1 | 3+ | 2-3+ | 2+ | 0 | 0 |
| 2° C. | 1 | 0 | 0 | 0 | 0 | 0 |
| | 4 | 0 | 0 | 0 | 0 | 0 |
| | 8 | 0 | 0 | 0 | 0 | 0 |
| | 24 | 1+ | 0 | 0 | 0 | 0 |
| | 48 | 2+ | 1-2+ | 0 | 0 | 0 |
| | 72 | 2+ | 1+ | 0 | 0 | 0 |

The rate of transformation is slow for both natural A glycolipid and natural B glycolipid as demonstrated by the negative agglutination scores after 1 hour at 2° C. Considerable insertion at 37° C. for this time interval has been demonstrated.

Natural A glycolipid insertion at 2° C. required 48 hours to reach the same level of insertion obtainable by transformation at 37° C. After this time further insertion was not observed. Likewise, natural B glycolipid insertion at 2° C. was not as rapid as transformation at 37° C. The agglutination scores did not improve upon continued incubation and thus seemed to have reached maximal insertion at this time point for these concentrations.

EXAMPLES

The Examples describe red blood cell transformation with the synthetic molecule constructs of the invention. In the context of these examples the term "synthetic glycolipids" is used to refer to these constructs.

Example 1

Preparation of Synthetic Glycolipids

Materials and Methods

TLC analysis was performed on silica gel 60 $F_{254}$ plates (Merck), the compounds were detected by staining with 8% of phosphoric acid in water followed by heating at over 200° C. Column chromatography was carried out on silica gel 60 (0.2-0.063 mm, Merck) or Sephadex LH-20 (Amersham). $^1$H NMR spectra were acquired on a Bruker DRX-500 spectrometer. Chemical shifts are given in ppm (δ) relative to $CD_3OD$. Synthesis of activated 1,2-O-dioleoyl-sn-glycero-3-phosphatidylethanolamine (DOPE) and 1,2-O-distereoyl-sn-glycero-3-phosphatidylethanolamine (DSPE)(glycerophospholipids)

To a solution of bis(N-hydroxysuccinimidyl) adipate (A) (70 mg, 205 μmol) in dry N,N-dimethylformamide (1.5 ml) were added DOPE or DSPE (L) (40 μmol) in chloroform (1.5 ml) followed by triethylamine (7 μl). The mixture was kept for 2 h at room temperature, then neutralized with acetic acid and partially concentrated in vacuo.

Column chromatography (Sephadex LH-20, 1:1 chloroform-methanol, 0.2% acetic acid) of the residue yielded the activated lipid (A-L) (37 mg, 95%) as a colorless syrup; TLC (chloroform-methanol-water, 6:3:0.5): $R_f$=0.5 (DOPE-A), $R_f$=0.55 (DSPE-A).

$^1$H NMR ($CDCl_3/CD_3OD$, 2:1), δ:

DOPE-A—5.5 (m, 4H, 2×(—CH̲=CH̲—), 5.39 (m, 1H, —OCH$_2$—CH̲O—CH$_2$O—), 4.58 (dd, 1H, J=3.67, J=11.98, —CCOOHCH̲—CHO—CH$_2$O—), 4.34 (dd, 1H, J=6.61, J=11.98, —CCOOHCH̲—CHO—CH$_2$O—), 4.26 (m, 2H, PO—CH̲$_2$—CH$_2$—NH$_2$), 4.18 (m, 2H, —CH̲$_2$—OP), 3.62 (m, 2H, PO—CH$_2$—CH̲$_2$—NH$_2$), 3.00 (s, 4H, ONSuc), 2.8 (m, 2H, —CH̲$_2$—CO (Ad), 2.50 (m, 4H, 2×(—CH̲$_2$—CO), 2.42 (m, 2H, —CH̲$_2$—CO (Ad), 2.17 (m, 8H, 2×(—CH̲$_2$—CH=CH—CH̲$_2$—), 1.93 (m, 4H, COCH$_2$CH̲$_2$C H̲$_2$CH$_2$CO), 1.78 (m, 4H, 2×(COCH$_2$CH̲$_2$—), 1.43, 1.47 (2 bs, 40H, 20 CH$_2$), 1.04 (m, 6H, 2 CH$_3$).

DSPE-A—5.39 (m, 1H, —OCH$_2$—CH̲O—CH$_2$O—), 4.53 (dd, 1H, J=3.42, J=11.98, —CCOOHC H̲—CHO—CH$_2$O—), 4.33 (dd, 1H, J=6.87, J=11.98, —CCOOHCH̲—CHO—CH$_2$O—), 4.23 (m, 2H, PO—CH̲$_2$—CH$_2$—NH$_2$), 4.15 (m, 2H, —CH̲$_2$—OP), 3.61 (m, 2H, PO—CH$_2$—CH̲$_2$—NH$_2$), 3.00 (s, 4H, ONSuc), 2.81 (m, 2H, —CH̲$_2$—CO (Ad), 2.48 (m, 4H, 2×(—CH̲$_2$—CO), 2.42 (m, 2H, —CH̲$_2$—CO (Ad), 1.93 (m, 4H, COCH$_2$CH̲$_2$C H̲$_2$CH$_2$CO), 1.78 (m, 4H, 2×(COCH$_2$CH̲$_2$—), 1.43, 1.47 (2 bs, 40H, 20 CH$_2$), 1.04 (m, 6H, 2 CH$_3$).

Condensing Activated DOPE (or DSPE) with Aminopropylglycoside.

To a solution of activated DOPE (or DSPE) (A-L) (33 μmol) in N,N-dimethylformamide (1 ml) 30 μmol of Sug-S$_1$—NH$_2$ (F—S$_1$—NH$_2$) and 5 μl of triethylamine were added. For example, the Sug may be either the aminopropyl glycoside (F—S$_1$—NH$_2$) of either GalNAcα1-3(Fucα1-2) Galβ trisaccharide (A-glycotope) (F) or Galα1-3(Fucα1-2) Galβ trisaccharide (B-glycotope) (F).

The mixture was stirred for 2 h at room temperature. Column chromatography (Sephadex LH-20 in 1:1 chloroform-methanol followed by silica gel in ethyl acetate-isopropanol-water, 4:3:1 (v/v/v) of the mixture typically yielded 85-90% of the synthetic molecule construct, for example, $A_{tri}$-sp-Ad-DOPE (I) or $B_{tri}$-sp-Ad-DOPE (VI).

$^1$H NMR ($CDCl_3/CD_3OD$, 1:1), δ:

$A_{tri}$-sp-Ad-DOPE (I)—5.5 (m, 4H, 2×(—CH̲=CH̲—), 5.43-5.37 (m, 2H, H-1 (GalNHAc) and —OCH$_2$—C H̲O—CH$_2$O—), 5.32 (d, 1H, H-1, J=3.5H-1 Fuc), 2.50 (m, 4H, 2×(—CH̲$_2$—CO), 2.40 (m, 4H, COCH̲$_2$CH$_2$CH$_2$C H̲$_2$CO), 2.20 (m, 8H, 2×(—CH̲$_2$—CH=CH—CH̲$_2$—), 2.1 (s, 3H, NHAc), 1.92 (m, 2H, O—CH$_2$CH̲$_2$CH$_2$—NH), 1.8 (m, 8H, COCH$_2$CH̲$_2$CH$_2$CH$_2$CO and 2×(COCH$_2$CH̲$_2$—), 1.43, 1.47 (2 bs, 40H, 20 CH$_2$), 1.40 (d, 3H, J=6.6, CH$_3$ Fuc), 1.05 (m, 6H, 2 CH$_3$).

$A_{tri}$-spsp$_1$-Ad-DOPE (II)—5.5 (m, 4H, 2×(—CH̲=C H̲—), 5.43-5.37 [m, 2H, H-1 (GalNHAc) and —OCH$_2$—C H̲O—CH$_2$O—], 5.32 (d, 1H, H-1, J=3.6H-1 Fuc), 2.50 (m, 4H, 2×(—CH̲$_2$—CO), 2.40-2.32 (m, 6H, COCH̲$_2$CH$_2$CH$_2$C H̲$_2$CO and COCH̲$_2$— (sp$_1$), 2.18 [m, 8H, 2×(—C H̲=CH—CH=CH—CH̲$_2$—)], 2.1 (s, 3H, NHAc), 1.95 (m, 2H, O—CH$_2$CH̲$_2$CH$_2$—NH), 1.8 [m, 10H, COCH$_2$C H̲$_2$CH$_2$CO, 2×(COCH$_2$CH̲$_2$— . . . ), —COCH$_2$CH̲$_2$ (CH$_2$)$_3$NH—], 1.68 (m, 2H, CO(CH$_2$)$_3$CH̲$_2$CH$_2$NH—), 1.43, 1.47 (2 bs, 42H, 22 CH$_2$), 1.37 (d, 3H, J=5.6, CH$_3$ Fuc), 1.05 (m, 6H, 2 CH$_3$).

$A_{tri}$-sp-Ad-DSPE (III)—5.42-5.38 (m, 2H, H-1 (GalN-HAc) and —OCH$_2$—CH̲O—CH$_2$O—), 5.31 (d, 1H, H-1, J=3.5H-1 Fuc), 2.48 [m, 4H, 2×(—CH̲$_2$—CO)], 2.42 (m, 4H, COCH̲$_2$CH$_2$CH$_2$CH̲$_2$CO), 2.18 (s, 3H, NHAc), 1.95 (m, 2H, O—CH$_2$CH̲$_2$CH$_2$—NH), 1.8 [m, 8H, COCH$_2$CH̲$_2$C H̲$_2$CH$_2$CO and 2×(COCH$_2$CH̲$_2$—)], 1.43, 1.47 (2 bs, 56H, 28 CH$_2$), 1.38 (d, 3H, J=6.6, CH$_3$ Fuc), 1.05 (m, 6H, 2 CH$_3$).

$B_{tri}$-sp-Ad-DOPE (VI)—5.5 (m, 4H, 2×(—CH̲=CH̲—), 5.42-5.38 [m, 2H, H-1 (Gal) and —OCH$_2$—C H̲O—CH$_2$O—], 5.31 (d, 1H, J=3.7, H-1 Fuc), 2.48 [m, 4H, 2×(—CH̲$_2$—CO)], 2.39 (m, 4H, COCH̲$_2$CH$_2$CH$_2$C H̲$_2$CO), 2.18 [m, 8H, 2×(—CH̲$_2$—CH=CH—CH̲$_2$—)], 1.93 (m, 2H, O—CH$_2$CH̲$_2$CH$_2$—NH), 1.8 [m, 8H, COCH$_2$CH̲$_2$C H̲$_2$CH$_2$CO and 2×(COCH$_2$CH̲$_2$—)], 1.43, 1.47 (2 bs, 40H, 20 CH$_2$), 1.36 (d, 3H, J=6.6, CH$_3$ Fuc), 1.05 (m, 6H, 2 CH$_3$).

$H_{tri}$-sp-Ad-DOPE (VII)—5.5 [m, 4H, 2×(—CH̲=CH̲—)], 5.4 (m, 1H, —OCH$_2$—CH̲O—CH$_2$O—), 5.35 (d, 1H, H-1, J=3.2, H-1 Fuc), 4.65, 4.54 (2 d, J=7.4, J=8.6, H-1 Gal, H-1 GlcNHAc), 4.46 (dd, 1H J=3.18, J=12, —CCOO HCH̲—CHO—CH$_2$O—), 4.38-4.28 (m, 2H, H-5 Fuc, CCOOHCH̲—CHO—CH$_2$O—), 2.48 [m, 4H, 2×(—C H̲$_2$—CO)], 2.40 (m, 4H, COCH̲$_2$CH$_2$CH$_2$CH̲$_2$CO), 2.18 [m, 8H, 2×(—CH̲$_2$—CH=CH—CH̲$_2$—)], 2.08 (s, 3H, NHAc), 1.92 (m, 2H, O—CH$_2$CH̲$_2$CH$_2$—NH), 1.82-1.72 [m, 8H, COCH$_2$CH̲$_2$CH̲$_2$CH$_2$CO and 2×(COCH$_2$CH̲$_2$—)], 1.48, 1.45 (2 bs, 40H, 20 CH$_2$), 1.39 (d, 3H, J=6.5, CH$_3$ Fuc), 1.05 (m, 6H, 2 CH$_3$).

$H_{di}$-sp-Ad-DOPE (VIII)—5.49 (m, 4H, 2×(—CH̲=C H̲—), 5.37 (m, 1H, —OCH$_2$—CH̲O—CH$_2$O—), 5.24 (d, 1H, H-1, J=2.95, H-1 Fuc), 4.46 (d, J=7.34, H-1 Gal), 2.48 [m, 4H, 2×(—CH̲$_2$—CO)], 2.42-2.35 (m, 4H, COCH̲$_2$CH$_2$CH$_2$C H̲$_2$CO), 2.17 [m, 8H, 2×(—CH̲$_2$—CH=CH—CH̲$_2$—)], 1.95 (m, 2H, O—CH$_2$CH̲$_2$CH$_2$—NH), 1.81-1.74 [m, 8H, COCH$_2$CH̲$_2$CH̲$_2$CH$_2$CO and 2×(COCH$_2$CH̲$_2$—)], 1.45, 1.41 (2 bs, 40H, 20 CH$_2$), 1.39 (d, 3H, J=6.5, CH$_3$ Fuc), 1.03 (m, 6H, 2 CH$_3$).

Galβ-sp-Ad-DOPE (IX)—5.51 [m, 4H, 2×(—CH̲=C H̲—)], 5.4 (m, 1H, —OCH$_2$—CH̲O—CH$_2$O—), 4.61 (dd,

1H J=3.18, J=12, —CCOOHCH—CHO—CH$_2$O—), 4.41 (d, J=7.8, H–1 Gal), 4.37 (dd, 1H, J=6.6, J=12, —CCOOHCH—CHO—CH$_2$O—), 2.50 [m, 4H, 2×(—CH$_2$—CO)], 2.40 (m, 4H, COCH$_2$CH$_2$CH$_2$CO), 2.20 [m, 8H, 2×(—CH$_2$—CH═CH—CH$_2$—)], 1.97 (m, 2H, O—CH$_2$CH$_2$CH$_2$—NH), 1.82-1.72 [m, 8H, COCH$_2$CH$_2$CH$_2$CH$_2$CO and 2×(COCH$_2$CH$_2$—)], 1.48, 1.45 (2 bs, 40H, 20 CH$_2$), 1.05 (m, 6H, 2 CH$_3$).

Example 2

Solubility of Synthetic Glycolipids

For use in the transformation of cells the first criterion that synthetic glycolipids must satisfy is that they are soluble in aqueous solvents, e.g. phosphate buffered saline. A number of techniques, including heat and/or sonication, were employed initially in order to maximise the solubility of the synthetic glycolipids tested (Table 21).

The synthetic glycolipid must also be able to insert into the membrane and be recognisable to the appropriate antibody for transformation to be detected by agglutination. Initial tests on the molecules were to establish solubility and thus eliminate those molecules that were unsuitable for use in the transformation of cells.

The results of these initial tests are provided in Table 22.

TABLE 21

The range of synthetic glycolipid molecules tested.

DOPE Lipid Tails:

B$_{tri}$-sp-Ad-DOPE (VI)
A$_{tri}$-sp-Ad-DOPE (I)
Galβ-sp-Ad-DOPE (IX)
H$_{di}$-sp-Ad-DOPE (VIII)
H$_{tri}$-sp-Ad-DOPE (VII)
A$_{tri}$-spsp$_1$-Ad-DOPE (II)
B$_{tri}$-PAA-DOPE (V)

Different Lipid Tails:

A$_{tri}$-sp-lipid (IV)
A$_{tri}$-sp-Ad-DSPE (III)

TABLE 22

Solubility of synthetic glycolipids in hot PBS and transformation ability.

| Synthetic | Water solubility | Detectable transformation ability |
|---|---|---|
| A$_{tri}$-sp-lipid (IV) | No | No |
| B$_{tri}$-PAA-DOPE (V) | No | No |
| B$_{tri}$-sp-Ad-DOPE (VI) | Yes | Yes |
| A$_{tri}$-sp-Ad-DOPE (I) | Yes | Yes |
| Galβ-sp-Ad-DOPE (IX) | Yes | No |
| H$_{di}$-sp-Ad-DOPE (VIII) | Yes | No |

TABLE 22-continued

Solubility of synthetic glycolipids in hot PBS and transformation ability.

| Synthetic | Water solubility | Detectable transformation ability |
|---|---|---|
| H$_{tri}$-sp-Ad-DOPE (VII) | Yes | Yes |
| A$_{tri}$-spsp$_1$-Ad-DOPE (II) | Yes | Yes |
| A$_{tri}$-sp-Ad-DSPE (III) | Yes | Yes |

The lack of detectable transformation for Galβ-sp-Ad-DOPE (IX) and H$_{di}$-sp-Ad-DOPE (VIII) was thought to be due to the inability of the antibody to recognise the glycotope of these synthetic molecules. A$_{tri}$-sp-lipid (IV) has a single rather than a diacyl tail and it was proposed that there was no insertion of this synthetic molecule into the membrane bilayer.

Example 3

Low Temperature Transformation of RBCs by A$_{tri}$-Sp-Ad-DOPE (I) and B$_{tri}$-sp-Ad-DOPE (VI) Synthetic Glycolipids RBCs are healthier when stored at 4° C., and likewise are believed to be healthier when transformed at 4° C. It was not thought that a significant rate of insertion of the synthetic glycolipids would occur at 4° C. due to our previous studies (see Comparative Examples) and studies by others (Schwarzmann, 2000). These studies were performed with natural glycolipids. Surprisingly these studies did not predict the behaviour of the synthetic glycolipids of the invention.

Whilst not wishing to be bound by theory, in the studies of Schwarzmann the low rate of insertion of the natural glycolipids may be due to the physicochemical properties of the natural glycolipid tail; a sphingolipid and a fatty acid.

The diacyl tail of the glycolipid may be important in determining the rate of insertion. Certain diacyl tails may retain greater fluidity at lower temperatures. Alternatively, the domain of the plasma membrane into which the diacyl tail of these glycolipids inserts may retain this greater fluidity.

It is known that the sphingolipid tails of natural glycolipids congregate in rigid domains and these domains may not allow further incorporation of glycolipid at low temperatures. Synthetic glycolipids with cis-desaturated diacyl tails may be favoured for use.

Transformation of RBCs with synthetic glycolipids with different lipid tails was first evaluated (Tables 22 and 24).

TABLE 23

Antisera used to obtain results presented in Tables 24 to 27.

| Manufacturer | Catalogue ref | Batch number | Expiry date |
|---|---|---|---|
| Anti-A | | | |
| Albaclone, SNBTS | | Z0010770 | 12 Dec. 2004 |
| BioClone, OCD | Experimental reagent | 01102 | — |
| Anti-B | | | |
| Albaclone, SNBTS | | Z0110600 | 27 Apr. 2003 |
| BioClone, OCD | Experimental reagent | 01103 | — |

TABLE 24

Evaluation of insertion of different lipid tails by agglutination with the relevant antisera.

| Molecule | Anti-sera | Transformation solution (μg/mL) | | | | | | | | | |
|---|---|---|---|---|---|---|---|---|---|---|---|
| | | 1000 | 500 | 250 | 125 | 100 | 60 | 50 | 40 | 30 | 20 | 10 |
| $A_{tri}$-sp-Ad-DOPE (I) | Alba | | | | | | | w+ | w+ | 0 | 0 | 0 |
| | Bio | | | | | | | 2+ | 1+ | w+ | 0 | 0 |
| | Alba | | | 4+ | | 3+ | | 2-3+ | | | | 2+ |
| | Bio | | | 4+* | | 4+* | | 3+* | | | | 3+ |
| | DBA | 0 | | | | | | | | | | |
| $B_{tri}$-sp-Ad-DOPE (VI) | Alba | 3+ | | | | | | | | | | |
| | Bio | 3+ | | | | | | | | | | |
| | Alba | 2+ | 2+ | 1+ | 0 | | 0 | | | | | |
| | Bio | 3+ | 2+ | 1+ | 0 | | 0 | | | | | |
| $A_{tri}$-spsp$_1$-Ad-DOPE (III) | Alba | | | | | | | 0 | 0 | 0 | 0 | 0 |
| | Bio | | | | | | | 0 | 0 | 0 | 0 | 0 |
| | Alba | | | 4+ | | 3+ | | 2+ | | | | 2+ |
| | Bio | | | 4+* | | 3-4+* | | 3+* | | | | 2+ |
| | DBA | 0 | | | | | | | | | | |
| $A_{tri}$-sp-lipid (IV) | Alba | 0 | | | | | | | | | | |
| | Bio | 0 | | | | | | | | | | |
| $A_{tri}$-sp-Ad-DSPE (III) | Alba | | | | | | | 0 | 0 | 0 | 0 | 0 |
| | Bio | | | | | | | 0 | 0 | 0 | 0 | 0 |
| | Alba | | | 2-3+ | | 2-3+ | | 2+ | | | | 2+ |
| | Bio | | | 3+ | | 2-3+ | | 2+ | | | | 2+ |
| | DBA | 0 | | | | | | | | | | |

*splatter.

Transformation of RBCs with synthetic glycolipids $A_{tri}$-sp-Ad-DOPE (I) and $B_{tri}$-sp-Ad-DOPE (VI) at 4° C. was then evaluated (Tables 25 to 28). These transformations were directed towards the preparation of cells expressing low levels of A, B or A and B glycotopes ("weak A, B and AB cells").

For the preparation of weak A and B cells transformation solutions (20 μL, $A_{tri}$-sp-Ad-DOPE (I) at 0.08, 0.05 and 0.03 mg/mL, and $B_{tri}$-sp-Ad-DOPE (VI) at 0.6, 0.3, 0.15, 0.08, 0.05 and 0.03 mg/mL) in 1×PBS were mixed with washed, packed group O RBCs (60 μL).

For the preparation of weak AB cells transformation solutions (20 μL, $A_{tri}$-sp-Ad-DOPE (I) at 0.07, 0.06 and 0.05 mg/mL, and $B_{tri}$-sp-Ad-DOPE (VI) at 0.3, and 0.2 mg/mL) in 1×PBS were combined in block titre with washed, packed group O RBCs (60 μL). The combinations were: $A_{tri}$-sp-Ad-DOPE (I) at 0.07 mg/mL+$B_{tri}$-sp-Ad-DOPE (VI) at 0.3 mg/mL; $A_{tri}$-sp-Ad-DOPE (I) at 0.07 mg/mL+$B_{tri}$-sp-Ad-DOPE (VI) at 0.2 mg/mL; $A_{tri}$-sp-Ad-DOPE (I) at 0.06 mg/mL+$B_{tri}$-sp-Ad-DOPE (VI) at 0.3 mg/mL; $A_{tri}$-sp-Ad-DOPE (I) at 0.06 mg/mL+$B_{tri}$-sp-Ad-DOPE (VI) at 0.2 mg/mL; $A_{tri}$-sp-Ad-DOPE (I) at 0.05 mg/mL+$B_{tri}$-sp-Ad-DOPE (VI) at 0.3 mg/mL; and $A_{tri}$-sp-Ad-DOPE (I) 0.05+$B_{tri}$-sp-Ad-DOPE (VI) 0.2 mg/mL.

Cells and transformation solutions were placed in a 4° C. fridge. Pipette mixing was performed at intervals. Cells were removed for testing at intervals against the relevant antisera and were tested in both washed and unwashed states (i.e. washed samples had the transformation solution removed).

After 48 hours Celpresol™ was added to the cells so that the final cells:non-cells ratio was 3:5 (v/v). The cells continued to be tested at intervals. Testing was discontinued after 10 days because cells turned brown.

This discolouration could be attributed to a number of factors including: cells were already 21 days old when transformed; 48 hour transformation was in PBS not Celpresol™ so cells stressed for this time; and cells may have been mishandled in transit between the transforming and testing laboratories. This may be mitigated by transformation of the cells in Celpresol™ as opposed to PBS.

TABLE 25

Diamed results of weak A RBCs transformed at 4° C. against anti-A.

| | $A_{tri}$-sp-Ad-DOPE (I) (mg/mL) | | | | | |
|---|---|---|---|---|---|---|
| | Washed | | | unwashed | | |
| Time | 0.08 | 0.05 | 0.03 | 0.08 | 0.05 | 0.03 |
| 2 hrs | 0 | 0 | 0 | 0 | 0 | 0 |
| 4 hrs | 1+ | 0 | 0 | 2+ | 0 | 0 |
| 6 hrs | 2+ | 0 | 0 | 2+ | 0 | 0 |
| 8 hrs | 2+ | 0 | 0 | 2-3+ | 0 | 0 |
| 12 hrs | 2-3+ | 0 | 0 | 3+ | 1+ | 0 |
| 24 hrs | 3-4+ | 1+ | 0 | 3-4+ | 2+ | 0 |
| 30.5 hr | 3-4+ | 1+ | 0 | 3-4+ | 2+ | 0 |
| 48 hrs | 4+ | 2+ | 0 | 4+ | 2+ | 0 |
| 72 hrs | 4+ | 2+ | 0 | 4+ | 2-3+ | 0 |
| 96 hrs | 4+ | 2-3+ | 0 | 4+ | 2-3+ | 0 |
| Day 7 | | | | 3-4+ | 2+ | 0 |
| Day 10 | | | | 3-4+ | 2+ | 0 |

TABLE 26

Diamed results of weak B RBCs transformed at 4° C. against anti-B.

| | $B_{tri}$-sp-Ad-DOPE (VI) (mg/mL) | | | | | |
|---|---|---|---|---|---|---|
| | washed | | | unwashed | | |
| Time | 0.6 | 0.3 | 0.15 | 0.6 | 0.3 | 0.15 |
| 2 hrs | 0 | 0 | 0 | 0 | 0 | 0 |
| 4 hrs | 0 | 0 | 0 | 1+ | 0 | 0 |
| 6 hrs | w+ | 0 | 0 | 1+ | 0 | 0 |
| 8 hrs | 2+ | 0 | 0 | 2+ | w+ | 0 |
| 12 hrs | 2+ | w+ | 0 | 2-3+ | 2+ | 0 |
| 24 hrs | 4+ | 3+ | 2+ | 4+ | 3+ | 2+ |
| 30.5 hr | 4+ | 2-3+ | 0 | 4+ | 2-3+ | w+ |
| 48 hrs | 4+ | 3+ | 1+ | 4+ | 3+ | 2+ |
| 72 hrs | 4+ | 4+ | 2+ | 4+ | 4+ | 2+ |

TABLE 26-continued

Diamed results of weak B RBCs transformed at 4° C. against anti-B.

| | $B_{tri}$-sp-Ad-DOPE (VI) (mg/mL) | | | | | |
|---|---|---|---|---|---|---|
| | washed | | | unwashed | | |
| Time | 0.6 | 0.3 | 0.15 | 0.6 | 0.3 | 0.15 |
| 96 hrs | 4+ | 3-4+ | 2-3+ | 4+ | 3-4+ | 2-3+ |
| Day 7 | | | | 4+ | 2-3+ | 0 |
| Day 10 | | | | 4+ | 2+ | 0 |

TABLE 27

Diamed results of weak AB RBCs transformed at 4° C. in block titre against anti-A.

| | $B_{tri}$-sp-Ad-DOPE (VI) | $A_{tri}$-sp-Ad-DOPE (I) (mg/mL) | | | | | |
|---|---|---|---|---|---|---|---|
| | | washed | | | unwashed | | |
| Day | (mg/mL) | 0.07 | 0.06 | 0.05 | 0.07 | 0.06 | 0.05 |
| 1 | 0.3 | 2+ | 1-2+ | w+ | 2-3+ | 2+ | 1+ |
|   | 0.2 | 2+ | 1-2+ | 0 | 2-3+ | 2+ | 1+ |
| 5 | 0.3 | 2+ | 1-2+ | 1+ | 2-3+ | 2+ | 1-2+ |
|   | 0.2 | 2+ | 1-2+ | w+ | 2-3+ | 2+ | 1-2+ |
| 8 | 0.3 | | | | 2-3+ | 2+ | 2+ |
|   | 0.2 | | | | 2-3+ | 2+ | 1-2+ |

TABLE 28

Diamed results of weak AB RBCs transformed at 4° C. in block titre against anti-B.

| | $B_{tri}$-sp-Ad-DOPE (VI) | $A_{tri}$-sp-Ad-DOPE (I) (mg/mL) | | | | | |
|---|---|---|---|---|---|---|---|
| | | washed | | | unwashed | | |
| Day | (mg/mL) | 0.07 | 0.06 | 0.05 | 0.07 | 0.06 | 0.05 |
| 1 | 0.3 | 3+ | 3+ | 2+ | 3+ | 3+ | 2-3+ |
|   | 0.2 | 1+ | 1-2+ | 0 | 2+ | 2+ | 1-2+ |
| 5 | 0.3 | 2+ | 2+ | 1+ | 2+ | 2+ | 2+ |
|   | 0.2 | 0 | w+ | vw | 1+ | w+ | vw |
| 8 | 0.3 | | | | 2+ | 2+ | 2+ |
|   | 0.2 | | | | 1+ | 1+ | 0 |

Example 4

Insertion Efficiency of Transformation of RBCs by $A_{tri}$-sp-Ad-DOPE (I) and $B_{tri}$-sp-Ad-DOPE (VI) Synthetic Glycolipids The post-transformation supernatant solutions (from $A_{tri}$-sp-Ad-DOPE (I) at 0.08 mg/mL, 0.05 mg/mL and 0.03 mg/mL, and $B_{tri}$-sp-Ad-DOPE (VI) at 0.6 mg/mL, 20 μL) were added neat and in a 1:2 dilution to washed, packed RBCs (60 μL). The tubes were incubated in a 37° C. waterbath for one hour, with mixing taking place every 15 minutes.

The transformed RBCs were washed 3× with PBS and then suspended in Cellstab™ at the appropriate concentration for serology testing.

TABLE 29

| Tube serology | |
|---|---|
| Pre-trans conc (mg/mL) | Score |
| $A_{tri}$-sp-Ad-DOPE (I) at 0.08 | 0 |
| 1:2 of $A_{tri}$-sp-Ad-DOPE (I) at 0.08 | 0 |
| $A_{tri}$-sp-Ad-DOPE (I) at 0.05 | 0 |
| 1:2 of $A_{tri}$-sp-Ad-DOPE (I) at 0.05 | 0 |
| $A_{tri}$-sp-Ad-DOPE (I) at 0.03 | 0 |
| 1:2 of $A_{tri}$-sp-Ad-DOPE (I) at 0.03 | 0 |
| $B_{tri}$-sp-Ad-DOPE (VI) at 0.60 | vw+ |
| 1:2 of $B_{tri}$-sp-Ad-DOPE (VI) at 0.60 | 0 |

The score given by the post-transformation supernatant solution (from the 0.08 mg/mL pre-transformation solution) is not even that of the 0.03 mg/mL transformation solution in the first pass (w+). These results indicate that >75% of the molecules are inserted into the RBC membrane on the first pass.

In addition, the post-transformation solutions were concentrated 20× and compared in parallel with the transformation solutions of known concentration. Only the post-transformation solutions derived from the 0.08 mg/mL $A_{tri}$-sp-Ad-DOPE (I) and 0.6 mg/mL $B_{tri}$-sp-Ad-DOPE (VI) solutions were tested.

Post-transformation solutions (20 μL) were dialysed (pore size 500 Da) against de-ionised water for 2 days. The samples were left to dry in a fumehood for 10 days. At the end of this time they were transferred into a rotavapor flask and set on the rotavapor to rotate under vacuum with no heat overnight.

Samples were dried in a water bath at 40° C. and washed over into smaller vessels with chloroform-methanol 2:1 leaving significant amounts of dried cellular material. The chloroform-methanol 2:1 washings were dried down, washed over again into test-tubes with chloroform-methanol 2:1 and dried down. These samples were redissolved in 1 mL of 1×PBS and used for transformation experiments. The cellular material in the bottom of the flasks was washed out with water into another set of tubes.

The post-transformation solutions (from $A_{tri}$-sp-Ad-DOPE (I) at 0.08 mg/mL and $B_{tri}$-sp-Ad-DOPE (VI) at 0.6 mg/mL, 20 μL) were added to washed, packed RBCs (60 μL). In parallel, the transformation solutions ($A_{tri}$-sp-Ad-DOPE (I) at 0.08 mg/mL, 0.05 mg/mL and 0.03 mg/mL, and $B_{tri}$-sp-Ad-DOPE (VI) at 0.6 mg/mL, 20 μL) were added to washed, packed RBCs (60 μL).

The tubes were incubated in a 37° C. waterbath for one hour, with mixing taking place every 15 minutes. The transformed RBCs were washed 3× with PBS and then suspended in Cellstab™ at the appropriate concentration for serology testing.

TABLE 30

| Diamed serology | |
|---|---|
| conc (mg/mL) | Score |
| $A_{tri}$-sp-Ad-DOPE (I) at 0.08 | 3+ |
| $A_{tri}$-sp-Ad-DOPE (I) at 0.05 | 2+ |
| $A_{tri}$-sp-Ad-DOPE (I) at 0.03 | 1+ |
| From $A_{tri}$-sp-Ad-DOPE (I) at 0.08 | 0 |
| $B_{tri}$-sp-Ad-DOPE (VI) at 0.60 | 4+ |
| From $B_{tri}$-sp-Ad-DOPE (VI) at 0.60 | 0 |

These results suggest that there are not enough molecules in the post-transformation solution, even when concentrated 20×, to be detected by serology.

Example 5

Transformation of Murine RBCs by $H_{tri}$-sp-Ad-DOPE (VII) Synthetic Glycolipid Mouse cells were transformed at 37° C. for 1 hour.

TABLE 31

Anti-H reagents used for results in Tables 32 and 33.

| Antisera | Manufacturer | Batch |
|---|---|---|
| Anti-H IgM | Japanese Red Cross | HIRO-75 |
| UEA | Lorne Laboratories | 11549E D.O.E. 06.2004 |
| Bio-UEA | EY Labs | 201105-2 |

TABLE 32

Tube Serology.

| | H Antisera | | | |
|---|---|---|---|---|
| | | UEA | | |
| Cells | IgM | T = 0 | T = 20 | Bio-UEA |
| Mouse RBCs (−control) | 0 | 0 | 0 | |
| Mouse RBCs + 0.01 mg/mL $H_{tri}$-sp-Ad-DOPE (VII) | 0 | | | |
| Mouse RBCs + 0.05 mg/mL $H_{tri}$-sp-Ad-DOPE (VII) | 1+ | | | |
| Mouse RBCs + 0.1 mg/mL $H_{tri}$-sp-Ad-DOPE (VII) | 3+ | | | |
| Mouse RBCs + 0.25 mg/mL $H_{tri}$-sp-Ad-DOPE (VII) | 4+ | | | 1+ |
| Mouse RBCs + 1 mg/mL $H_{tri}$-sp-Ad-DOPE (VII) | | 2+ | | 2+ |
| Human O RBCs (+control) | 4+ | 1+ | 2/3+ | 4+ |

TABLE 33

Diamed

| Cells | Score |
|---|---|
| Mouse RBCs + 0.01 mg/mL $H_{tri}$-sp-Ad-DOPE (VII) | 0 |
| Mouse RBCs + 0.05 mg/mL $H_{tri}$-sp-Ad-DOPE (VII) | 0 |
| Mouse RBCs + 0.1 mg/mL $H_{tri}$-sp-Ad-DOPE (VII) | 2+ |
| Mouse RBCs + 0.25 mg/mL $H_{tri}$-sp-Ad-DOPE (VII) | 3+ |

Example 6

Transformation of RBCs by Filtered $A_{tri}$-sp-Ad-DOPE (I) Synthetic Glycolipid Some $A_{tri}$-sp-Ad-DOPE (I) had been sterile-filtered through a 0.2 μm filter. To investigate whether transformation would be the same with this product a comparative trial was done.

TABLE 34

Anti-A used for results presented in Table 35.

| Manufacturer | Catalogue ref | Batch number | Expiry date |
|---|---|---|---|
| BioClone, OCD | Experimental reagent | 01102 | — |

TABLE 35

Column agglutination of A RBCs transformed with varying concentrations of sterile-filtered vs unfiltered $A_{tri}$-sp-Ad-DOPE (I).

| Concentration (mg/mL) | Sterile-filtered $A_{tri}$-sp-Ad-DOPE (I) | Unfiltered $A_{tri}$-sp-Ad-DOPE (I) |
|---|---|---|
| 0.2 | 4+ | 4+ |
| 0.1 | 4+ | 3-4+ |
| 0.05 | 2-3+ | 2-3+ |
| 0.01 | 0 | 0 |
| Control 37° C. | 0 | |
| Control 25° C. | 0 | |

These results show no significant difference between the two preparations of $A_{tri}$-sp-Ad-DOPE (I) and suggests that filtration through a 0.2 μM filter did not remove molecules or change the composition or properties of the fluid to the point that transformation was affected.

Example 7

Storage of Transformed Cells

To investigate whether storage at 4° C. or 37° C. changed the agglutination results of $A_{tri}$-sp-Ad-DOPE (I) and natural A glycolipid transformed O RBCs, identified as "Syn-A" and "Nat-A" cells respectively, were divided in two and suspended to 5% in Cellstab™.

One set of cells was stored at 4° C. and the other set of cells was stored at 37° C. in a waterbath. Agglutination of the stored transformed cells was assessed (Table 36).

TABLE 36

| Time (hours) | Platform | Temp (° C.) | Syn-A $A_{tri}$-sp-Ad-DOPE (I) at 0.1 mg/mL | Nat-A At 1 mg/mL | Nat-A At 10 mg/mL | Control |
|---|---|---|---|---|---|---|
| 0 | Tube | | 3+ | 0 | 1-2+ | 0 |
| 20 | Column | 4 | 4+ | 0 | 3+ | 0 |
| | | 37 | 4+ | 0 | 3+ | 0 |
| 44 | Column | 4 | 4+ | | 3+ | 0 |
| | | 37 | 4+ | | 3+ | 0 |

Example 8

RBC Transformation with A- and B-Antigen Synthetic Glycolipids with Different Non-Carbohydrate Structures The water soluble synthetic glycolipids designated $A_{tri}$-sp-Ad-DOPE (I), $A_{tri}$-sp$_1$sp$_2$-Ad-DOPE (II), $A_{tri}$-sp-Ad-DSPE (III), and $B_{tri}$-sp-Ad-DOPE (VI) were prepared according to the method described in Example 1 with necessary modifications.

Washed packed group O red blood cells (RBCs) (3 parts by volume) and the synthetic glycolipid solution (1 part by volume, varying concentrations) were added to an eppendorf tube. The tube was incubated in a 37° C. waterbath for one hour, mixing every 15 minutes. The transformed RBCs were washed 3× with PBS and then suspended in Cellstab™ at the appropriate concentration for serology testing.

Tube serology and Diamed gel-card results for RBCs transformed with the different synthetic molecule constructs are provided in Table 38. Results for the stability of the RBCs transformed with the different synthetic glycolipids at different concentrations are provided in Tables 39 to 44.

TABLE 37

Antisera used for results presented in Tables 38 to 44.

| Antisera | Manufacturer | Batch |
|---|---|---|
| Albaclone anti-A | SNBTS | Z0010770 - D.O.E 12.12.04 |
| Bioclone anti-A | Ortho Diagnostics | 01102 - D.O.M 16.05.02 |
| Albaclone anti-B | SNBTS | Z0110670 - D.O.E 12.12.04 |
| Bioclone anti-B | Ortho Diagnostics | 01103 - D.O.M 16.05.02 |

TABLE 38

Comparison of transformation of RBCs using A-antigen synthetic glycolipids at different concentrations.

| Synthetic | Conc mg/mL | Albaclone anti-A Tube | Albaclone anti-A Diamed | Bioclone anti-A Tube | Bioclone anti-A Diamed |
|---|---|---|---|---|---|
| $A_{tri}$-sp-Ad-DOPE (I) | 0.25 | n.d. | 4+ | n.d. | 4+ |
| | 0.1 | n.d. | 4+/3+ | n.d. | 4+/3+ |
| | 0.05 | w+ | 2+ | 2+ | 2+ |
| | 0.04 | w+ | n.d. | 1+ | n.d. |
| | 0.03 | 0 | n.d. | w+ | n.d. |
| | 0.02 | 0 | n.d. | 0 | n.d. |
| | 0.01 | 0 | 0 | 0 | 0 |
| $A_{tri}$-sp-Ad-DSPE (III) | 0.25 | n.d. | 0 | n.d. | 0 |
| | 0.1 | n.d. | 0 | n.d. | 0 |
| | 0.05 | 0 | 0 | 0 | 0 |
| | 0.04 | 0 | n.d. | 0 | n.d. |
| | 0.03 | 0 | n.d. | 0 | n.d. |
| | 0.02 | 0 | n.d. | 0 | n.d. |
| | 0.01 | 0 | 0 | 0 | 0 |
| $A_{tri}$-$sp_1sp_2$-Ad-DOPE (II) | 0.25 | n.d. | 4+ | n.d. | 4+ |
| | 0.1 | n.d. | 4+ | n.d. | 4+/3+ |
| | 0.05 | 0 | 3+ | 0 | 3+ |
| | 0.04 | 0 | n.d. | 0 | n.d. |
| | 0.03 | 0 | n.d. | 0 | n.d. |
| | 0.02 | 0 | n.d. | 0 | n.d. |
| | 0.01 | 0 | 0 | 0 | 0 |
| Incubated control | — | 0 | n.d. | 0 | n.d. |
| Bench control | — | 0 | n.d. | 0 | n.d. |

Abbreviations: n.d. Not determined

TABLE 39

Stability trial of RBCs transformed with $A_{tri}$-sp-Ad-DOPE (I) at high concentrations (1 mg/mL, 0.5 mg/mL and 0.25 mg/mL). Agglutination by manual tube serology.

| Day | Cell storage solution | Albaclone anti-A 1 | 0.5 | 0.25 | Bioclone anti-A 1 | 0.5 | 0.25 |
|---|---|---|---|---|---|---|---|
| 2 | Alsevers | 4+ | 4+ | 4+ | 4+² | 4+² | 4+² |
| | Cellstab ™ | 4+ | 4+ | 3+ | 4+² | 4+² | 4+² |
| 10 | Alsevers | 3+ | 2+ | 2+ | 4+² | 4+² | 3+ |
| | Cellstab ™ | 4+² | 3+² | 2+ | 4+² | 4+² | 4+² |
| 17 | Alsevers | 4+ | 4+ | 4+ | 4+² | 4+² | 4+² |
| | Cellstab ™ | 4+ | 4+ | 4+ | 4+² | 4+² | 4+² |
| 24 | Alsevers | 4+ | 4+ | 4+ | 4+ | 4+ | 4+ |
| | Cellstab ™ | 4+ | 4+ | 4+ | 4+² | 4+ | 4+ |

Abbreviations: ²splatter

TABLE 40

Stability trial of RBCs transformed with $A_{tri}$-sp-Ad-DOPE (I) at low concentrations (0.1 mg/mL, 0.05 mg/mL and 0.025 mg/mL). Agglutination by manual tube serology.

| Day | Cell storage solution | Albaclone anti-A 0.1 | 0.05 | 0.025 | Bioclone anti-A 0.1 | 0.05 | 0.025 |
|---|---|---|---|---|---|---|---|
| 2 | Alsevers | 3+/2+ | 1+ | 1+/w+ | 2+ | 2+/1+ | 1+ |
| | Cellstab ™ | 3+/2+ | 2+ | 1+ | 3+/2+ | 3+/2+ | 2+ |
| 8 | Alsevers | 2+ | 1+ | w+ | 3+/2+ | 2+ | 2+ |
| | Cellstab ™ | 2+ | 1+/w+ | vw | 3+² | 2+ | 1+ |
| 15 | Alsevers | 2+ | 1+ | 0 | 3+ | 2+ | Vw |
| | Cellstab ™ | 4+ | w+ | 0 | 4+ | 4+ | 1+ |
| 22 | Alsevers | 2+ | 2+ | 0 | 3+ | 2+ | w+ |
| | Cellstab ™ | 4+ | 4+ | 1+ | 4+ | 4+ | 1+ |
| 44 | Alsevers | n.d. | n.d. | n.d. | n.d. | n.d. | n.d. |
| | Cellstab ™ | 4+ | 2+ | w+ | 4+ | 2+ | w+ |

Abbreviations: n.d. Not determined
²splatter

TABLE 41

Stability trial of RBCs transformed with $A_{tri}$-sp-Ad-DOPE (I) at high concentrations (1 mg/mL, 0.5 mg/mL and 0.25 mg/mL). Agglutination in Diamed gel-cards.

| Day | Cell storage solution | Albaclone anti-A 1 | 0.5 | 0.25 | Bioclone anti-A 1 | 0.5 | 0.25 |
|---|---|---|---|---|---|---|---|
| 2 | Alsevers | 4+ | 4+ | 4+ | 4+ | 4+ | 4+ |
| | Cellstab ™ | 4+ | 4+ | 4+ | 4+ | 4+ | 4+ |
| 10 | Alsevers | 4+ | 4+ | 4+ | 4+ | 4+ | 4+ |
| | Cellstab ™ | 4+ | 4+ | 4+ | 4+ | 4+ | 4+ |
| 17 | Alsevers | 4+ | 4+ | 4+ | 4+ | 4+ | 4+ |
| | Cellstab ™ | 4+ | 4+ | 4+ | 4+ | 4+ | 4+ |
| 24 | Alsevers | 4+ | 4+ | 4+ | 4+ | 4+ | 4+ |
| | Cellstab ™ | 4+ | 4+ | 4+ | 4+ | 4+ | 4+ |
| 45 | Alsevers | 4+ | 4+ | 4+ | 4+ | 4+ | 4+ |
| | Cellstab ™ | 4+ | 4+ | 4+ | 4+ | 4+ | 4+ |
| 59 | Alsevers | 4+ | 4+ | | 4+ | 4+ | |
| | Cellstab ™ | 4+ | 4+ | 4+ | 4+ | 4+ | 4+ |
| 73 | Alsevers | | | | | | |
| | Cellstab ™ | 4+ | 4+ | 4+ | 4+ | 4+ | 4+ |
| 88 | Alsevers | | | | | | |
| | Cellstab ™ | 4+ | 4+ | 4+ | 4+ | 4+ | 4+ |

Where there were insufficient cells for testing, blank spaces have been left.

TABLE 42

Stability trial of RBCs transformed with $A_{tri}$-sp-Ad-DOPE (I) at low concentrations (0.1 mg/mL, 0.05 mg/mL and 0.025 mg/mL). Agglutination in Diamed gel-cards.

| Day | Cell storage solution | Albaclone anti-A Concentration of Transformation Solution (mg/mL) | | | Bioclone anti-A Concentration of Transformation Solution (mg/mL) | | |
|---|---|---|---|---|---|---|---|
| | | 0.1 | 0.05 | 0.025 | 0.1 | 0.05 | 0.025 |
| 2 | Alsevers | 4+ | 2+ | 0 | 4+ | 3+ | 1+ |
| | Cellstab ™ | 4+ | 2+ | 0 | 4+ | 3+ | 1+ |
| 8 | Alsevers | 4+ | 3+ | 0 | 4+ | 4+ | 1+ |
| | Cellstab ™ | 4+ | 3+ | 0 | 4+ | 4+ | 1+ |
| 15 | Alsevers | 4+ | 2+ | 0 | 4+ | 3+/2+ | 1+ |
| | Cellstab ™ | 4+ | 4+ | 0 | 4+ | 4+ | 1+ |
| 22 | Alsevers | 4+ | 3+/2+ | 0 | 4+ | 3+ | w+ |
| | Cellstab ™ | 4+ | 4+ | 0 | 4+ | 4+ | 1+ |
| 29 | Alsevers | 4+ | 2+ | 0 | 4+ | 3+ | w+ |
| | Cellstab ™ | 4+ | 3+ | 0 | 4+ | 4+ | 2+ |
| 43 | Alsevers | 4+ | 3+ | w+ | 4+ | 4+ | 2+ |
| | Cellstab ™ | 4+ | 4+/3+ | 0 | 4+ | 4+ | 1+ |
| 50 | Alsevers | 4+ | 3+ | w+ | 4+ | 4+ | 2+ |
| | Cellstab ™ | 4+ | 3+ | 0 | 4+ | 4+ | 1+ |
| 57 | Alsevers | 4+ | 3+/2+ | | 4+ | 4+ | |
| | Cellstab ™ | 4+ | 3+ | 0 | 4+ | 3+ | w+ |
| 63 | Alsevers | | | | | | |
| | Cellstab ™ | 4+/3+ | 2+ | 0 | 4+ | 3+ | 0 |
| 71 | Alsevers | | | | | | |
| | Cellstab ™ | 4+/3+ | 2+ | 0 | 4+ | 3+ | 0 |
| 86 | Alsevers | | | | | | |
| | Cellstab ™ | 4+/3+ | 2+ | 0 | 4+ | 3+ | 0 |

Where there were insufficient cells for testing, blank spaces have been left.

TABLE 43

Stability trial of RBCs transformed with $B_{tri}$-sp-Ad-DOPE (VI) at high concentrations (1 mg/mL, 0.5 mg/mL and 0.25 mg/mL). Agglutination by manual tube serology.

| Day | Cell storage solution | Albaclone anti-B Concentration of Transformation Solution (mg/mL) | | | Bioclone anti-B Concentration of Transformation Solution (mg/mL) | | |
|---|---|---|---|---|---|---|---|
| | | 1 | 0.5 | 0.25 | 1 | 0.5 | 0.25 |
| 2 | Alsevers | 3+ | 3+ | 2+ | 2+ | 1+ | 1+ |
| | Cellstab ™ | 3+ | 2+ | 2+ | 2+ | 2+ | 1+ |
| 9 | Alsevers | 4+ | 4+ | 2+ | 4+ | 3+ | 2+ |
| | Cellstab ™ | 4+ | 4+ | 3+ | 4+ | 4+ | 2+ |
| 16 | Alsevers | 4+ | 4+ | 3+ | 4+ | 4+ | 2+ |
| | Cellstab ™ | 4+ | 4+ | 2+ | 4+ | 4+ | 2+ |
| 23 | Alsevers | 4+ | 4+ | 3+ | 4+ | 4+ | 3+ |
| | Cellstab ™ | 4+ | 4+ | 3+ | 4+ | 4+ | 3+ |
| 30 | Alsevers | 3+ | 3+ | 2+ | 2+ | 2+ | 2+ |
| | Cellstab ™ | 4+ | 3+ | 2+ | 3+² | 3+² | 2+ |
| 37 | Alsevers | 3+ | 2+ | 1+ | 3+ | 2+ | 1+ |
| | Cellstab ™ | 3+ | 3+ | 2+/1+ | 4+² | 3+ | 1+ |
| 44 | Alsevers | 4+ | 3+ | 1+ | 3+ | 3+ | w+ |
| | Cellstab ™ | 4+ | 4+ | n.d. | 4+ | 4+ | ‡ |
| 51 | Alsevers | 3+ | 3+ | 2+ | 4+ | 3+ | 2+ |
| | Cellstab ™ | 4+ | 4+ | n.d. | 4+ | 4+ | 2+ |

Abbreviations: ²splatter

TABLE 44

Stability trial of RBCs transformed with $B_{tri}$-sp-Ad-DOPE (VI) at high concentrations (1 mg/mL, 0.5 mg/mL and 0.25 mg/mL). Agglutination in Diamed gel-cards.

| Day | Cell storage solution | Albaclone anti-B Concentration of Transformation Solution (mg/mL) | | | Bioclone anti-B Concentration of Transformation Solution (mg/mL) | | |
|---|---|---|---|---|---|---|---|
| | | 1 | 0.5 | 0.25 | 1 | 0.5 | 0.25 |
| 2 | Alsevers | 4+ | 4+ | 2+ | 4+ | 4+ | 2+ |
| | Cellstab ™ | 4+ | 4+ | 2+ | 4+ | 4+ | 2+ |
| 9 | Alsevers | 4+ | 4+ | 2+ | 4+ | 4+ | 2+ |
| | Cellstab ™ | 4+ | 4+ | 3+ | 4+ | 4+ | 3+ |
| 16 | Alsevers | 4+ | 4+ | 2+ | 4+ | 4+ | 1+ |
| | Cellstab ™ | 4+ | 4+ | 3+ | 4+ | 4+ | 3+ |
| 23 | Alsevers | 4+ | 4+ | 3+ | 4+ | 4+ | 3+ |
| | Cellstab ™ | 4+ | 4+ | 3+ | 4+ | 4+ | 3+ |
| 30 | Alsevers | 4+ | 4+ | 3+ | 4+ | 4+ | 3+ |
| | Cellstab ™ | 4+ | 4+ | 3+ | 4+ | 4+ | 3+ |
| 37 | Alsevers | 4+ | 4+ | 3+ | 4+ | 4+ | 3+ |
| | Cellstab ™ | 4+ | 4+ | 3+ | 4+ | 4+ | 3+ |
| 44 | Alsevers | 4+ | 4+ | 2+ | 4+ | 4+ | 3+ |
| | Cellstab ™ | 4+ | 4+ | 3+ | 4+ | 4+ | 4+/3+ |
| 51 | Alsevers | 4+ | 4+ | 2+ | 4+ | 4+ | 3+ |
| | Cellstab ™ | 4+ | 4+ | 3+ | 4+ | 4+ | 3+ |
| 58 | Alsevers | 4+ | | 1+ | 4+ | | 2+ |
| | Cellstab ™ | 4+ | 4+ | 2+ | 4+ | 4+ | 2+ |
| 72 | Alsevers | 4+ | | 2+ | 4+ | | 3+ |
| | Cellstab ™ | 4+ | 4+ | 3+/2+ | 4+ | 4+ | 3+ |
| 87 | Alsevers | | | | | | |
| | Cellstab ™ | 4+ | 4+/3+ | 1+ | 4+ | 4+/3+ | 2+/1+ |
| 116 | Alsevers | | | | | | |
| | Cellstab ™ | 4+ | 3+ | 0 | 4+ | 4+/3+ | 1+ |

Where there were insufficient cells for testing, blank spaces have been left.

Example 9

Red Blood Cell Transformation with H-Antigen Synthetic Glycolipids

The water soluble synthetic glycolipids designated $H_{tri}$-sp-Ad-DOPE (VII), $H_{di}$-sp-Ad-DOPE (VIII) and Galβ-sp-Ad-DOPE (IX) were prepared according to the method described in Example 1 with necessary modifications.

Washed packed mouse RBCs (3 parts by volume) and the synthetic glycolipid solutions (1 part by volume of varying concentrations) were added to an eppendorf tube. The tube was incubated in a 37° C. waterbath for one hour, mixing every 15 minutes. The transformed RBCs were washed 3× with PBS and then suspended in Cellstab™ at the appropriate concentration for serology testing.

Tube serology and Diamed gel-card results for RBCs transformed with the different synthetic glycolipids are presented in Table 46. The results show that three sugars ($H_{tri}$) are required for detection by anti-H IgM, at least by the reagent used.

TABLE 45

Antisera used for results presented in Table 46.

| Antisera | Manufacturer | Batch |
|---|---|---|
| Anti-H IgM | Japanese Red Cross | HIRO-75 |
| UEA | Lorne Laboratories | 11549E D.O.E. 06.2004 |
| Bio-UEA | EY Labs | 201105-2 |

TABLE 46

Comparison of transformation of RBCs using H-antigen synthetic glycolipids with different glycotopes made to different concentrations.

| Synthetic | Conc mg/mL | IgM Tube | IgM Diamed | UEA Tube T0 | UEA Tube T20 | Bio-UEA Tube |
|---|---|---|---|---|---|---|
| $H_{tri}$-sp-Ad-DOPE (VII) | 1 | n.d. | n.d. | 2+ | n.d. | 2+ |
|  | 0.25 | 4+ | 3+ | n.d. | n.d. | 1+ |
|  | 0.1 | 3+ | 2+ | n.d. | n.d. | n.d. |
|  | 0.05 | 1+ | 0 | n.d. | n.d. | n.d. |
|  | 0.01 | 0 | 0 | n.d. | n.d. | n.d. |
| $H_{di}$-sp-Ad-DOPE (VIII) | 0.25 | 0 | n.d. | n.d. | n.d. | n.d. |
|  | 0.1 | 0 | n.d. | n.d. | n.d. | n.d. |
|  | 0.05 | 0 | n.d. | n.d. | n.d. | n.d. |
|  | 0.01 | 0 | n.d. | n.d. | n.d. | n.d. |
| Galβ-sp-Ad-DOPE (IX) | 0.25 | 0 | n.d. | n.d. | n.d. | n.d. |
|  | 0.1 | 0 | n.d. | n.d. | n.d. | n.d. |
|  | 0.05 | 0 | n.d. | n.d. | n.d. | n.d. |
|  | 0.01 | 0 | n.d. | n.d. | n.d. | n.d. |
| Human O cells | — | 4+ | n.d. | 1+ | 2/3+ | 4+ |
| Incubated control | — | 0 | n.d. | 0 | 0 | n.d. |
| Bench control | — | 0 | n.d. | n.d. | n.d. | n.d. |

Abbreviations: n.d. Not determined

Example 10

Insertion of $H_{di}$-sp-Ad-DOPE (VIII) and Galβ-sp-Ad-DOPE (IX) Synthetic Glycolipids into Murine Red Blood Cells The water soluble synthetic glycolipids designated $H_{di}$-sp-Ad-DOPE (VIII) and Galβ-sp-Ad-DOPE (IX) were prepared according to the method described in Example 1 with necessary modifications.

Murine RBCs were washed 3× in 1×PBS. 30 µl of packed RBCs were combined with 30 µl of $H_{di}$-sp-Ad-DOPE (VIII), and 30 µl of packed RBCs were combined with 30 µl Galβ-sp-Ad-DOPE (IX), respectively. Both synthetic molecule constructs were at a concentration of 1.0 mg/ml. 30 µl of 1×PBS was added to 30 µl of packed RBCs to act as the control group. Cells were incubated for 90 minutes in a 37° C. shaking water-bath. RBCs were washed 3× in 1×PBS.

Three groups of packed RBCs were incubated with an equal volume of lectin UEA-1 for 30 minutes at room temperature. The lectin was prepared in 1×PBS at a concentration of 0.1 mg/ml. 50 µl of a 3% cell suspension was spun for 15 seconds in an Immunofuge at low speed. Results were read by tube serology. The results are presented in Table 48. The results show that neither anti-H IgM nor UEA-1 detects two sugars ($H_{di}$).

TABLE 47

Antisera used for results presented in Table 48.

| Antisera | Manufacturer | Batch |
|---|---|---|
| Biotest anti-H | Biotest AG |  |
| UEA | EY Labs | 201105-2 |

TABLE 48

Murine RBCs transformed with Galβ-sp-Ad-DOPE or $H_{di}$-sp-Ad-DOPE, assessed by agglutination.

| Cell Type | Inserted Molecule | UEA-1 | Mouse IgM$^H$ |
|---|---|---|---|
| Murine RBC | Galβ (1 mg/ml) | 0 | n.d. |
| Murine RBC | $H_{di}$ (1 mg/ml) | 0 | 0 |
| Murine RBC | Control (PBS) | 0 | 0 |
| Human RBC | Control (PBS) | 4+ | 3+ |

Abbreviations: n.d. Not determined

Example 11

Preparation of Sensitivity Controls

The synthetic glycolipids of the invention may be used in the preparation of "sensitivity controls" (also referred to as "quality control cells", "serology controls", or "process controls") as described in the specification accompanying international application no. PCT/NZ02/00214 (WO 03/034074). The synthetic glycolipids provide the advantage that the transformation of the RBCs may be achieved at reduced temperatures.

RBC Transformation Solutions
Two stock solutions are used:
  Solution 1: 1 mg/mL $A_{tri}$-sp-Ad-DOPE (I) suspended in Celpresol™ solution.
  Solution 2: 5 mg/mL $B_{tri}$-sp-Ad-DOPE (VI) suspended in Celpresol™ solution.

Glycolipids are manufactured in a white dry powder. Glycolipids in this form (enclosed in a sealed container under a controlled temperature) are stable for an indefinite period of time. The glycolipids are suspended in solution (e.g. Celpresol™) by weight in order to formulate the transformation solutions.

Once the transformation solutions are received at CSL, they are filtered (through a MILLEX®-GV 0.22µ filter unit) under aseptic conditions.

Processing of RBCs

RBC donations are processed using a continuous flow centrifuge washer under aseptic conditions. RBC donations are washed in buffered saline followed by Celpresol™ solution. The PCV of the RBC donations is measured on a Beckman Coulter AcT Diff analyser. The donations are then adjusted to a packed cell volume (PCV) of 50% with the addition of Celpresol™.

Transformation of RBCs to Provide "Weak AB Cells"

RBCs are washed in buffered saline and Celpresol™. The cells are suspended in Celpresol™ solution to a PCV of >50%. The PCV of red cells is measured using a Beckman Coulter AcT Diff. The mass of the red cell solution is weighed.

The amount of $A_{tri}$-sp-Ad-DOPE (I), $B_{tri}$-sp-Ad-DOPE (VI) and Celpresol™ for transformation is calculated using the following equations:

$$a = \frac{P \times F}{S}$$

$$b = \frac{P \times F}{S}$$

$$c = P - (1 - P) - a - b$$

where
- a = amount of $A_{tri}$-sp-Ad-DOPE (I) to be added per 1 mL of red cells (mL)
- b = amount of $B_{tri}$-sp-Ad-DOPE (VI) to be added per 1 mL of red cells (mL)
- c = amount of Celpresol™ to be added per 1 mL of red cells (mL) to dilute cells to 50% PCV
- P = PCV of red cell solution
- F = Final desired concentration of glycolipid
- S = Concentration of stock glycolipid solution To determine the amount of glycolipid and Celpresol™ to add to a bulk sample of red cells, multiply each of a, b and c by the red cell volume. Add $A_{tri}$-sp-Ad-DOPE (I), $B_{tri}$-sp-Ad-DOPE (VI) and Celpresol™ to the red cell bulk sample aseptically.

Incubate the sample for 3 hours at 20° C. under controlled temperature conditions and constant gentle agitation. At the end of the 3 hour period, aseptically remove a sample of red cells and test the sample to confirm transformation of the RBCs. Perform blood grouping using tube, tile and column agglutination technology (CAT) techniques.

Incubate the red cell sample for 3 hours at 2-8° C. under controlled temperature conditions and constant gentle agitation for 18 hours. At the end of the 3 hour period, aseptically remove a sample of red cells and test the sample to confirm transformation of the red cells. Perform blood grouping using tube, tile and CAT techniques.

Wash the transformed red cells using a continuous flow centrifuge method, under aseptic conditions using Celpresol™ solution. Measure the PCV of the washed red cells and adjust to 50% PCV by the addition of Celpresol™ solution.

Formulation and Dispensing

Aseptically combine a volume of the transformed RBCs with a volume of simulated plasma diluent (SPD). The plasma may contain monoclonal and polyclonal antibodies. Antibodies are selected according to the desired characteristics of the sensitivity controls. The plasma may additionally contain tartrazine and bovine serum albumin.

Blood grouping and antibody screening is performed on the bulk samples using tube, tile and CAT techniques. The transformed RBC-SPD blend is then aseptically dispensed into BD Vacutainer tubes and the tubes labelled accordingly.

Validation Testing

Weak AB cells produced by the use of synthetic glycolipids (designated $A_w B_w$ in Tables 51 to 53) were used to validate a range of testing platforms in parallel with naturally occurring weak A, weak B and weak AB cells.

TABLE 49

Reagents and cards used in validation testing.
Method Reagent
Tube Epiclone
Tile Epiclone

| Ref | Manufacturer and type | Batch | Expiry |
|---|---|---|---|
| CAT 1 | OCD BioVue ABD/Rev | ABR528A | 16 Jun. 2005 |
| CAT 2 | OCD BioVue ABD/Rev | ABR521A | 06 May 2006 |
| CAT 3 | OCD BioVue ABD/ABD | ACC255A | 24 May 2005 |
| CAT 4 | Diamed ID-MTS | 50092.10.02 | April 2005 |
| CAT 5 | Diamed ID-MTS Donor typing | 51051.05.04 | March 2005 |
| CAT 6 | Diamed ID-MTS Recipient typing | 50053.07.02 | April 2005 |
| CAT 7 | Diamed ID-MTS Cord typing | 50961.08.03 | July 2005 |

TABLE 50

Testing platform methodology for validation testing.

| Tile | 1 drop 3% cells, 2 drops reagent, 15 min @ RT in moist chamber. |
|---|---|
| Tube | 2 drops @ RT, 10 min. |
| ID-MTS | As per manufacturers instructions using Dil-2. |
| BioVue | As per manufacturers instructions using 0.8% RCD. |

TABLE 51

Validation results across all methods against anti-A.

| | | Testing platform | | | | | | | | |
|---|---|---|---|---|---|---|---|---|---|---|
| Cell | Type | Tube | Tile | CAT 1 | CAT 2 | CAT 3 | CAT 4 | CAT 5 | CAT 6 | CAT 7 |
| 1 | $A_x$ | w+ | 0 | 2+ | | 1+ | 0 | 0 | 0 | 0 |
| 2 | $A_x$ | w+ | 0 | 2+ | | 2+ | 0 | 0 | 0 | 0 |
| 3 | $A_1B$ | 4+ | 4+ | 4+ | 4+ | 4+ | 4+ | 4+ | 4+ | 4+ |
| 4 | $A_x$ | w+ | 0 | 2+ | | 2+ | 0 | 0 | 0 | 0 |
| 5 | $A_2B$ | 3+ | 3+ | 4+ | | 3+ | 3+ | 1+ | 2+ | 3+ |
| 6 | $A_x$ | w+ | 0 | 2+ | | 2+ | 0 | 0 | 0 | 0 |
| 7 | $A_x$ | 1+ | 0 | 2+ | | 2+ | 0 | 0 | 0 | 0 |
| 8 | $A_x$ | w+ | 0 | 2+ | | 2+ | 0 | 0 | 0 | 0 |
| 9 | $A_x$ | 0 | 0 | 1+ | | 1+ | 0 | 0 | 0 | 0 |
| 10 | $A_x$ | w+ | 0 | 2+ | | 2+ | 0 | 0 | 0 | 0 |
| 11 | $A_3$ | 4+ | 4+ | 4+ | | 3+ | 3+ | 1+ | 1+ | 3+ |
| 12 | $A_3B$ | 3+ | 3+ | 3+ | | 3+ | 2+ | w+ | w+ | 2+ |
| 13 | $B_3$ | 0 | 0 | 0 | 0 | 0 | 0 | 0 | 0 | 0 |
| 14 | $B_3$ | 0 | 0 | 0 | 0 | 0 | 0 | 0 | 0 | 0 |
| 15 | $A_w B_w$ | 2+ | 2+ | 2+ | 2+ | 2+ | 0 | 0 | 0 | 0 |

TABLE 52

Validation results across all methods against anti-B.

| | | Testing platform | | | | | | | | |
|---|---|---|---|---|---|---|---|---|---|---|
| Cell | Type | Tube | Tile | CAT 1 | CAT 2 | CAT 3 | CAT 4 | CAT 5 | CAT 6 | CAT 7 |
| 1 | $A_x$ | 0 | 0 | 0 | | 0 | 0 | 0 | 0 | 0 |
| 2 | $A_x$ | 0 | 0 | 0 | | 0 | 0 | 0 | 0 | 0 |
| 3 | $A_1B$ | 4+ | 4+ | 4+ | 4+ | 4+ | 4+ | 3+ | 3+ | 4+ |
| 4 | $A_x$ | 0 | 0 | 0 | | 0 | 0 | 0 | 0 | 0 |
| 5 | $A_2B$ | 4+ | 4+ | 4+ | | 4+ | 4+ | 3+ | 3+ | 4+ |
| 6 | $A_x$ | 0 | 0 | 0 | | 0 | 0 | 0 | 0 | 0 |
| 7 | $A_x$ | 0 | 0 | 0 | | 0 | 0 | 0 | 0 | 0 |
| 8 | $A_x$ | 0 | 0 | 0 | | 0 | 0 | 0 | 0 | 0 |
| 9 | $A_x$ | 0 | 0 | 0 | | 0 | 0 | 0 | 0 | 0 |
| 10 | $A_x$ | 0 | 0 | 0 | | 0 | 0 | 0 | 0 | 0 |
| 11 | $A_3$ | 0 | 0 | 0 | | 0 | 0 | 0 | 0 | 0 |
| 12 | $A_3B$ | 4+ | 4+ | 4+ | | 4+ | 4+ | 4+ | 4+ | 4+ |
| 13 | $B_3$ | 2+ | 2+ | 3+ | 2+ | 2+ | 2+ | 2+ | 2+ | 2+ |
| 14 | $B_3$ | 2+ | 2+ | 2+ | 2+ | 2+ | 2+ | 1+ | 1+ | 2+ |
| 15 | $A_wB_w$ | 3+ | 3+ | 1+ | 1+ | 1+ | 0 | 0 | 0 | 0 |

TABLE 53

Validation results across all methods against anti-AB.

| | | Testing platform | | | | | | | | |
|---|---|---|---|---|---|---|---|---|---|---|
| Cell | Type | Tube | Tile | CAT 1 | CAT 2 | CAT 3 | CAT 4 | CAT 5 | CAT 6 | CAT 7 |
| 1 | $A_x$ | 3+ | 2+ | | | | | | | 2+ |
| 2 | $A_x$ | 4+ | 2+ | | | | | | | 3+ |
| 3 | $A_1B$ | 4+ | 4+ | | | | | | | 4+ |
| 4 | $A_x$ | 3+ | 2+ | | | | | | | 3+ |
| 5 | $A_2B$ | 4+ | 4+ | | | | | | | 4+ |
| 6 | $A_x$ | 4+ | 4+ | | | | | | | 3+ |
| 7 | $A_x$ | 4+ | 4+ | | | | | | | 3+ |
| 8 | $A_x$ | 3+ | 4+ | | | | | | | 3+ |
| 9 | $A_x$ | 4+ | 2+ | | | | | | | 2+ |
| 10 | $A_x$ | 3+ | 4+ | | | | | | | 3+ |
| 11 | $A_3$ | 4+ | 4+ | | | | | | | 4+ |
| 12 | $A_3B$ | 4+ | 4+ | | | | | | | 4+ |
| 13 | $B_3$ | 2+ | 2+ | | | | | | | 2+ |
| 14 | $B_3$ | 2+ | 2+ | | | | | | | 2+ |
| 15 | $A_wB_w$ | 3+ | 3+ | | | | | | | 3+ |

Example 12

Attachment of Modified Embryos to Transformed Endometrial Cells

The ability to effect qualitative and quantitative differences in the cell surface antigens expressed by cell types other than RBCs was investigated. The ability to enhance the adhesion of embryos to endometrial cells was adopted as a model system.

The synthetic molecules may be used as synthetic membrane anchors and/or synthetic molecule constructs. Therefore, they may also be employed in the method of enhancing embryo implantation as described in international patent application no PCT/NZ2003/000059 (published as WO 03/087346) which is incorporated by reference.

Endometrial Cell Transformation
Insertion of Water Soluble Synthetic Molecule Construct A single cell suspension of endometrial epithelial cells was prepared. The endometrial cells were washed 3× by resuspending in CMF HBSS and centrifuging at 2000 rpm for 3 minutes. The washed cell preparation was resuspended in 50 μl of M2.

Micro-centrifuge tubes each containing a 50 μl solution of 5M/ml endometrial cells were prepared. To separate tubes of endometrial cells 50 μl of synthetic glycolipids $A_{tri}$-sp-Ad-DOPE (I) or $B_{tri}$-sp-Ad-DOPE A (VI), or 50 μl M2 were added to the control cells. The cells were incubated for 90 minutes at 37° C. on a mixer. The endometrial cells were washed 3× by resuspending in CMF HBSS media and centrifuging at 2000 rpm for 3 minutes. The washed cell preparation was resuspended in 50 μl of M2.

Test for Insertion Using Fluorescent Probe:

50 μl of corresponding primary murine monoclonal antibody was added to each tube. Each tube was incubated at room temperature for 10 minutes. Cells were washed 3× in M2 media. 10 μl of mouse anti-IgG FITC was added to each tube. Tubes were incubated at room temperature in dark conditions for 10 minutes. Endometrial cells were mounted on glass slides and viewed under a fluorescence microscope.

Test for Direct Agglutination:

5 μl of each group of cells was placed onto separate microscope slides. To each 5 μl drop of cells 5 μl of a corresponding antibody was added. The cells were gently mixed on the slide for 2 minutes. Agglutination was visualised under the microscope. The results are presented in Table 55.

TABLE 54

Antisera used for results presented in Table 55.

| Antisera | Manufacturer | |
|---|---|---|
| Bioclone anti-A | Ortho Diagnostics | 01102 D.O.M. 16.05.02 |
| Bioclone anti-B | Ortho Diagnostics | Developmental reagent |

TABLE 55

Endometrial cells transformed with $A_{tri}$-sp-Ad-DOPE (I) or $B_{tri}$-sp-Ad-DOPE A (VI), as visualised using fluorescence.

| Cell Type | Inserted Antigen | 1° antibody | Fluorescence score after incubation with IgFITC Probe | Agglutination reaction by microscopic visualisation |
|---|---|---|---|---|
| Endometrial cells | $A_{tri}$-sp-Ad-DOPE (I) (1 mg/ml) | Anti-A Bioclone | 4+ | 4+ |
| Endometrial cells | $B_{tri}$-sp-Ad-DOPE (VI) (1 mg/ml) | Anti-B Bioclone | 1+ | 3+ |
| Endometrial cells | Control (M2 media) | Anti-A Bioclone | 0 | 0 |

Embryo Modification
Insertion of Water Soluble Synthetic Molecule Construct:

The embryo zona pellucida was removed by treating embryos with 0.5% pronase in a 37° C. oven for 6 minutes or until all zonas were removed. Micro-drops were prepared by adding 5 µl of synthetic glycolipid $A_{tri}$-sp-Ad-DOPE (I) or $B_{tri}$-sp-Ad-DOPE (VI), at a concentration of 1 mg/mL to a 45 µl drop of M2 media overlaid with mineral oil. All embryo groups were incubated in the 50 µl micro-drops for 1 hour at 37° C. Embryos from experimental and control groups were washed 3× with M2 media.

Test for Insertion:

Embryos from experimental and control groups were placed into a micro-drop of corresponding antibody and incubated for 30 min at 37° C. Embryos from experimental and control groups were washed 3× with M2 media.

Embryos from all experimental and control groups were placed into micro-drops of anti-mouse Ig FITC (1:50 dilution anti-mouse Ig FITC in M2) and incubated for 30 min at 37° C. Embryos from experimental and control groups were washed 3× with M2 media. Embryos were mounted on microscope slides in a 5 µl drop of M2 and the drops overlaid with oil.

The slides were viewed under a fluorescence microscope. Results are presented in Tables 56 and 57. The negative result for transformation with $B_{tri}$-sp-Ad-DOPE (VI) is attributed to a lack of 1° antibody sensitivity.

TABLE 56

Embryos transformed with $A_{tri}$-sp-Ad-DOPE (I) as visualised using fluorescence.

| Cell Type | Inserted Antigen | 1° antibody | Fluorescence score after incubation with IgFITC Probe | Embryo Morphology 24 hr post insertion |
|---|---|---|---|---|
| Embryos | $A_{tri}$-sp-Ad-DOPE (I) | Anti-A Bioclone | 2+/1+ | Appeared viable |
| Embryos | Control | Anti-A Bioclone | 0 | Appeared viable |

TABLE 57

Embryos transformed with $A_{tri}$-sp-Ad-DOPE (I) or $B_{tri}$-sp-Ad-DOPE (VI), as visualised using fluorescence.

| Cell Type | Inserted Antigen | 1° antibody | Fluorescence score after incubation with IgFITC Probe | Embryo Morphology 24 hr post insertion |
|---|---|---|---|---|
| Embryos | $A_{tri}$-sp-Ad-DOPE (I) | Anti-A Bioclone | 2+ | n.d. |
| Embryos | $B_{tri}$-sp-Ad-DOPE (VI) | Anti-B Bioclone | 0 | n.d. |
| Embryos | Control (M2 media) | Anti-A Bioclone | 0 | n.d. |

Abbreviations: n.d. Not determined

Enhanced Attachment Transformed Endometrial Cells to Modified Embryos Modified embryos (BioG-Avidin-BiolgG$^B$ and BioG-Avidin-BiolgM$^A$) were prepared in accordance with the methods described in the specification accompanying the international application no. PCT/NZ03/00059 (published as WO03/087346).

Two concave glass slides were prepared, one with two wells of synthetic glycolipid $A_{tri}$-sp-Ad-DOPE (I) inserted endometrial cells and the other with two wells of synthetic glycolipid $B_{tri}$-sp-Ad-DOPE (VI) inserted endometrial cells.

The two groups of embryos were transferred to each of the concave glass slides:
- Slide 1 $A_{tri}$/IgG$^B$ embryos
  $A_{tri}$/IgM$^A$ embryos
- Slide 2 $B_{tri}$/IgG$^B$ embryos
  $B_{tri}$/IgM$^A$ embryos The embryos were surrounded with endometrial cells. The wells were covered with mineral oil and incubated for 15 minutes at 37° C. Using a wide bore handling pipette each group of embryos were carefully transferred to a fresh drop of M2 media. The embryos were gently washed. The embryos were gently transferred into 2 µL of M2 media on a marked microscope slide. Each drop was overlaid with mineral oil Under a central plane of focus on an Olympus microscope the number of endometrial cells adhered to the embryos in each group was assessed. The number of cells adhered to each embryo was recorded. Results are presented in Table 58.

TABLE 58

Endometrial cells transformed with $A_{tri}$-sp-Ad-DOPE (I) or $B_{tri}$-sp-Ad-DOPE (VI), and embryos modified with BioG-Avidin-BioIgG$^B$ or BioG-Avidin-BioIgM$^A$.
Assessment by attachment of endometrial cells to embryos.

| Cell Type | Transformed endometrial cells | Modified embryos | Average number of endometrial cells attached to modified embryos |
|---|---|---|---|
| Endometrial cells | $A_{tri}$-sp-Ad-DOPE (I) | BioG-Avidin-BioIgG$^B$ | 2.3 |
|  |  | BioG-Avidin-BioIgM$^A$ | 7.25 |
| Endometrial cells | $B_{tri}$-sp-Ad-DOPE (VI) | BioG-Avidin-BioIgG$^B$ | 6.7 |
|  |  | BioG-Avidin-BioIgM$^A$ | 3.4 |

Where in the foregoing description reference has been made to integers or components having known equivalents then such equivalents are herein incorporated as if individually set forth.

Although the invention has been described by way of example and with reference to possible embodiments thereof it is to be appreciated that improvements and/or modification may be made thereto without departing from the scope or spirit of the invention.

REFERENCES

Abe K, McKibbin J M & Hakomori S I. (1983) The monoclonal antibody directed to difucosylated type 2 chain (Fucα1→2Galβ1→4[Fucα1→3]GlcNAc; Y determinant). J. Biol. Chem. 258: 11793-11797.

Adamany A M, Blumenfeld O O, Sabo B & McCreary J. (1983) A carbohydrate structural variant of MM glycoprotein (glycophorin A). J. Biol. Chem. 258: 11537-11545.

Blanchard D, Cartron J P, Fournet B, Mountreuil J, van Halbeek H & Vliegenthart J F G. (1983) Primary structure of the oligosaccharide determinant of blood group Cad specificity. J. Biol. Chem. 258: 7691-7695.

Fukuda M, Dell A & Fukuda M. (1984a) Structure of fetal lactosaminoglycan. The carbohydrate moiety of band 3 isolated from human umbilical cord erythrocytes. J. Biol. Chem. 259: 4782-4791.

Fukuda M, Dell A, Oates J E & Fukuda M. (1984b) Structure of branched lactosaminoglycan, the carbohydrate moiety of band 3 isolated from adult human erythrocytes. J. Biol. Chem. 259: 8260-8273.

Fukuda M, Lauffenberger M, Sasaki H, Rogers M E & Dell A. (1987) Structures of novel sialylated O-linked oligosaccharides isolated from human erythrocyte glycophorins. J. Biol. Chem. 262: 11952-11957.

Fukuda M N, Dell A, Oates J E, Wu P, Klock J C & Fukuda M. (1985) Structures of glycosphingolipids isolated from human granulocytes. The presence of a series of linear poly-N-acetyllactosaminylceramide and its significance in glycolipids of whole blood cells. J. Biol. Chem. 260: 1067-1082.

Gillard B K, Blanchard D, Bouhours J F, Cartron J P, van Kuik J A, Kamerling J P, Vliegenthart J F G & Marcus D M. (1988) Structure of a ganglioside with Cad blood group antigen activity. Biochemistry. 27: 4601-4604.

Hakomori S I, Nudelman E, Levery S B & Kannagi R. (1984) Novel fucolipids accumulating in human adenocarcinoma. I. Glycilipids with di- or trifucosylated type 2 chain. J. Biol. Chem. 259: 4672-4680

Hanfland P. (1975) Characterisation of B and H blood group active glycosphingolipids from human B erythrocyte membranes. Chem. Phys. Lipids. 15: 105-124.

Hanfland P, Kordowicz M, Niermann H, Egge H, Dabrowski U, Peter-Katalinic J & Dabrowski J. (1984) Purification and structures of branched blood-group-B-active glycosphingolipids from human erythrocyte membranes. Eur. J. Biochem. 145: 531-542.

Hanfland P, Kordowicz M, Peter-Katalinic J, Pfannschmidt G, Crawford R J, Graham H A & Egge H. (1986) Immunochemistry of the Lewis blood-group system: isolation and structures of Lewis-c active and related glycosphingolipids from the plasma of blood-group O Le(a-b-) nonsecretors. Arch. Biochem. Biophys. 246: 655-672.

Hiraiwa N, Tsuyuoka K, Li Y T, Tanaka M, Seno T, Okubo Y, Fukuda Y, Imura H & Kannagi R. (1990) Gangliosides and sialoglycoproteins carrying a rare blood group antigen determinant, Cad, associated with human cancers as detected by specific monoclonal antibodies. Cancer Res. 50: 5497-5503.

Kannagi R, Nudelman E, Levery S B, & Hakomori S I. (1982) A series of human erythrocytes glycosphingolipids reacting to the monoclonal antibody directed to a developmentally regulated antigen, SSEA-1. J. Biol. Chem. 257: 14865-14874.

Kewitz S, Groβ H J, Kosa R & Roelcke D. (1995) Anti=Pr cold agglutinins recognise immunodominant α2,3- or α2,6-sialyl groups on glycophorins. Glycocon. J. 12: 714-720.

Koscielak J, Miller-Podraza H, Krauze R & Piasek A. (1976) Isolation and characterisation of poly(glycosyl)ceramides (megaloglycolipids) with A, H, and I blood group activities. Eur. J. Biochem. 71: 9-18.

Laine R A. (1994) Invited commentary. Glycobiol 4: 759-767

Lidowska E, Duk M & Dahr W. (1980) Comparison of alkali-labile oligosaccharide chains of M and N blood-group glycopeptides from human erythrocyte membrane. Carbohydr. Res. 79: 103-113.

Lloyd K O & Kabat E A. (1968) Immunochemical studies on blood groups. XLI. Proposed structures for the carbohydrate portions of blood group A, B, H, Lewis$^a$, and Lewis$^b$ substances. Proc. Natl. Acad. Sci. USA. 61: 1470-1477.

Lundblad A. (1977) Urinary glycoproteins, glycopeptides, and oligosaccharides. In: The Glycoconjugates Eds Horowitz M I & Pigman W. Vol 1: 441-458.

Magnani J L, Nilsson B, Brockhaus M, Zopf D, Steplewski Z, Koprowski H & Ginsburg V. (1986) A monoclonal antibody-defined antigen associated with gastrointestinal cancer is a ganglioside containing sialylated lacto-N-fucopentaose II. J. Biol. Chem. 257: 14365-14369.

Nudelman E, Fukushi Y, Levery S B, Higuchi T & Hakomori S I. (1986) Novel fucolipids of human adenocarcinoma: disialoyl Le$^a$ antigen (III$^4$FucIII$^6$NeuAcIV$^3$NeuAcLc$_4$) of human colonic adenocarcinoma and the monoclonal antibody (FH7) defining this structure. J. Biol. Chem. 261: 5487-5495.

Slomiany A, Zdebska E & Slomiany B L. (1984) Structures of the neutral oligosaccharides isolated from A-active human gastric mucin. J. Biol. Chem. 259: 14743-14749.

Takasaki S, Yamashita K & Kobata A. (1978) The sugar chain structures of ABO blood group active glycoproteins obtained from human erythrocyte membrane. J. Biol. Chem. 253: 6086-6091.

Tanaka M, Dube V E & Anderson B. (1984) Structures of oligosaccharides cleaved by base-borohydride from an I, H, and Le$^a$ active ovarian cyst glycoprotein. Biochim. Biophys. Acta. 798: 283-290.

Thomas D B & Winzler R J. (1969) Structural studies on human erythrocytes glycoprotein. Alkali-labile oligosaccharides. J. Biol. Chem. 244: 5943-5946.

Watkins W M. (1966) Blood group substances. Science. 152: 172-181.

Yoshima H, Furthmayr H & Kobata A. (1980) Structures of the asparagine-linked sugar chains of glycophorin A. J. Biol. Chem. 255: 9713-9718.

The invention claimed is:

1. Cells incorporating a synthetic molecule construct of the structure F—S$_1$-S$_2$-L where: F—S$_1$ is an aminoalkylglycoside where F is a mono-, di-, tri- or oligo-saccharide and S$_1$ is 2-aminoethyl, 3-aminopropyl, 4-aminobutyl, or 5-aminopentyl; S$_2$ is —CO(CH$_2$)$_2$CO—, —CO(CH$_2$)$_3$CO—, —CO(CH$_2$)$_4$CO— or —CO(CH$_2$)$_5$CO—; and L is phosphatidylethanolamine.

2. The cells of claim 1 where F is selected from the group consisting of: GalNAcα1-3(Fucα1-2)Galβ; Galα1-3Galβ; Galβ; Galα1-3(Fucα1-2)Galµ; NeuAcα2-3Galβ; NeuAcα2-6Galβ; Fucα1-2Galβ; Galβ1-4GlcNAcβ1-6(Galβ1-4GlcNAcβ1-3)Galβ; Fucα1-2Galβ1-4GlcNAcβ1-6(Fucα1-2Galβ1-4GlcNAcβ1-3)Galβ; Fucα1-2Galβ1-4GlcNAcβ1-6 (NeuAcα2-3Galβ1-4GlcNAcβ1-3)Galβ; NeuAcα2-3Galβ1-4GlcNAcβ1-6(NeuAcα2-3Galβ1-4GlcNAcβ1-3) Galβ; Galα1-4Galβ1-4Glc; GalNAcβ1-3Galα1-4Galβ1-4Glc; GalNAcα1-3GalNAcβ1-3Galα1-4Galβ1-4Glc; or GalNAcβ1-3GalNAcβ1-3Galα1-4Galβ1-4Glc.

3. The cells of claim 2 where F is selected from the group consisting of: GalNAcα1-3(Fucα1-2)Galβ and Galα1-3 (Fucα1-2)Galβ.

4. The cells of claim 3 where S$_1$ is 3-aminopropyl.

5. The cells of claim 1 where L is 1,2-O-dioleoyl-sn-glycero-3-phosphatidylethanolamine (DOPE) or 1,2-O-distearyl-sn-glycero-3-phosphatidylethanolamine (DSPE).

6. The cells of claim 5 where the construct is:

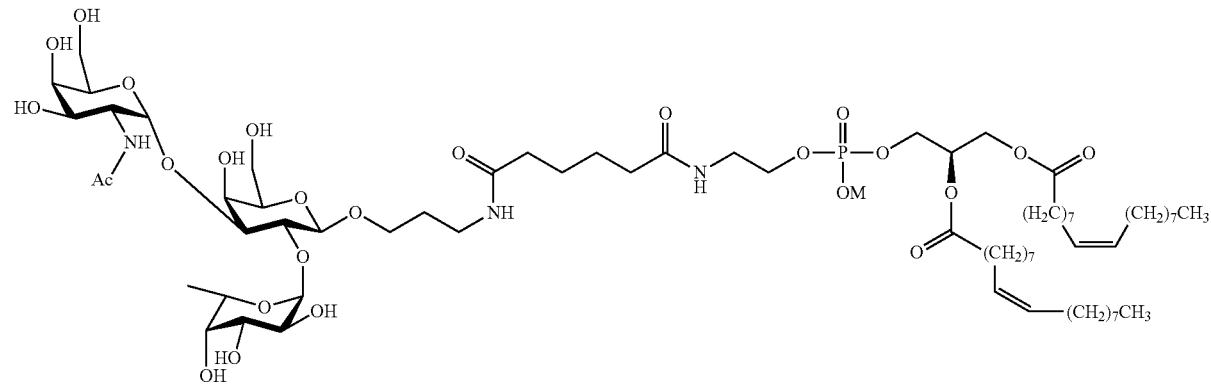

designated A$_{tri}$-sp-Ad-DOPE (I) where M is a monovalent cation.

7. The cells of claim 5 where the construct is:

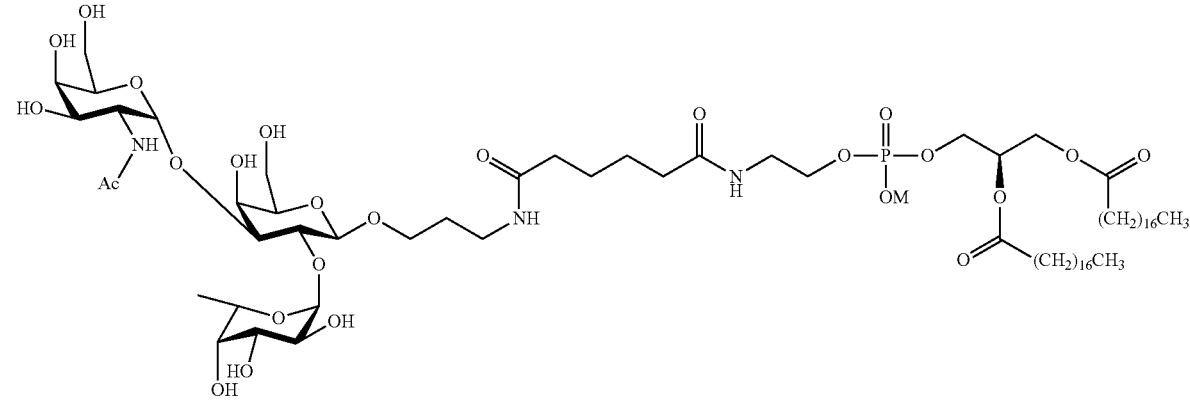

designated A$_{tri}$-sp-Ad-DSPE (III) where M is a monovalent cation.

8. The cells of claim 5 where the construct is:

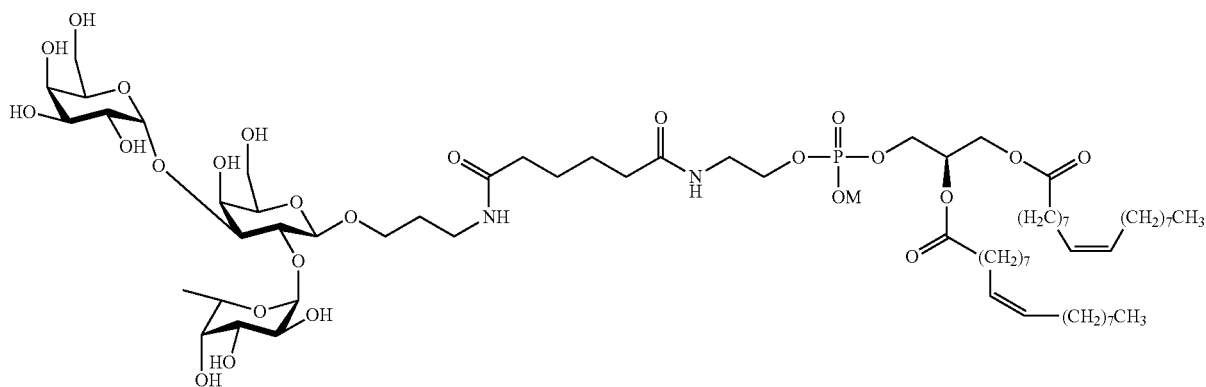

designated B$_{tri}$-sp-Ad-DOPE (VI) where M is a monovalent cation.

9. The cells of claim 5 where the construct is:

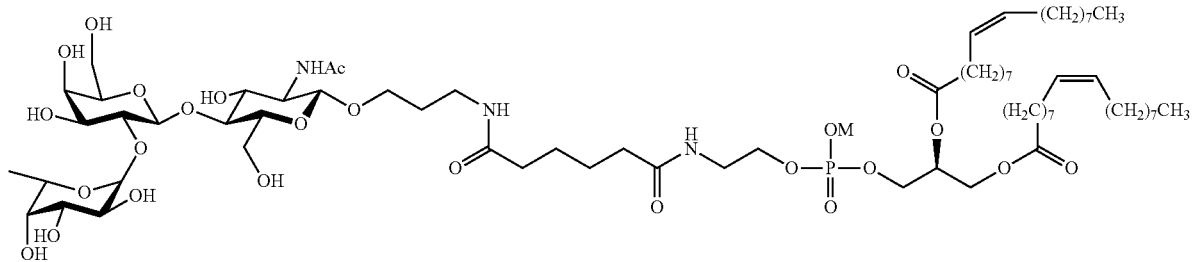

designated H$_{tri}$-sp-Ad-DOPE (VII) where M is a monovalent cation.

10. The cells of claim 5 where the construct is:

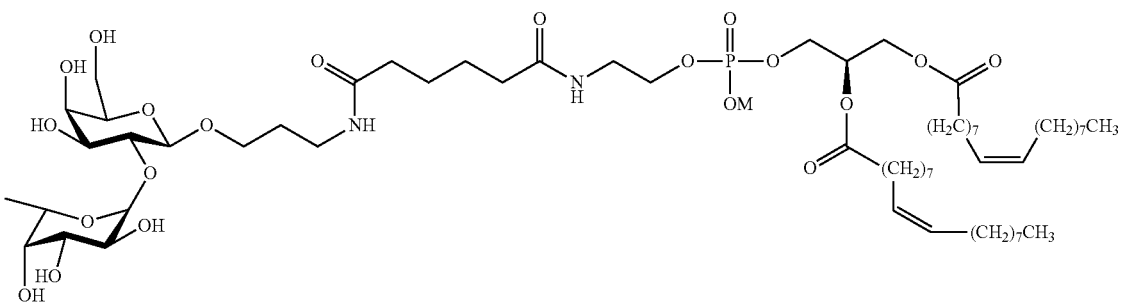

designated H$_{di}$-sp-Ad-DOPE (VIII) where M is a monovalent cation.

11. The cells of claim 5 where the construct is:

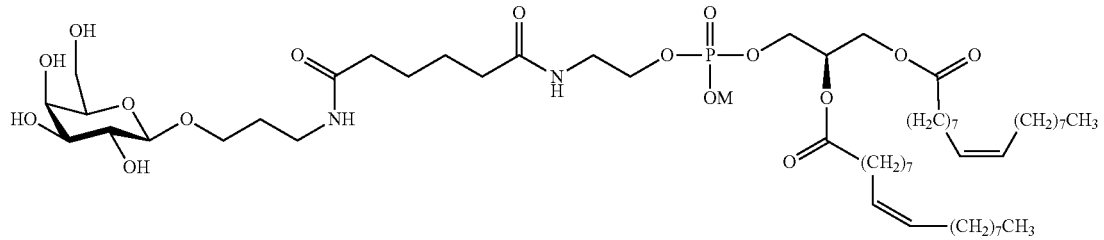

designated Galβ-sp-Ad-DOPE (IX) where M is a monovalent cation.

12. The cells of claim 5 where the construct is:
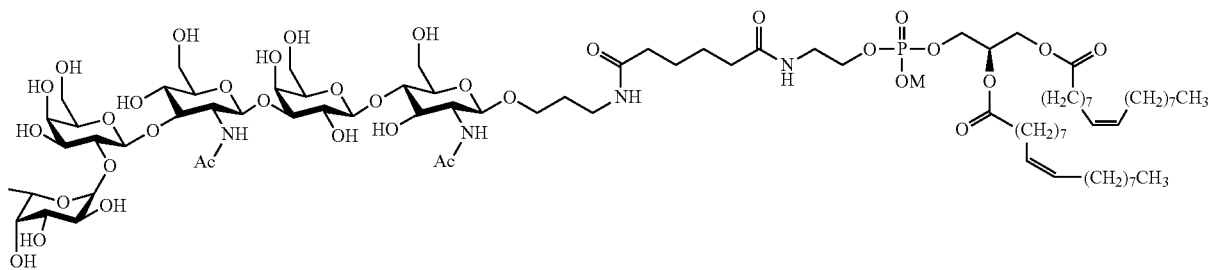
designated Fucα1-2Galβ1-3GlcNAcβ1-3Galβ1-4GlcNAc-sp-Ad-DOPE (XII) where M is a monovalent cation.
13. The cells of claim 5 where the construct is:
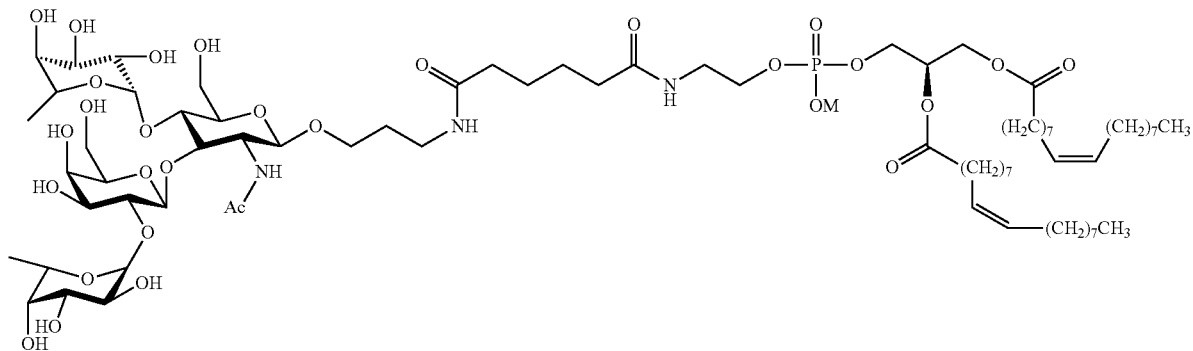
designated Fucα1-2Galβ1-3(Fucα1-4)GlcNAc-sp-Ad-DOPE (XIII) where M is a monovalent cation.
14. The cells of claim 1 where the cells are blood cells.
15. The cells of claim 14 where the cells are red blood cells.
* * * * *